US012673219B2

(12) United States Patent
Robar et al.

(10) Patent No.: US 12,673,219 B2
(45) Date of Patent: Jul. 7, 2026

(54) PATIENT-SPECIFIC IMMOBILIZATION STRUCTURE AND SYSTEM AND METHOD FOR FABRICATION THEREOF

(71) Applicant: ADAPTIIV MEDICAL TECHNOLOGIES INC., Halifax (CA)

(72) Inventors: James L. Robar, Halifax (CA); Christopher Majcher, Dartmouth (CA); Radojka Orbovic, Halifax (CA)

(73) Assignee: ADAPTIIV MEDICAL TECHNOLOGIES INC., Halifax (CA)

( * ) Notice: Subject to any disclaimer, the term of this patent is extended or adjusted under 35 U.S.C. 154(b) by 1041 days.

(21) Appl. No.: 17/668,672

(22) Filed: Feb. 10, 2022

(65) Prior Publication Data

US 2022/0249866 A1 Aug. 11, 2022

Related U.S. Application Data

(60) Provisional application No. 63/148,260, filed on Feb. 11, 2021.

(51) Int. Cl.
*A61N 5/10* (2006.01)
*B33Y 50/02* (2015.01)
*B33Y 80/00* (2015.01)

(52) U.S. Cl.
CPC .............. *A61N 5/103* (2013.01); *B33Y 50/02* (2014.12); *B33Y 80/00* (2014.12); *A61N 2005/1097* (2013.01)

(58) Field of Classification Search
None
See application file for complete search history.

(56) References Cited

U.S. PATENT DOCUMENTS 5,566,681 A * 10/1996 Manwaring ............ A61B 90/17
128/845
5,702,406 A 12/1997 Mlsmeier et al.
(Continued)

FOREIGN PATENT DOCUMENTS

WO 2016124232 A1 8/2016
WO 2019023610 A1 1/2019
WO WO-2020099510 A2 * 5/2020 ........... A61N 5/1049

OTHER PUBLICATIONS

Bioinnovation, "BioInnovation 2018—Incubator Prize (3D printed breast shell for breast radiotherapy)," YouTube video, uploaded Jun. 11, 2018. URL: https://www.youtube.com/watch?v=450JHuMf7P4 (1 page).

(Continued)

*Primary Examiner* — Andrew Smyth
(74) *Attorney, Agent, or Firm* — Stephen Leonard; Aird & McBurney LP

(57) ABSTRACT

Systems and methods are provided for modelling and fabricating a patient-specific immobilization support. Image data is obtained for characterizing an exposed surface of a body portion and a support structure employed to support the body portion during imaging. The image data is processed to determine a position and orientation of the support structure based on spatial features of the support structure, and surface data associated with the exposed surface of the body portion is segmented from the image data. The segmented surface data and the position and orientation of the support structure are employed to generate a digital model of a patient-specific immobilization structure that is attachable to the support structure for immobilizing the body portion between the patient-specific immobilization structure and the support structure. Prior to fabricating the patient-specific immobilization structure, an initial digital model may be (Continued)

modified, optionally according to beam parameters associated with a treatment plan.

46 Claims, 37 Drawing Sheets

(56)                References Cited

U.S. PATENT DOCUMENTS

| | | | |
|---|---|---|---|
| 5,775,337 | A | 7/1998 | Hauger et al. |
| 8,320,648 | B2 | 11/2012 | Mailling et al. |
| 9,808,648 | B2 | 11/2017 | De Mooij |
| 10,350,435 | B2 | 7/2019 | Robar et al. |
| 10,786,385 | B2 | 9/2020 | De Gruytere |
| 2008/0078410 | A1 | 4/2008 | De Mooy et al. |
| 2011/0118527 | A1 | 5/2011 | Giesel et al. |
| 2014/0330417 | A1* | 11/2014 | Keane .................... A61B 90/18 |
| | | | 700/98 |
| 2015/0335463 | A1 | 11/2015 | De Gruytere |
| 2017/0296845 | A1 | 10/2017 | Tallhamer et al. |
| 2017/0333243 | A1 | 11/2017 | Coppens |
| 2018/0001547 | A1 | 1/2018 | Cuypers et al. |
| 2020/0139154 | A1 | 5/2020 | Wilson et al. |

OTHER PUBLICATIONS

Robertson, F., "A Comparison of Thermoplastic and 3D Printed Beam Directional Shells on Viability for External Beam Radiotherapy and User Experience," M. Sc. Thesis, Queen Margaret University Research Repository, 2017, Item No. 119, 48 pp. (1 page).

Loja, M.A.R.; Craveiro, D.S.; Vieira, L.; Sousa, E.; Rodrigues, J.A.; Portal, R.J.F., "Radiotherapy-customized head immobilization masks: from modeling and analysis to 3D printing," Nuclear Science and Techniques, vol. 30, article 142, 2019. DOI: 10.1007/s41365-019-0667-2. (16 pages).

Reddy, K., "Primary radiotherapy for locally advanced skin cancer near the lateral canthus when surgical management was contraindicated," Practical Radiation Oncology, 2012. DOI: 10.1016/S1879-8500(11)00168-8. (10 pages).

"3D Printed Boluses Help to Improve Radiotherapy Standards," undated article (trade publication), Zortrax, 2017. (8 pages).

Asfia, A., Novak, J. I., Mohammed, M. I., Rolfe, B., and Kron, T., "A review of 3D printed patient specific immobilisation devices in radiotherapy," Physics and Imaging in Radiation Oncology, vol. 13, pp. 30-35, 2020. (6 pages).

Robertson, F. et al., "A Comparison of User Experience and Accuracy of set-up in the Use of Thermoplastic and 3D Printed Beam Directional Shells for External Beam Radiotherapy", All for One—Collaborating and Innovating for Person Centred Care Conference, Montreal, 2018. (17 pages).

Extended European Search Report for PCT/CA2022/050194 dated Feb. 13, 2025, 6 pages.

International Search Report for PCT/CA2022/050194 dated Jun. 15, 2022, 3 pages.

* cited by examiner

110

105

BASE PLATE

HEAD REST

FROM STEP 215 OF FIG. 4

220

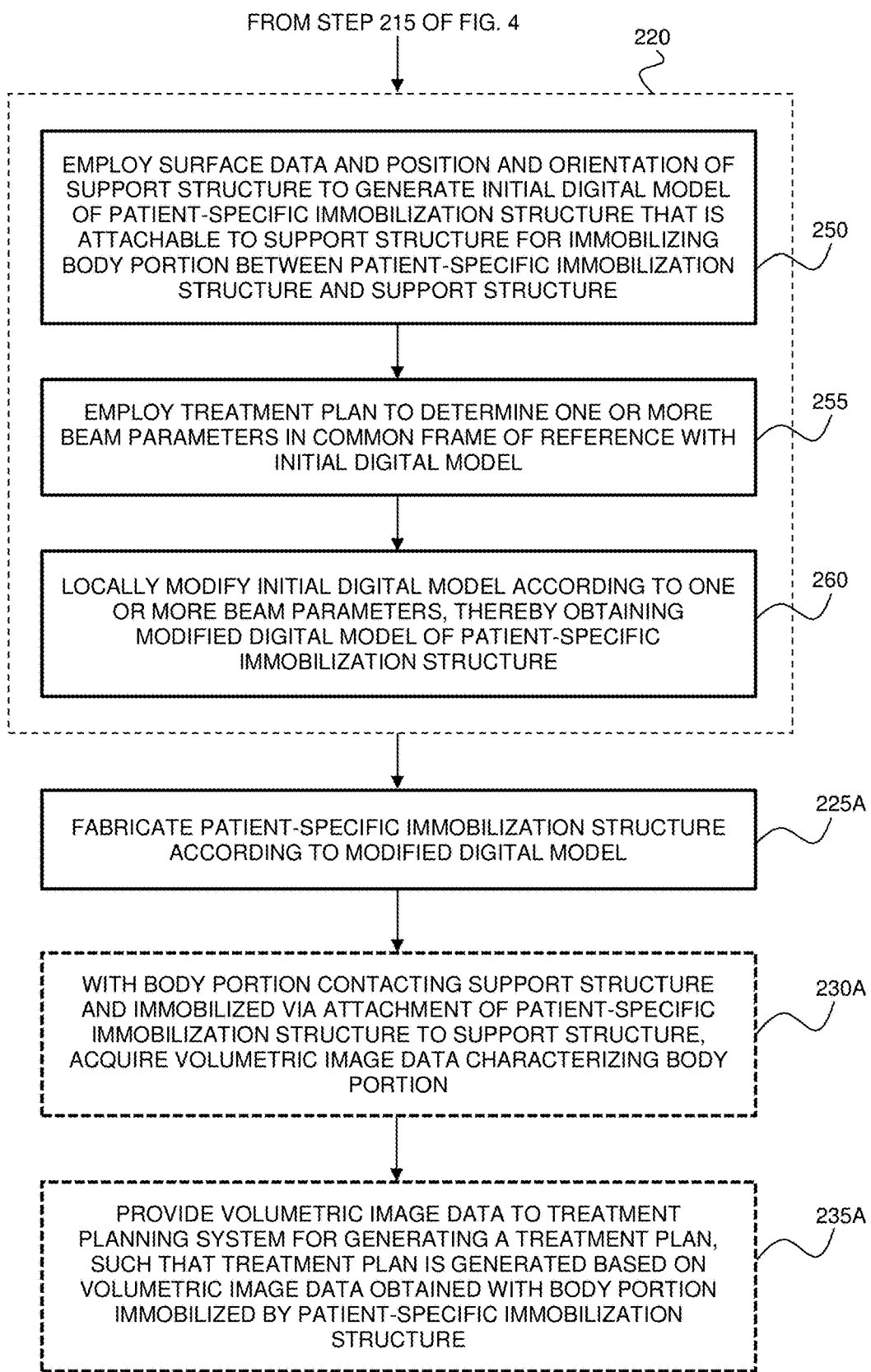

EMPLOY SURFACE DATA AND POSITION AND ORIENTATION OF SUPPORT STRUCTURE TO GENERATE INITIAL DIGITAL MODEL OF PATIENT-SPECIFIC IMMOBILIZATION STRUCTURE THAT IS ATTACHABLE TO SUPPORT STRUCTURE FOR IMMOBILIZING BODY PORTION BETWEEN PATIENT-SPECIFIC IMMOBILIZATION STRUCTURE AND SUPPORT STRUCTURE

250

EMPLOY TREATMENT PLAN TO DETERMINE ONE OR MORE BEAM PARAMETERS IN COMMON FRAME OF REFERENCE WITH INITIAL DIGITAL MODEL

255

LOCALLY MODIFY INITIAL DIGITAL MODEL ACCORDING TO ONE OR MORE BEAM PARAMETERS, THEREBY OBTAINING MODIFIED DIGITAL MODEL OF PATIENT-SPECIFIC IMMOBILIZATION STRUCTURE

260

FABRICATE PATIENT-SPECIFIC IMMOBILIZATION STRUCTURE ACCORDING TO MODIFIED DIGITAL MODEL

225A

WITH BODY PORTION CONTACTING SUPPORT STRUCTURE AND IMMOBILIZED VIA ATTACHMENT OF PATIENT-SPECIFIC IMMOBILIZATION STRUCTURE TO SUPPORT STRUCTURE, ACQUIRE VOLUMETRIC IMAGE DATA CHARACTERIZING BODY PORTION

230A

PROVIDE VOLUMETRIC IMAGE DATA TO TREATMENT PLANNING SYSTEM FOR GENERATING A TREATMENT PLAN, SUCH THAT TREATMENT PLAN IS GENERATED BASED ON VOLUMETRIC IMAGE DATA OBTAINED WITH BODY PORTION IMMOBILIZED BY PATIENT-SPECIFIC IMMOBILIZATION STRUCTURE

PATIENT-SPECIFIC IMMOBILIZATION STRUCTURE AND SYSTEM AND METHOD FOR FABRICATION THEREOF

CROSS-REFERENCE TO RELATED APPLICATIONS

This application claims priority to U.S. Provisional Patent Application No. 63/148,260, titled "PATIENT-SPECIFIC IMMOBILIZATION STRUCTURE AND SYSTEM AND METHOD FOR FABRICATION THEREOF" and filed on Feb. 11, 2021, the entire contents of which is incorporated herein by reference.

BACKGROUND

The present disclosure relates to patient immobilization devices. More specifically, the present disclosure relates to patient immobilization devices for use during radiotherapy procedures.

The immobilization of a patient or a body portion of a patient is often required during a wide variety of medical procedures. For example, during radiotherapy procedures, the irradiated body portion is immobilized to ensure that the radiation dose is delivered to a target location that is predetermined according to a treatment plan.

One conventional approach to patient immobilization involves the use of a heat-formable structure, such as a thermoplastic mask, to obtain a patient-specific mask that is contoured according to the underlying patient anatomy. For example, as illustrated in FIG. 1. As shown in step 10, a thermoplastic mesh sheet 30 is provided, where the sheet 30 is retained by a frame 32 having alignment pins 34. The thermoplastic mesh 30 is heated, for example, by immersion in a hot water bath, and is subsequently stretched over the patient anatomy, as shown at steps 15-25, until the thermoplastic mesh 30 is sufficiently stretched to enable the frame 32 to contact the base 36. As the thermoplastic mesh cools, it is formed over curved areas of the patient anatomy in order to improve the conformal fit. As shown in step 25, the alignment pins 32 engage with holes in the base 36 to secure the resulting immobilization mask to the base 36.

SUMMARY

Systems and methods are provided for modelling and fabricating a patient-specific immobilization support. Image data is obtained for characterizing an exposed surface of a body portion and a support structure employed to support the body portion during imaging. The image data is processed to determine a position and orientation of the support structure based on spatial features of the support structure, and surface data associated with the exposed surface of the body portion is segmented from the image data. The segmented surface data and the position and orientation of the support structure are employed to generate a digital model of a patient-specific immobilization structure that is attachable to the support structure for immobilizing the body portion between the patient-specific immobilization structure and the support structure. Prior to fabricating the patient-specific immobilization structure, an initial digital model may be modified, optionally according to beam parameters associated with a treatment plan.

Accordingly, in a first aspect, there is provided a method of fabricating an immobilization device for immobilizing a body portion of a patient, the method comprising:

providing a support structure suitable for supporting a body portion of the patient;

with the body portion supported by contact with the support structure, employing an imaging system to obtain image data suitable for characterizing an exposed surface of the body portion and at least a portion of the support structure;

processing the image data to determine a position and orientation of the support structure based on one or more known spatial features of the support structure;

processing the image data to segment surface data associated with the exposed surface of the body portion;

employing the surface data and the position and orientation of the support structure to generate a digital model of a patient-specific immobilization structure that is attachable to the support structure for immobilizing the body portion between the patient-specific immobilization structure and the support structure; and fabricating the patient-specific immobilization structure according to the digital model.

In some example implementations of the method, the patient-specific immobilization structure comprises an alignment feature configured to contact a corresponding feature of the support structure for aligning the patient-specific immobilization structure relative to the support structure prior to attachment. The alignment feature of the patient-specific immobilization structure may comprise a first surface that is configured to contact a corresponding second surface of the support structure when the patient-specific immobilization structure is aligned with the support structure for immobilizing the body portion between the patient-specific immobilization structure and the support structure.

In some example implementations of the method, at least one of the one or more known spatial features are fiducial features.

In some example implementations of the method, the surface data is segmented, at least in part, by employing the one or more known spatial features of the support structure to remove support structure image data associated with the support structure from the image data.

In some example implementations of the method, the digital model of the patient-specific immobilization structure comprises at least one attachment feature that facilitates attachment of the patient-specific immobilization structure with the support structure when the patient-specific immobilization structure is aligned with the support structure for immobilizing the body portion between the patient-specific immobilization structure and the support structure. At least one attachment feature of the patient-specific immobilization structure cooperates with a respective attachment feature of the support structure for attaching the patient-specific immobilization structure to the support structure.

In some example implementations of the method, the digital model of the patient-specific immobilization structure comprises:

a conformal shell region conforming to at least a portion of the surface data associated with the exposed surface of the body portion; and an extrusion region that extends from the conformal shell region to the support structure. The support structure may comprise planar surface, and wherein a direction of extrusion is perpendicular to the planar surface.

In some example implementations of the method, the image data is initial image data, the method further comprising:

with the body portion contacting the support structure and immobilized via attachment of the patient-specific immobilization structure to the support structure, acquiring volumetric image data characterizing the body portion; and providing the volumetric image data to a treatment planning system for generating a treatment plan, such that the treatment plan is generated based on the volumetric image data obtained with the body portion immobilized by the patient-specific immobilization structure. The method may further include employing the patient-specific immobilization structure to immobilize the body portion during a therapeutic procedure performed according to the treatment plan.

In some example implementations, the method further comprises employing the digital model of the patient-specific immobilization structure to generate a treatment plan with a treatment planning system.

In some example implementations of the method, the patient-specific immobilization structure is associated with a radiotherapy procedure, the radiotherapy procedure having an associated treatment plan, and wherein generating the digital model comprises:

employing the surface data and the position and orientation of the support structure to generate an initial digital model of the patient-specific immobilization structure that is attachable to the support structure for immobilizing the body portion between the patient-specific immobilization structure and the support structure;

employing the treatment plan to determine one or more beam parameters in a common frame of reference with the initial digital model;

locally modifying the initial digital model according to the one or more beam parameters, thereby obtaining a modified digital model of the patient-specific immobilization structure;

wherein the patient-specific immobilization structure is fabricated according to the modified digital model.

The treatment plan may be an initial treatment plan, and the method may further comprise:

with the body portion immobilized relative to the support structure via attachment of the patient-specific immobilization structure to the support structure, acquiring volumetric image data characterizing the body portion and the one or more spatial features; and providing the volumetric image data to a treatment planning system for generating a refined treatment plan, such that the refined treatment plan is based on the volumetric image data obtained with the body portion immobilized by the patient-specific immobilization structure.

The method may further comprise employing the patient-specific immobilization structure, fabricated according to the modified digital model of the patient-specific immobilization structure, to immobilize the body portion during a therapeutic procedure performed according to the refined treatment plan. The one or more beam parameters may comprise one or more of a beam position, beam angle, beam dimension, and beam shape. The one or more beam parameters may be associated with one or more of an entrance beam and an exit beam.

Locally modifying the initial digital model may comprise locally thinning the initial digital model within an intersection region characterized by intersection with a planned radiation beam, locally varying a density of the initial digital model within an intersection region characterized by intersection with a planned radiation beam, locally varying a material type of the initial digital model within an intersection region characterized by intersection with a planned radiation beam, modifying the initial digital model to include an aperture within an intersection region characterized by intersection with a planned radiation beam, modifying the initial digital model to include a meshed region within an intersection region characterized by intersection with a planned radiation beam, such that porosity of the modified digital model within the intersection region is less than the porosity of the modified digital model within a neighbouring region adjacent to the intersection region (the modified digital model may be solid and absent of mesh structure within the neighbouring region), locally increasing a thickness of the initial digital model to form a radiation bolus within an intersection region characterized by intersection with a planned radiation beam, and displaying, on a user interface, projected locations of radiation beams generated according to the one or more beam parameters and locally modifying the initial digital model according to user input received via the user interface.

In some example implementations of the method, generating the digital model comprises:

employing the surface data and the position and orientation of the support structure to generate an initial digital model of the patient-specific immobilization structure that is attachable to the support structure for immobilizing the body portion between the patient-specific immobilization structure and the support structure;

receiving, via a user interface, user input for modifying the initial digital model of the patient-specific immobilization structure;

locally modifying the initial digital model according to user input, thereby obtaining a modified digital model of the patient-specific immobilization structure;

wherein the patient-specific immobilization structure is fabricated according to the modified digital model.

In some example implementations of the method, the support structure comprises a baseplate. The one or more spatial features may be integrated with or supported by the baseplate. The digital model of the patient-specific immobilization structure may comprise a flange that is configured to contact a surface of the baseplate when the patient-specific immobilization structure is spatially registered with the support structure for immobilizing the body portion between the patient-specific immobilization structure and the support structure. The flange of the patient-specific immobilization structure may comprise one or more first alignment and/or attachment features that are aligned with one or more respective second alignment and/or attachment features in the baseplate when the patient-specific immobilization structure is aligned with the support structure for immobilizing the body portion between the patient-specific immobilization structure and the support structure. The one or more first alignment and/or attachment features may be selected from the group consisting of holes, pins and tabs.

The body portion may comprise at least a portion of a head, with the support structure comprising a headrest secured to or integrally formed with the baseplate. The headrest may be configured to support the head with the patient, and wherein generating the digital model comprises:

processing the surface data to determine a contour of widest coronal cross-section; and extruding the digital model from the contour of widest coronal cross-section, such that the patient-specific immobilization structure comprises an immobilization portion having a patient-specific surface profile suitable for immobilizing the head and an extruded portion that spatially registers the immobilization portion with the baseplate.

The digital model may comprise a flange configured to contact the baseplate when the patient-specific immobilization structure is spatially registered to the support structure for immobilizing the body portion, the flange extending outwardly from the extruded portion in a plane residing parallel to the baseplate and posterior to the patient.

The flange may comprise one or more first holes that are aligned with one or more respective second holes in the baseplate when the patient-specific immobilization structure is aligned with the support structure for immobilizing the body portion between the patient-specific immobilization structure and the support structure.

The baseplate includes at least one positioning feature suitable for removably securing the baseplate to a component of a diagnostic or therapeutic system, such as a patient couch.

In some example implementations of the method, the digital model comprises strap attachment features for securing at least one reinforcing strap, such that when the patient-specific immobilization structure is fabricated and at least one the reinforcing strap is secured to the patient-specific immobilization structure, a rigidity of the patient-specific immobilization structure is increased.

In some example implementations of the method, the imaging system is a surface imaging system, and wherein the image data is surface image data.

In some example implementations of the method, the patient-specific immobilization structure is fabricated with a three-dimensional printer.

In another aspect, there is provided a system for use in generating an immobilization device for immobilizing a body portion of a patient, the system comprising: processing circuitry comprising at least one processor and associated memory, the memory comprising instructions executable by the at least one processor for performing operations comprising:

receiving image data suitable for characterizing an exposed surface of a body portion of the patient and at least a portion of a support structure employed to support the body portion during imaging;

processing the image data to determine a position and orientation of the support structure based on one or more known spatial features of the support structure;

processing the image data to segment surface data associated with the exposed surface of the body portion; and employing the surface data and the position and orientation of the support structure to generate a digital model of a patient-specific immobilization structure that is attachable to the support structure for immobilizing the body portion between the patient-specific immobilization structure and the support structure.

In some example implementations, the system further comprises a fabrication device connectable to the processing circuitry for fabricating the patient-specific immobilization structure according to the digital model.

In another aspect, there is provided a method of generating a digital model of an immobilization device for immobilizing a body portion of a patient, the method comprising:

receiving image data suitable for characterizing an exposed surface of a body portion of the patient and at least a portion of a support structure employed to support the body portion during imaging;

processing the image data to determine a position and orientation of the support structure based on one or more known spatial features of the support structure;

processing the image data to segment surface data associated with the exposed surface of the body portion; and employing the surface data and the position and orientation of the support structure to generate the digital model of a patient-specific immobilization structure that is attachable to the support structure for immobilizing the body portion between the patient-specific immobilization structure and the support structure.

In another aspect, there is provided an immobilization device for immobilizing a body portion of a patient, the method comprising:

obtaining image data suitable for characterizing an exposed surface of the body portion and at least a portion of a support structure employed to support the body portion during imaging;

processing the image data to determine a position and orientation of the support structure based on one or more known spatial features of the support structure;

processing the image data to segment surface data associated with the exposed surface of the body portion; and employing the surface data and the position and orientation of the support structure to generate a digital model of a patient-specific immobilization structure that is attachable to the support structure for immobilizing the body portion between the patient-specific immobilization structure and the support structure.

In another aspect, there is provided a system for generating a digital model of an immobilization device for immobilizing a body portion of a patient, the system comprising:

control and processing circuitry comprising at least one processor and associated memory, the memory comprising instructions executable by the at least one processor for performing operations comprising:

obtaining image data suitable for characterizing an exposed surface of the body portion and at least a portion of a support structure employed to support the body portion during imaging;

processing the image data to determine a position and orientation of the support structure based on one or more known spatial features of the support structure;

processing the image data to segment surface data associated with the exposed surface of the body portion; and employing the surface data and the position and orientation of the support structure to generate a digital model of a patient-specific immobilization structure that is attachable to the support structure for immobilizing the body portion between the patient-specific immobilization structure and the support structure.

In another aspect, there is provided a system for fabricating an immobilization device for immobilizing a body portion of a patient, the system comprising:

an imaging system;

a fabrication system; and control and processing circuitry operatively coupled to the imaging system and the fabrication system, the control and processing circuitry comprising at least one processor and associated memory, the memory comprising instructions executable by the at least one processor for performing operations comprising:

controlling the imaging system to obtain image data suitable for characterizing an exposed surface of the body portion and at least a portion of a support structure employed to support the body portion during imaging;

processing the image data to determine a position and orientation of the support structure based on one or more known spatial features of the support structure;

processing the image data to segment surface data associated with the exposed surface of the body portion;

employing the surface data and the position and orientation of the support structure to generate a digital model of a patient-specific immobilization structure that is attachable to the support structure for immobilizing the body portion between the patient-specific immobilization structure and the support structure; and controlling the fabrication system to fabricate the patient-specific immobilization structure according to the digital model.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 24 is a flow chart illustrating an example method of generating and modifying a digital model of a patient-specific immobilization structure according to beam parameters from an initial radiotherapy treatment plan.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

As used herein, the phrase "patient-specific immobilization structure" refers to an immobilization structure that is customized according to anatomical features of a single, specific patient, based on image data associated with the patient.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Figure 1:
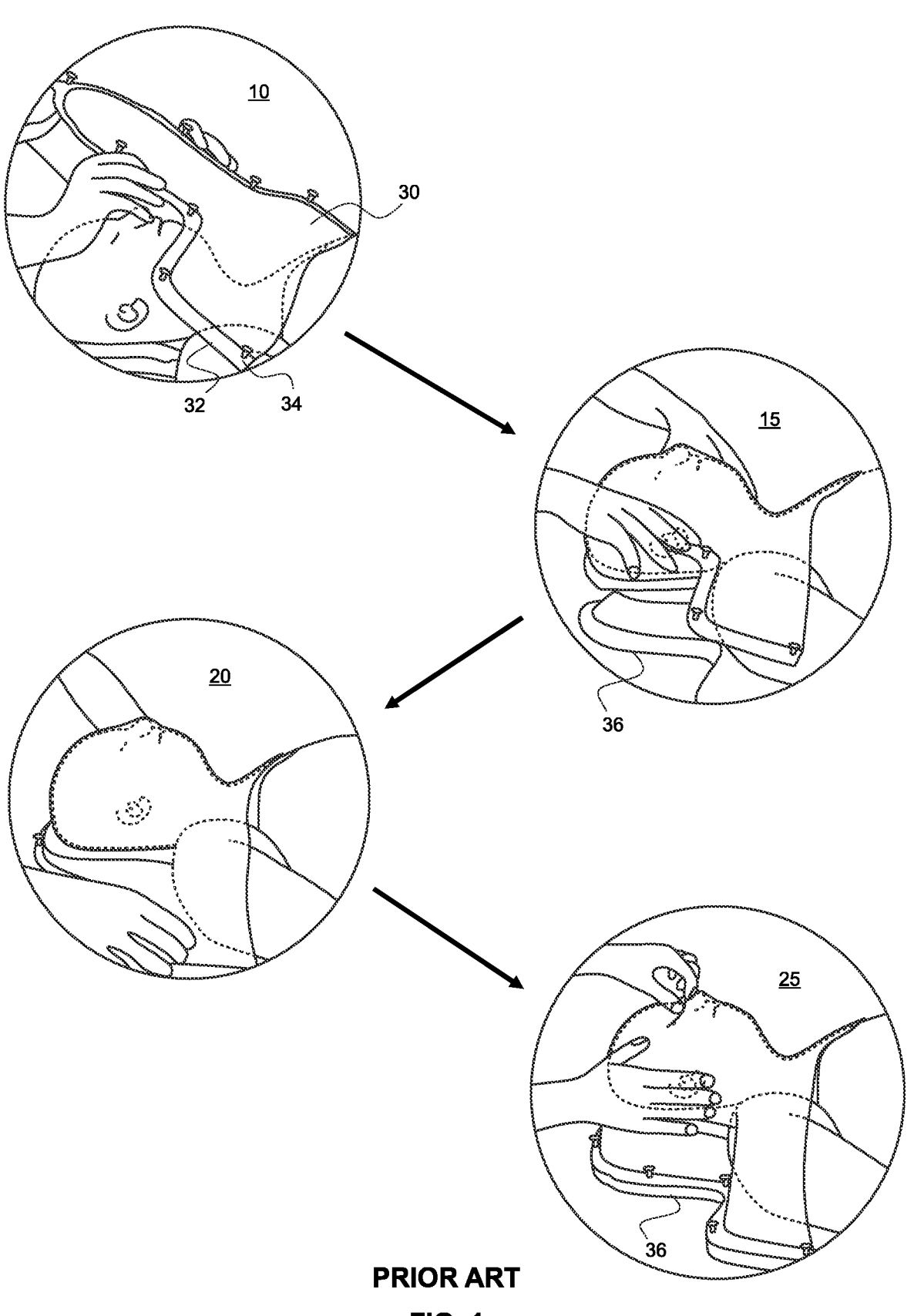
FIG. 1 illustrates a conventional method of performing patient immobilization using a thermoplastic mask.

As described above and illustrated in FIG. 1, the conventional approach to the fabrication of an immobilization structure for immobilizing a patient during a surgical procedure involves an intrusive process the relies on contacting a hot thermoplastic material with the patient anatomy and manually forming the thermoplastic material into a suitable immobilization mask during cooling. The present inventors recognized the limitations of such methods and sought to develop an improved approach that would provide for a better patient experience and reduce the time-consuming and highly manual process of mask fabrication. In addition, the quality of the immobilization produced using this method is highly dependent on the operator; for example, those highly skilled may produce immobilization that fits accurately to the patient, while those less experienced may produce immobilization that introduces gaps between the immobilization and the patient surface, leading to sub-optimal performance of the device. Further, this manual fabrication process requires multiple individuals to form the immobilization and the process often occurs in the suite housing an imaging system, e.g., CT scanner, which introduces operational costs and occupies valuable resources.

In addition, the present inventors realized that the conventional method of forming an immobilization mask using a thermoplastic material was highly limiting in that it fails to facilitate refinement or modification after initial fabrication. For example, once the mask is formed, any further modification requires complex manual modification steps that are expensive, time-consuming, and risk a loss of registration with the patient anatomy. The present inventors thus sought an improved method that would facilitate the design and fabrication of a patient-specific immobilization structure that (i) provides a much less intrusive and less onerous experience to the patient, (ii) avoids the need for manual manipulation of the immobilization structure, (iii) facilitates a reduction in time and cost of immobilization structure fabrication, and (iv) enables the digital modification of a digital model of a patient-specific immobilization structure prior to its fabrication.

Various example embodiments of the present disclosure are thus directed at addressing these goals by employing the use of surface data characterizing a surface of a body portion of a patient to generate a digital model of a patient-specific immobilization structure. Such an approach avoids undue contact and discomfort for the patient, facilitates the accurate immobilization of the body portion of the patient anatomy in a unique fixed position and orientation, and facilitates optional modifications prior to fabrication.

Figure 2:
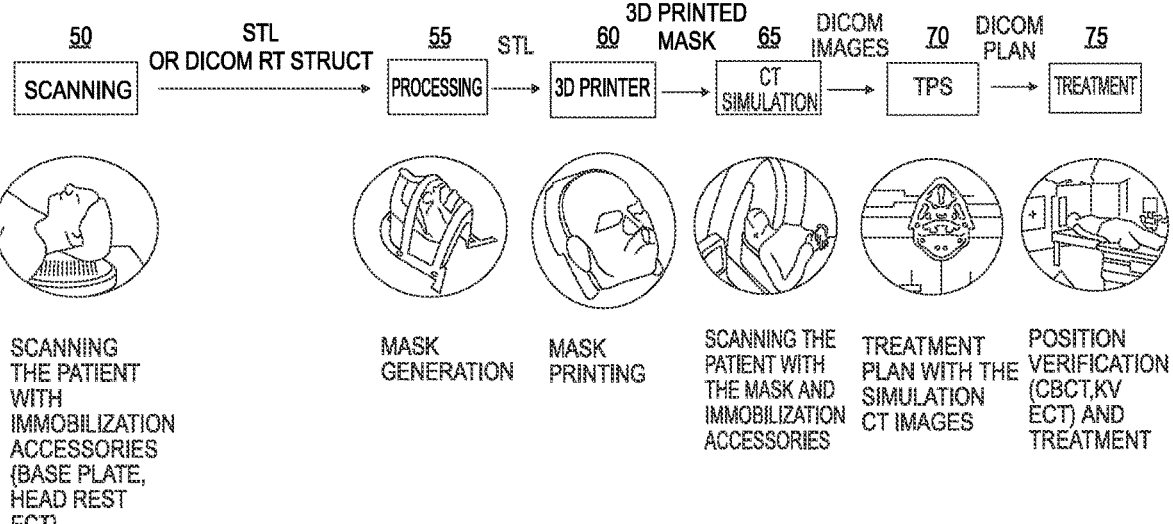
FIG. 2 schematically illustrates an example method of generating a patient-customized immobilization structure using patient-specific surface data.

Referring now to FIG. 2, an example workflow is illustrated that shows a series of steps that can be performed to generate a digital model of a patient-specific immobilization structure based on the processing of surface data associated with an exposed surface of the body portion of the patient that is to be immobilized during a medical procedure, and subsequent steps involving the fabrication and example use of the patient-specific immobilization structure.

As shown at step 50, image data is initially acquired that is suitable for characterizing an exposed surface of the body portion that is to be immobilized during the medical procedure. During this image data acquisition step, the body portion of the patient is supported in a fixed position and orientation by a support structure (e.g. via contact of the body portion with the support structure). The image data that is acquired while the body portion is supported by the support structure may be surface image data that directly characterizes the exposed surface of the body portion. Alternatively, the acquired image data may be volumetric image data that can be processed to generate surface image data characterizing the exposed surface of the body portion (e.g. computed tomography (CT) or magnetic resonance (MRI) volumetric image data).

Figure 3:
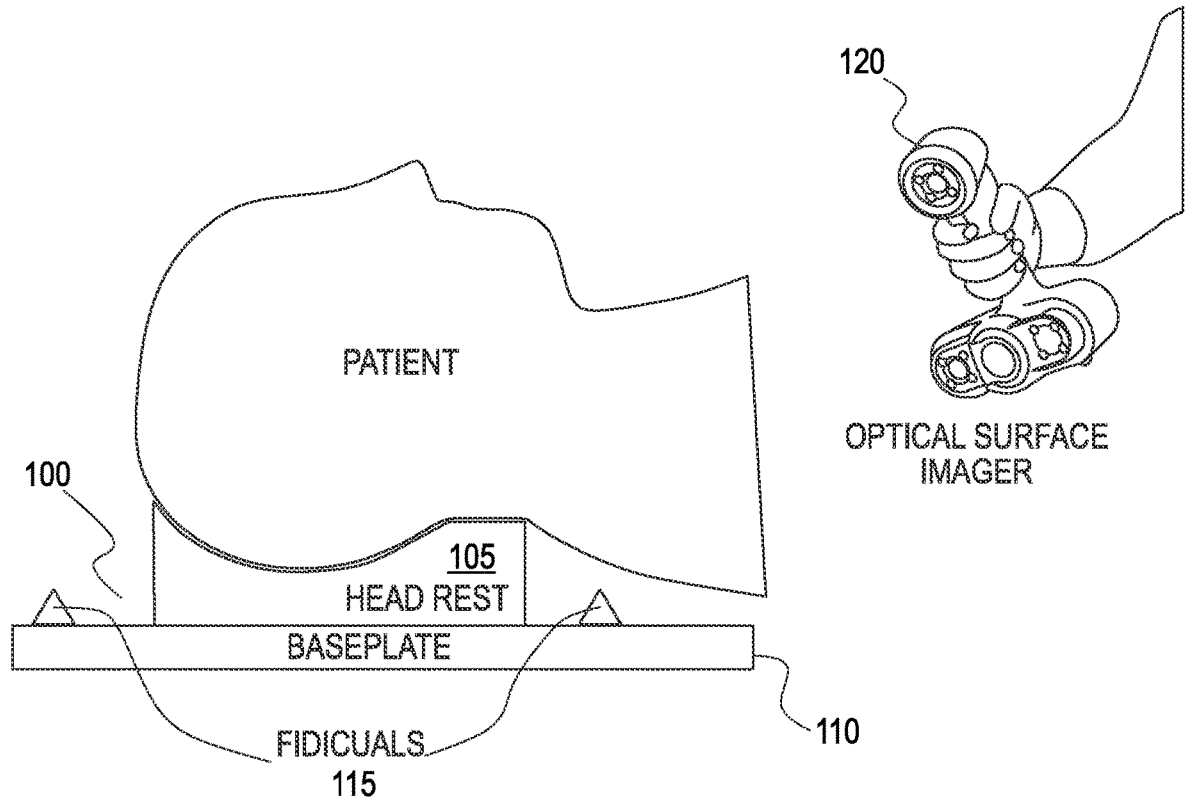
FIG. 3 illustrates an example method in which a surface scanning device is employed to obtain surface data characterizing an exposed surface of a body portion of the patient and a portion of a support structure on which a body portion of the patient rests.

An example implementation of the initial image data acquisition step is illustrated in FIG. 3, which shows the head of a patient supported on a support structure 100 while the patient resides in a supine position. The example support structure 100, which includes a headrest 105 and a baseplate 110, is used both during the initial image data acquisition step and during the medical procedure. In the example implementation shown in the figure, the exposed anterior-facing surface of the head is scanned using a handheld optical surface detection device 120 while the head is supported by the headrest 105 on the baseplate 110. It will be understood that the support structure shown in the figure is but one example of many different support structure configurations, as described in further detail below.

The support structure may include one or more features (not shown in FIG. 3) that enable the support structure to be fixed (anchored) in a prescribed position and orientation relative to a diagnostic or therapeutic system or a component or subsystem of such a system, such as a patient table that is moveable relative to a gantry of a diagnostic or therapeutic system. For example, the support structure may be shaped and/or have attachment or anchoring features (e.g. pins, tabs, slots, holes) that enable the removable attachment (anchoring) of the support structure to a component of a diagnostic or therapeutic system.

Referring again to FIG. 2, in step 55, surface data that characterizes the exposed surface of the supported body portion (either directly acquired with a surface imaging device or obtained by processing volumetric image data) is employed to generate a digital model of a patient-specific immobilization device. However, the present inventors realized that such surface data alone is insufficient to generate a patient-specific immobilization device that is capable of immobilizing the body portion in the same position and orientation, relative to the support structure, that was employed during the initial image data acquisition step.

Indeed, if surface data characterizing only the exposed surface of the body portion is employed to generate a patient-specific immobilization device, the absence of any information regarding the position and orientation of the support structure during the initial image data acquisition step, relative to a frame of reference associated with the acquired image data, precludes the ability to generate a digital model of a patient-specific immobilization device that uniquely attaches or otherwise engages with the support structure to accurately immobilize the body portion, relative to the support structure, in the same position and orientation that was employed during the initial image data acquisition step. In other words, while it would be possible to employ the surface data characterizing the exposed surface of the body portion to generate a digital model of a mask that conforms to the exposed surface of the body portion, such a mask would inherently be absent of any spatial features that facilitate engagement and attachment with the support structure, and would therefore not facilitate the generation of a patient-specific immobilization structure that is capable of immobilizing the body portion between the immobilization structure and the support structure, with the body portion in the position and orientation, relative to the support structure, that was employed during the initial image data acquisition step.

The present inventors realized that if additional spatial information is obtained that relates the position and orientation of the support structure relative to the acquired image data during the initial image data acquisition step, then this additional spatial information may be employed, when generating the digital model of the patient-specific immobilization device, to configure the patient-specific immobilization device such that it is capable of uniquely attaching or otherwise engaging with the support structure to accurately immobilize the body portion, relative to the support structure, in the position and orientation that was employed during the initial image acquisition step.

Accordingly, many example embodiments of the present disclosure employ additional spatial data or spatial information facilitating a determination of the position and orientation of the support structure relative to the acquired image data (e.g. in a frame of reference or coordinate system associated with the acquired image data) during the initial image data acquisition step. It will be understood that the additional spatial information that relates the position and orientation, during the initial image data acquisition step, of the support structure relative to the acquired image data, may be obtained according to a wide variety of example embodiments and implementations.

In some example embodiments, the imaging device employed for image acquisition may have a field of view sufficient for also imaging at least a portion of the support structure that is employed to support the body portion during the initial image data acquisition step, such that the collected image data is also sufficient to characterize at least a portion of the support structure. In such a case, since the image data obtained during the initial image data acquisition step characterizes both (i) the exposed surface of the body portion that is to be immobilized and (ii) at last a portion of the support structure, the position and orientation of the support structure relative to the exposed surface of the body portion can be determined. For example, known spatial features of the support structure may be employed to process the image data and determine the position and orientation of the support structure in the frame of reference of the image data.

Accordingly, in some example embodiments, the image data acquired during the initial image data acquisition step may be processed to (i) determine a position and orientation of the support structure based on one or more known spatial features of the support structure, in a frame of reference of the acquired image data, and (ii) segment surface data associated with the exposed surface of the body portion, thereby obtaining segmented patient surface data. Such a method is illustrated in steps 200-215 of the example flow chart shown in FIG. 4.

It will be understood that a wide variety of methods may be employed to process the image data for the determination of the position and orientation of the support structure based on the one or more known spatial features of the support structure. The spatial features may include fiducial features, for example, as illustrated in FIG. 3 which shows fiducials 115 residing on an exposed upper surface of the baseplate 110. The spatial features may include structural features such as one or more corners, protrusions, barcodes, glyphs, alignment features and attachment features. Fiducial features may be passive (e.g. reflective) or active (e.g. light emitting or electromagnetic). These spatial features may be defined in a digital model characterizing at least a portion of the support structure. In some example implementations, a user interface may facilitate the selection of one of several pre-defined support structure models. In the case of a support structure that includes a baseplate and an anatomical support (such as a headrest), the spatial features that are employed to determine the location and orientation of the support structure may reside only in or on the baseplate, only in or on the anatomical support, or in/on both the baseplate and the anatomical support. For example in the case of a support structure that includes a baseplate portion and a headrest portion, one or more spatial features (e.g. fiducials) may be integrated with the headrest (e.g. ball bearings or reflective markers that are secured to the headrest).

For example, this selection may involve the location of a set of reflective markers in the case of optical imaging, or high-density/atomic number ball bearings, high-contrast wires or pins in the case of CT imaging, regions of contrast media eliciting high T1 or T2 signal in the case of MRI imaging, or sources containing gamma-emitting radiation in the case of PET or SPECT imaging. Alternatively, a set of features, e.g., edges, surfaces, corners, pins, knobs, holes or features in a mesh region already included in the support structure may be detected manually or automatically.

Non-limiting example methods for processing the image data for the determination of the position and orientation of the support structure based on the one or more known spatial features of the support structure include thresholding algorithms and template matching algorithms.

Likewise, a wide variety of methods may be employed to obtain the segmented patient surface data by segmenting the image data. For example, reflective markers give a high signal in optical imaging and may be readily identified. High-contrast markers in CT will provide a high Hounsfield unit relative to surrounding materials and therefore can be identified either manually or automatically, e.g., by thresholding the image data. A similar approach would be possible in other modalities such as MRI or nuclear medicine imagine (PET or SPECT) where the fiducial marker gives a distinct signal relative to the signal of the proximal, surrounding regions of the support structure.

A non-limiting example method for processing the image data to segment the image data to obtain the segmented patient surface data includes defining a volume of interest surrounding the surface to eliminate extraneous data, ii) thresholding (either manual threshold or determining gradient from air to tissue), and iii) postprocessing, e.g., keeping the one largest part, smoothing the surface, closing holes, either real (nasal passages, outer ear canal) or defects due to missing data. For example, in the example case of the body portion being the head, the position of the cranium could be easily detected or known a priori. In one example implementation, a median lateral separation of the cranium may be employed (e.g. 15 cm) to determine a suitable volume of interest, at least as a first step, to eliminate extraneous image data (e.g. extraneous image data that may otherwise complicate the surface segmentation).

In other example implementations, one or more sensors that are integrated with the support structure may be employed to determine and/or confirm the position and orientation of the support structure relative to the body portion of the patient. For example, one or more sensors could be integrated with (e.g. built into the surface of) the support structure (e.g. a baseplate or headrest portion of the support structure), such as one or more linear arrays of sensor. Such sensors could be employed to determine the position of the body portion above relative to a region or reference location of the support structure (e.g. relative to a surface of a baseplate portion of the support structure). Non-limiting examples of sensors include infrared transmitters/receivers, acoustic transmitters/receivers, thermal sensors, and/or capacitive detectors (i.e. a sensor may include an emitting component and a receiving/detecting component). For example, in some example implementations, lateral and superior detectors could be employed to provide signals that can be processed to determine the position and orientation of the body portion relative to the support structure. In some example implementations, proximity sensors, such as optical, sonic, ultrasonic, or capacitive proximity sensors, could be employed to determine the position and orientation of the occipital portion of the cranium relative to a baseplate or other region of the support structure.

Figure 4:
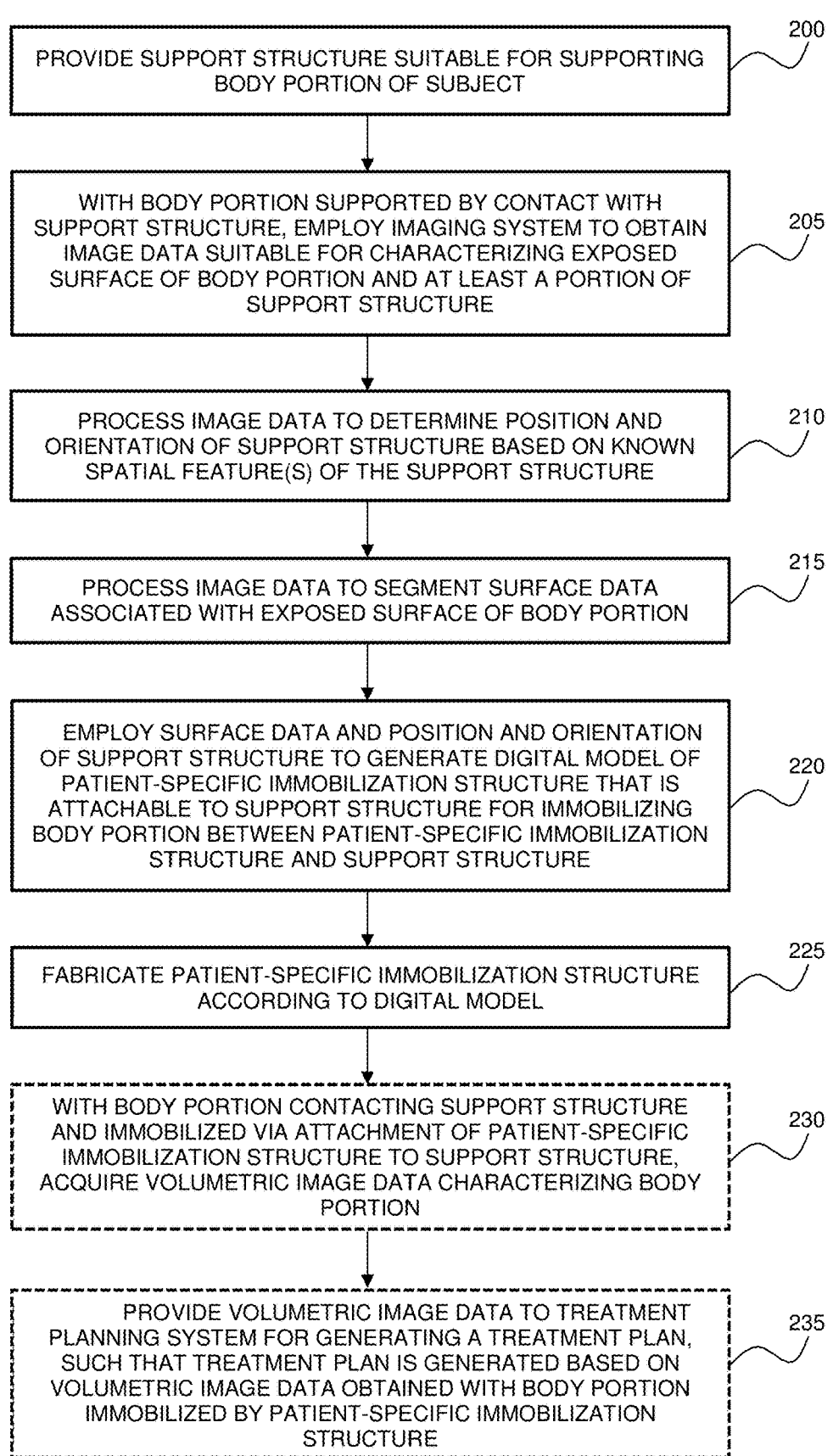
FIG. 4 is a flow chart illustrating an example method of generating a patient-customized immobilization support using patient-specific surface data.

Referring again to step 60 of FIG. 2 and step 220 of FIG. 4, having determined the position and orientation of the support structure within or relative to the frame of reference of the image data, the known position and orientation of the support structure relative to the segmented patient surface data may be employed to design and fabricate a patient-specific immobilization structure that is capable of engaging with the support structure in a unique and spatially-registered configuration such that the body portion is immobilized between the patient-specific immobilization structure and the support structure in the position and orientation, relative to the support structure, employed during the initial image data acquisition step. In other words, the patient-specific immobilization structure may be configured such that it is capable of engaging with the support structure in a unique and spatially-registered configuration, such when the body portion is supported by the support structure and the patient-specific immobilization structure is placed over the body portion, aligned with the support structure and attached (connected) to the support structure, the body portion is securely immobilized between the patient-specific immobilization structure and the support structure, with at least a portion of the surface of the body portion that was exposed during the initial image data acquisition step residing conformally adjacent to an inner surface of the patient-specific immobilization structure, and with the body portion being supported, relative to the support structure, in the same configuration that was employed during the initial image data acquisition step.

It will be understood that various methods may be employed to generate the digital model of the patient-specific immobilization structure that facilitates the aforementioned unique and spatially registered alignment and engagement with the support structure. In one example implementation, one or more peripheral regions of the segmented patient surface data may be digitally extended (e.g. digitally extruded) to form one or more features or structures that facilitate the alignment and engagement of the patient-specific immobilization structure with the support structure in a configuration suitable for immobilizing the body portion between the patient-specific immobilization structure and the support structure in the position and orientation, relative to the support structure, employed during the initial image data acquisition step. Example methods of digital extension for alignment/attachment are described in detail below.

In one example implementation, the patient-specific immobilization structure may include one or more alignment features that are configured to contact corresponding features of the support structure when the patient-specific immobilization structure is aligned with the support structure for immobilizing the body portion between the patient-specific immobilization structure and the support structure. Non-limiting examples of alignment features include mating features such as a pin and hole or a tab and a slot. Another example of a structural feature that facilitates alignment of the patient-specific immobilization structure with the support structure is a flange that is configured to contact a respective surface of the support structure when the position and orientation of the support structure, relative to the patient-specific immobilization structure, matches the relative position and orientation that was present during the initial image data acquisition step.

The patient-specific immobilization structure may include one or more attachment features that facilitate attachment of the patient-specific immobilization structure with the support structure when the patient-specific immobilization structure is aligned with the support structure. Non-limiting examples of attachment features include one or more locking pins that are insertable into corresponding receiving holes or slots within the support structure, and other example devices such as latches, rotating tabs, clamps, ball-socket features, snaps, hook and loop fasteners, optionally in conjunction with alignment pins.

In some example implementations, one or more features of the patient-specific immobilization structure may facilitate both alignment and attachment with respective features of the support structure.

The positions and configurations of the alignment and/or attachment features of the patient-specific immobilization structure may be digitally generated based on known locations of corresponding features of the support structure (e.g. according to a known digital model characterizing at least a portion of the support structure).

Referring now to step 60 of FIG. 2 and step 225 of FIG. 4, the digital model of the patient-specific immobilization structure (optionally modified as described below) may then be employed to fabricate the patient-specific immobilization structure. While a wide variety of methods and fabrication devices may be employed for fabrication, in some example implementations, a three-dimensional printer (additive manufacturing device) can be employed to fabricate the patient-specific immobilization structure from the digital model. In other example implementations, other fabrication methods and devices may be employed to fabricate the patient-specific immobilization structure from the digital model, such as, but not limited to, subtractive manufacturing, such as milling and plastic vacuum forming.

The fabricated patient-specific immobilization structure may be employed to immobilize the body portion of the patient during the medical procedure, as shown at step 75 of FIG. 2. As described above, the patient-specific immobilization structure includes features that facilitate the unique alignment and attachment to the support structure such that the body portion of the patient is immobilized in the same position and orientation, relative to the support structure, that was employed during the initial image acquisition step.

It will be understood that there are a wide range of potential workflows or post-fabrication methods involving use of a patient-specific immobilization structure fabricated according to the present example embodiments. For example, a second image acquisition step may be employed to obtain volumetric image data characterizing the body portion when the body portion is immobilized between the fabricated patient-specific immobilization structure and the support structure, as illustrated in optional step 65 of FIG. 2, and as shown in optional step 230 of FIG. 4. This volumetric image data may then be employed to generate a treatment plan, as illustrated in optional step 70 of FIG. 2, and as shown in optional step 235 of FIG. 4. This treatment plan, generated based on the presence of the fabricated patient-specific immobilization structure, may subsequently be employed for the medical procedure. This example workflow is beneficial in that it can significantly reduce the time delay prior to treatment, reduce utilization of imaging systems and free up imaging resources for other patients and procedures, and reduce exposure of the patient to ionizing radiation (e.g. in the case of CT imaging).

In an alternative example implementation, steps 65 and 70 of FIG. 2 and steps 230 and 235 of FIG. 4 may be omitted. For example, if the initial image data that was acquired in step 50 of FIG. 2 and step 205 of FIG. 4 is volumetric image data, this initial volumetric image data may be employed to generate a treatment plan, since the patient-specific immobilization structure is configured to immobilize the body portion of the patient in the same position and orientation, relative to the support structure, as during the initial image data acquisition step.

In yet another example workflow, the image data may be employed to generate an initial (preliminary) treatment plan, and steps 65 and 70 of FIG. 2 and steps 230 and 235 of FIG. 4 may be employed to refine or confirm the treatment plan based on secondary volumetric image data acquired in the presence of the fabricated patient-specific immobilization structure. In the example case of preliminary treatment planning for radiotherapy procedures, non-limiting examples of pre-planning steps or operations performed with a treatment planning system include beam placement and/or definition of location of a bolus.

In cases in which the initially acquired image data is employed to formulate a preliminary or final treatment plan, it may be necessary to pre-process the initially acquired image data in order for it be provided in a form that is compatible with a given treatment planning system. For example, many current treatment planning systems are designed to accept imaging data in a CT format to initiate the treatment planning process. For example, MRI image data can be converted to a 'synthetic' CT prior to import into the treatment planning system. For example, conversion algorithms presently exist that are capable of converting MRI signals to Hounsfield units.

Furthermore, even in cases in which the initially acquired image data is surface image data, for example, surface data acquired with an optical surface scanning system, such surface data can be processed and converted into a "synthetic" CT image format prior to import into the treatment planning system, where the conversion process employs a model to generate synthetic volumetric image data within the surface characterized by the surface image data. For example, the model may generate the internal image data based on the assumption of unit density inside the closed surface.

Figure 5A:
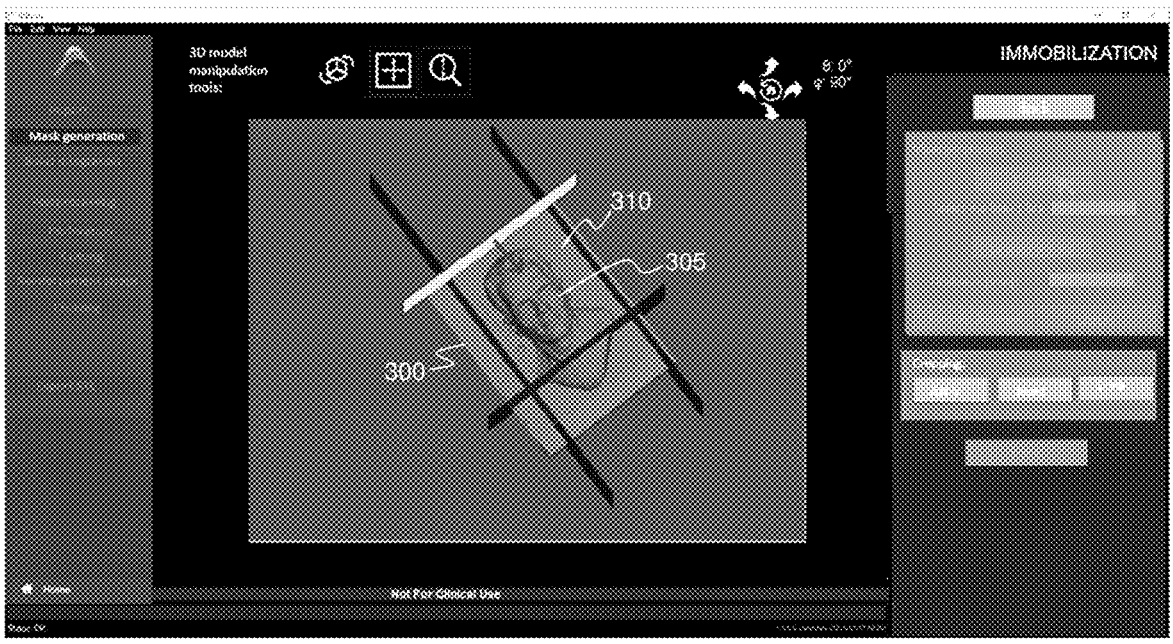
FIGS. 5A-5G illustrate an example method and user interface for generating a digital model of a patient-customized immobilization structure using patient-specific surface data.

Referring now to FIGS. 5A-5F, a user interface is shown that facilitates the generation of a digital model of the patient-specific immobilization structure based on acquired surface image data. FIG. 5A shows a user interface window facilitating the cropping of a subregion of the surface image data 300 for further processing. As can be seen in the figure, the surface image data 300 includes patient surface data 305 characterizing an exposed surface of the body portion of the patient, and additional surface data 310 beyond the patient anatomy that includes surface features associated with the support structure.

Figure 5B:
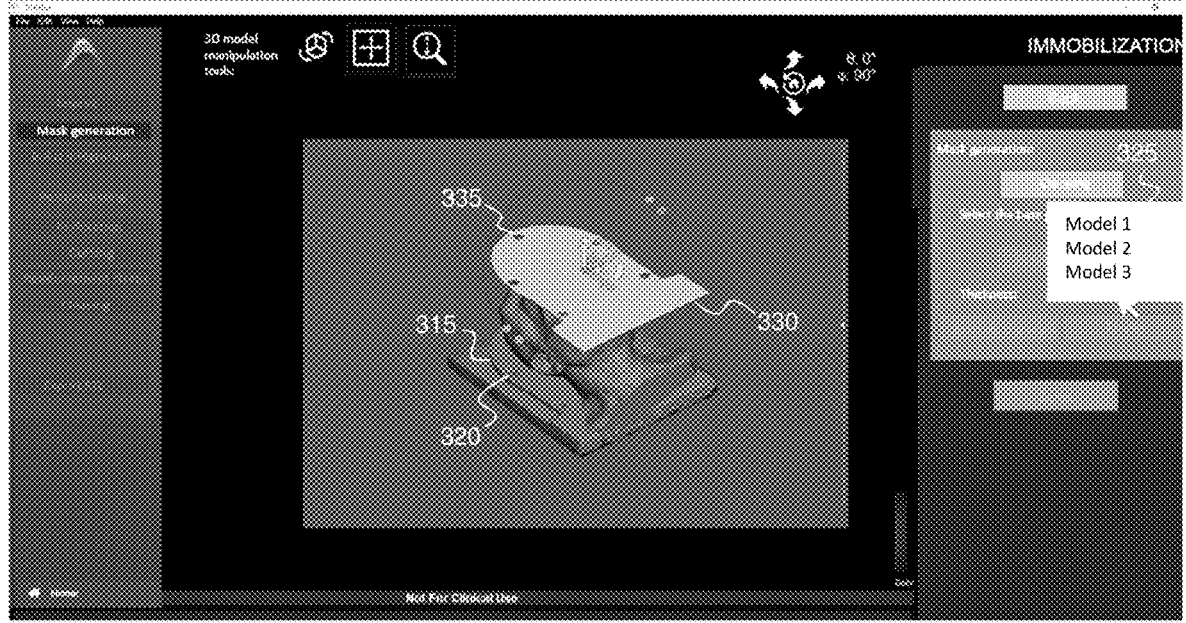
Figure 5C:
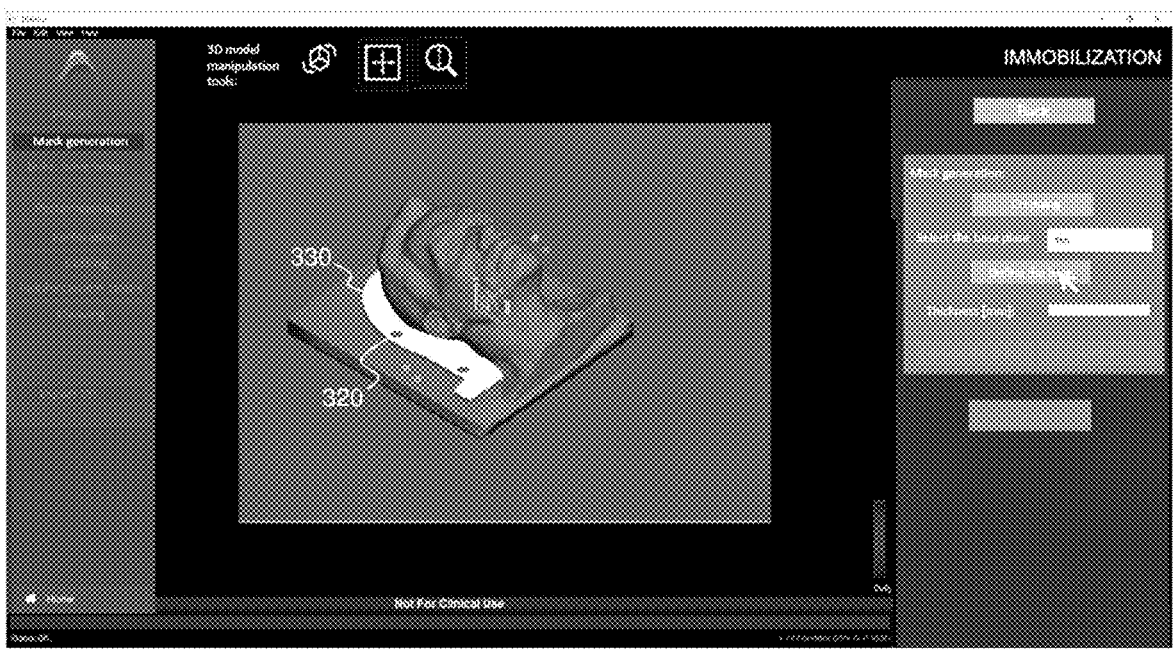

The cropped region of the initial surface data is shown in FIG. 5B. This figure also clearly shows the surface features of the support structure, including an outline of a baseplate that includes a peripheral boundary feature 315 of the baseplate and attachment holes 320 defined in the baseplate. The example user interface provides a list of selectable pre-defined digital baseplate or frame models at 325, from which a digital baseplate or frame model may be selected to facilitate the detection of the position and orientation of the baseplate within the frame of reference of the surface image data. In the present example user interface, the selection of a digital baseplate model results in the generation of a corresponding frame that will form a portion of the digital model of the patient-specific immobilization structure and is configured to engage with and attach to the support structure. For example, as shown in FIG. 5C, the base plate digital model 330 includes holes 335 that align with respective holes 320 of the baseplate. The selectable baseplates may include commercially available baseplates and/or custom baseplates. In an alternative example implantation, a digital model of a frame having spatial features that register with corresponding features of the baseplate may be selected and employed, where the digital model of the frame will form a portion of the digital model of the patient-specific immobilization support (as described in further detail below). The spatial features of the digital model of the frame that correspond to those of the baseplate may be employed to determine the position and orientation of the baseplate and spatially register the digital model of the frame for alignment and engagement with the baseplate.

Figure 5D:
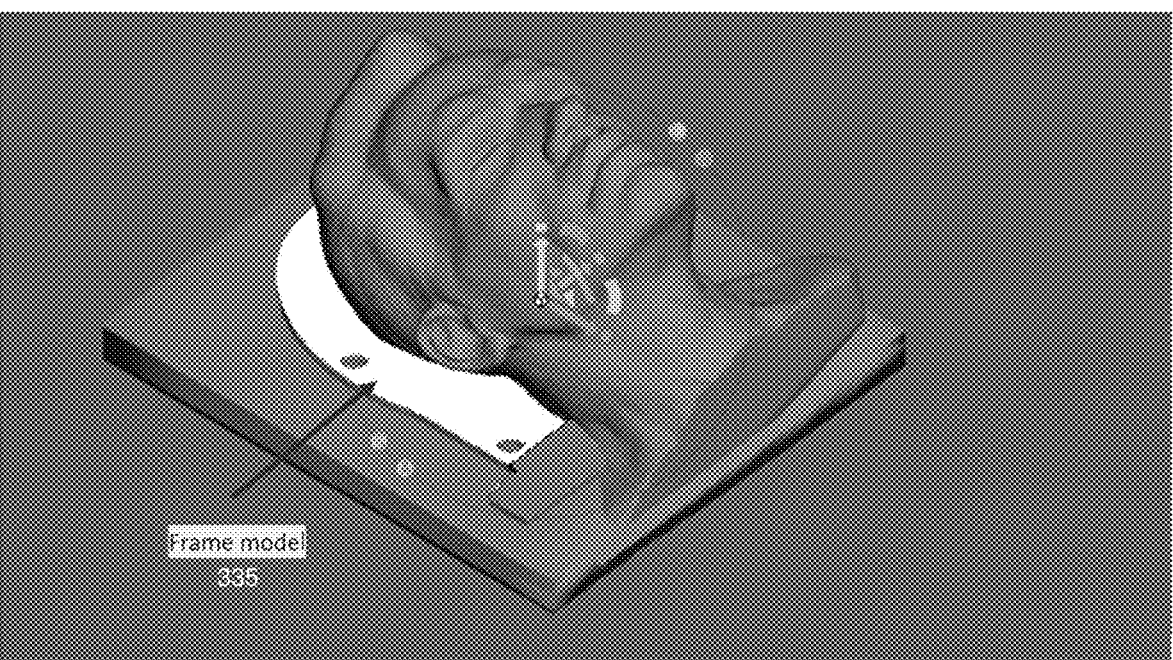

The surface image data is then processed to locate the position and orientation of the baseplate, as described above. FIG. 5C shows a subsequent example user interface view where the digital model of the base plate 335 is shown spatially aligned (spatially registered) with the corresponding features in the scanned baseplate. FIG. 5D. shows a digital model of a frame that corresponds to the selected base plate. As will be explained in further detail below, the frame 335 will serve as an alignment flange for spatially offsetting the patient-specific surface region of the digital model of the patient-specific immobilization structure relative to the support structure, and also includes alignment and attachment features (the holes 335) for aligning and securing the digital model of the patient-specific immobilization structure to the baseplate.

Figure 5E:

Having determined the position and orientation of the support structure within the frame of reference of the acquired surface data, the patient surface data may be segmented. FIG. 5E shows an example user interface view that displays the patient surface image data 305, and also shows the frame 335 at the location that is spatially registered with the identified location of the support structure.

Figure 5F:
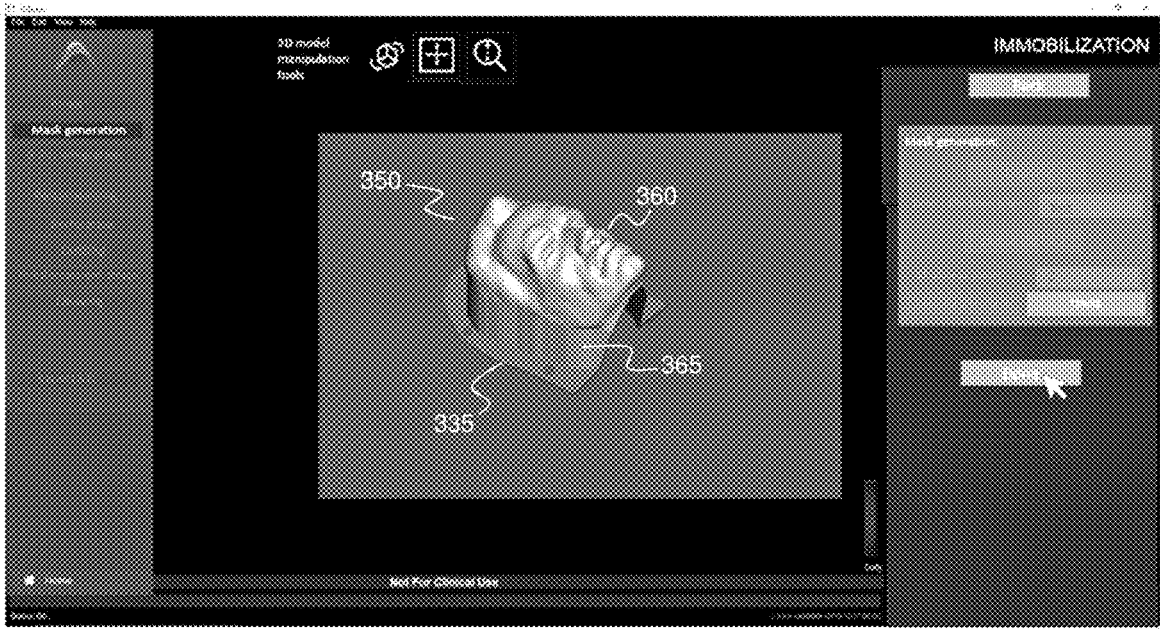

FIG. 5F is an example user interface view showing the generation of the digital model of the patient-specific immobilization structure 350 by employing the patient surface data to form a conformal shell region 360 that conforms to the exposed surface of the body portion and an extrusion region 365 that connects the conformal shell region 360 to the frame 335. As shown in the figure, the direction of extrusion may be determined to be perpendicular to the frame 335 (or perpendicular to a surface associated with the support structure).

Figure 5G:
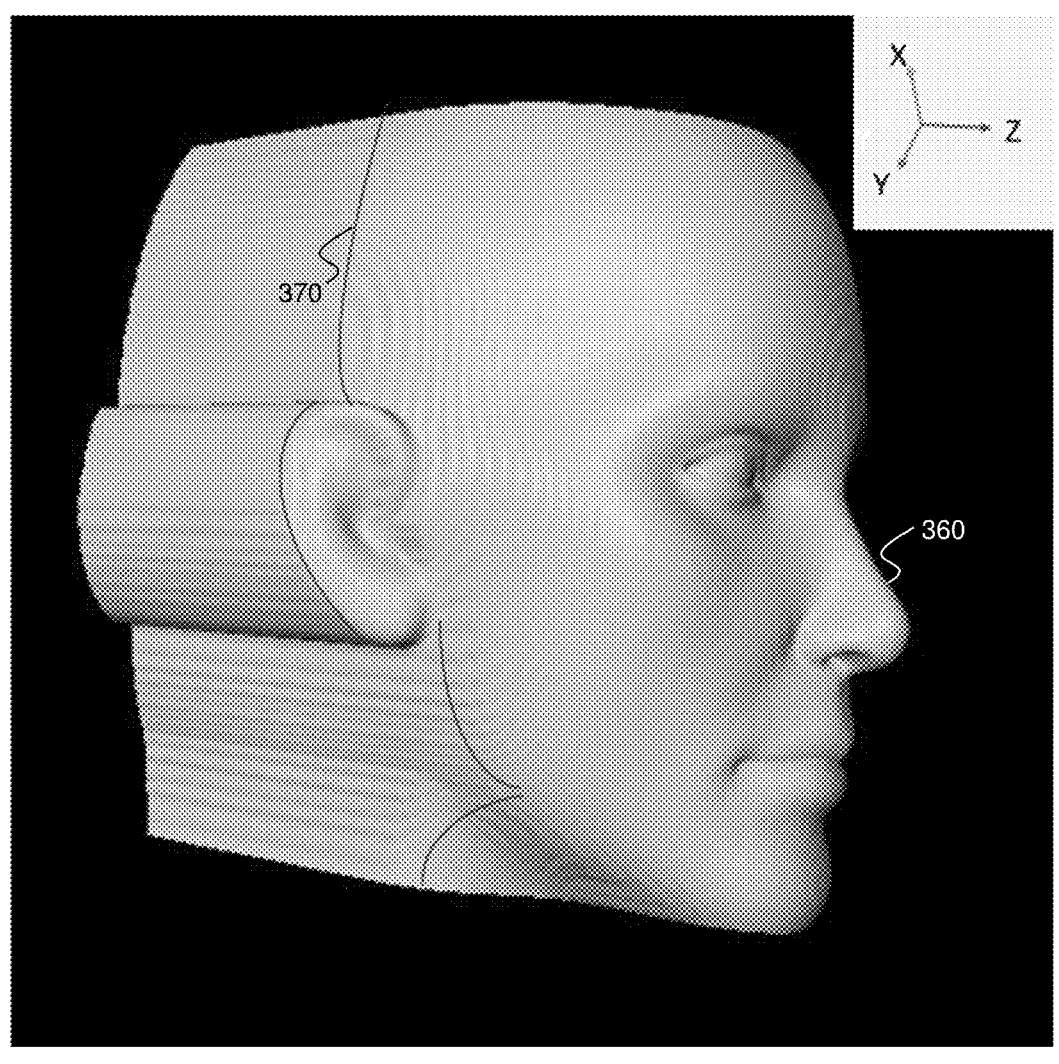

In some example implementations, peripheral region of the patient surface data from which extrusion is performed may be a non-planar contour. For example, at any superio-inferior location on the anatomy, the greatest lateral dimension may be variable with regard to anterioposterior plane. In other words, the extruded region must extend from the support device (or flange) to meet a curve on the surface of the patient-specific component, not a single plane. A patient-specific immobilization structure generated based on extrusion from a curved boundary, rather than from a plane, may be beneficial in ensuring that the patient-specific immobilization structure can be fitted on or over the patient, and may also be beneficial in facilitating removal of the patient-specific immobilization structure after its use. For example, as shown in FIG. 5G, in example implementations in which extrusion is performed from a planar portion (e.g. a frame or flange configured to engage with a baseplate) to a conformal shell region 360 generated based on the patient surface data, the patient-specific immobilization structure can be generated by performing extension or extrusion from a curved contour 370 in the direction perpendicular to frame (z).

Although many of the preceding examples refer to the use of a support structure having a baseplate, it will be understood that other implementations do not require a baseplate, provided that support structure has one or more features for anchoring relative to a diagnostic or treatment system (e.g. features that facilitate anchoring to a treatment couch).

Moreover, in example implementations involving a baseplate, the patient-specific immobilization structure need not engage and align directly with the baseplate and can instead engage and align with an intermediate structure extending from the baseplate, such as a frame or shell supported by the baseplate.

Figure 6A:
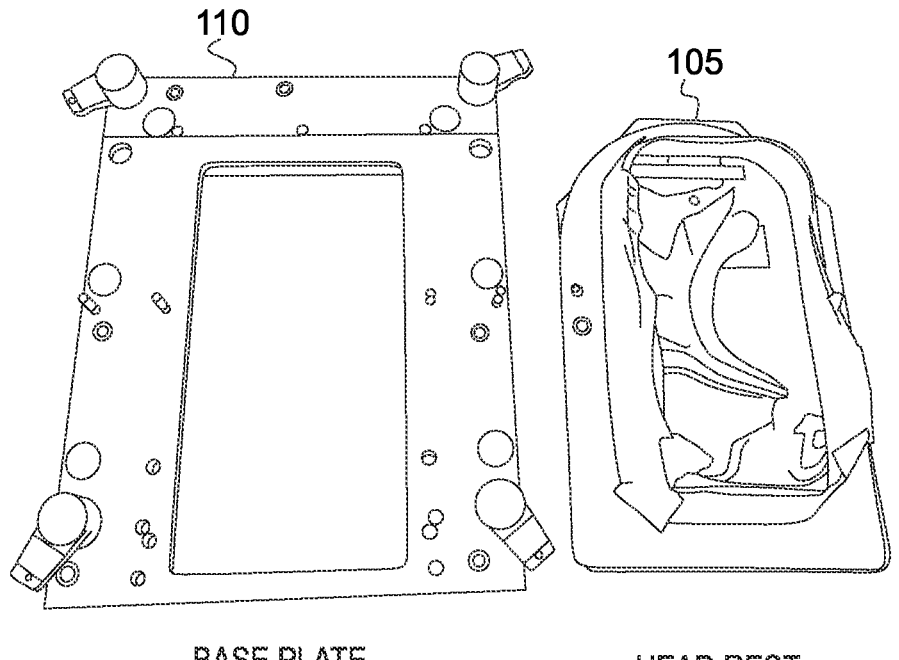
FIG. 6A is a photograph of an example base plate and an example headrest.
Figure 6B:
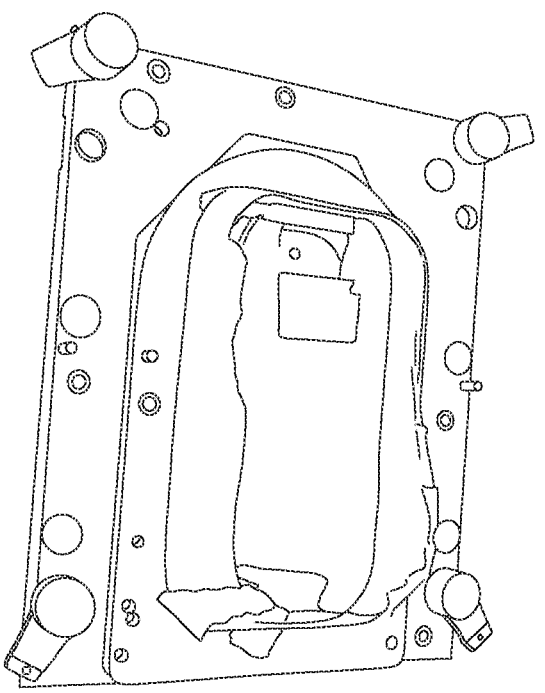
FIG. 6B is a photograph showing the headrest of FIG. 11A received in a prescribed position and orientation relative to the baseplate of FIG. 11A.

FIGS. 6A-6B, 7A-7B, 8A-8C, 9A-9B, 10A-10B and 11A-11E provide another example of the generation of a digital model of a patient-specific immobilization structure. FIG. 6A shows a photograph of the components of a support structure employed to support the head of the patient when performing initial image data acquisition. The support structure included a baseplate 110 and a head rest 105. As shown in FIG. 6B, the support structure is formed by securing the headrest to the baseplate in a prescribed orientation that is enforced by alignment pins in the baseplate and associated holes in the headrest.

Figure 7A:
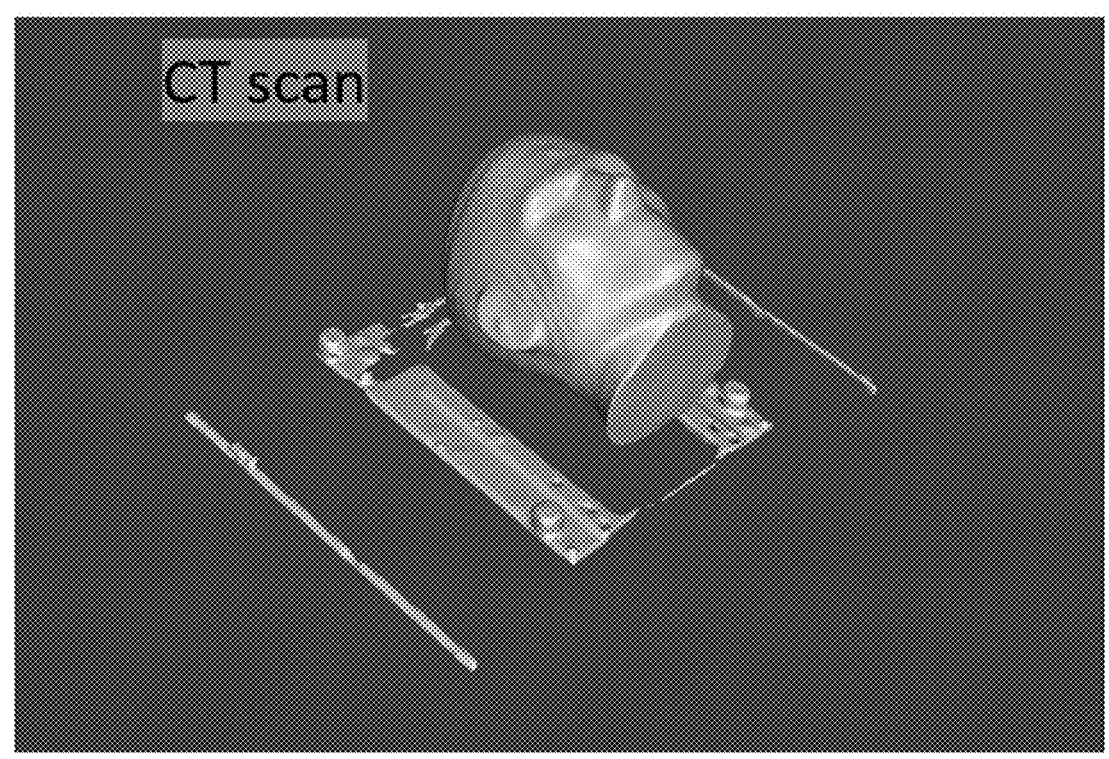
FIGS. 7A and 7B show surface data (i) segmented from computed tomography (CT) volumetric image data and (ii) acquired via optical surface scanning. The surface data characterizes both an exposed surface of the head of the patient and a portion of the baseplate employed to support the patient headrest.
Figure 7B:
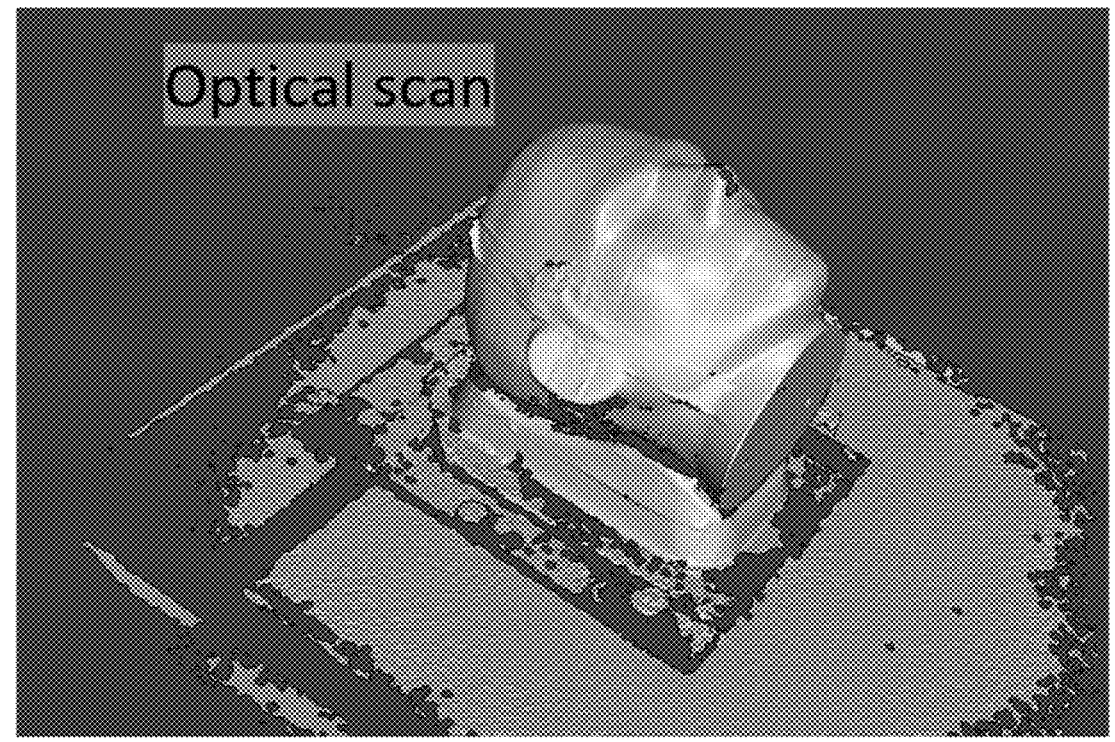

FIGS. 7A and 7B show two different example modalities for obtaining surface image data that characterizes both the exposed surface of the body portion and a portion of the support structure. FIG. 7A shows the surface data that is segmented from volumetric image data obtained from a CT scan (it is noted that only a portion of the baseplate was segmented, with the headrest being absent from the segmented surface data). As can be seen, the segmented surface data includes both surface data associated with the outer regions of the baseplate and surface data characterizing the exposed surface of the scanned body portion. FIG. 7B shows surface data that is directly obtained by scanning the patient and support structure with an optical surface scanning device. As in FIG. 7A, the surface data in FIG. 7B includes both surface data associated with the outer regions of the baseplate and surface data characterizing the exposed surface of the scanned body portion. In the remainder of the processing steps shown for the present example, the surface data segmented from the volumetric CT data is employed to generate the digital model of the patient-specific immobilization structure.

Figure 8A:
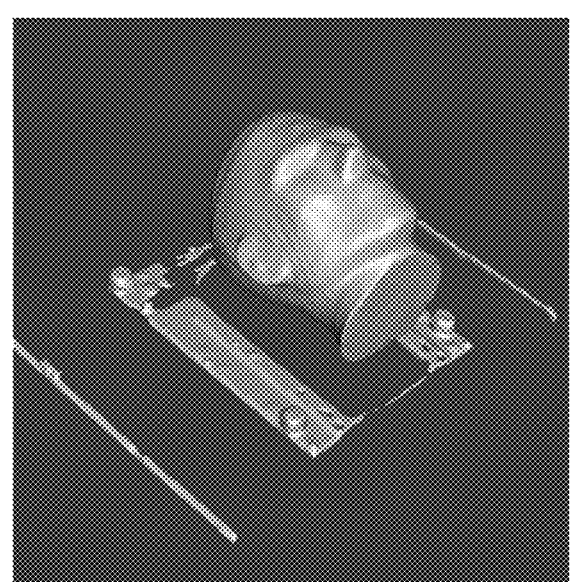
FIGS. 8A-8C illustrate the removal of extraneous background surface data from the acquired surface data.
Figure 8B:
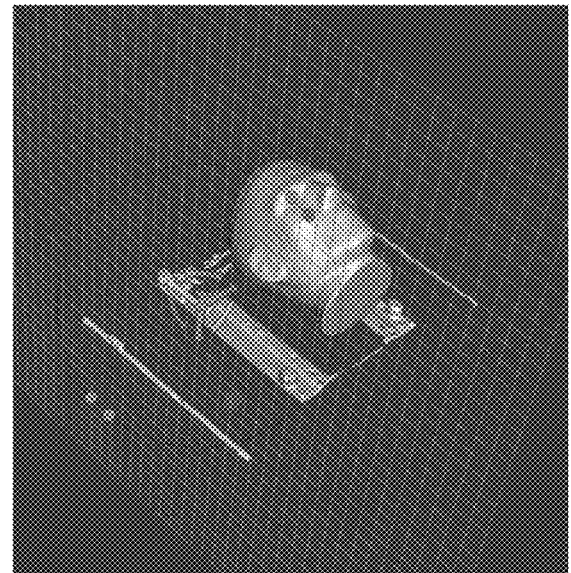
Figure 8C:
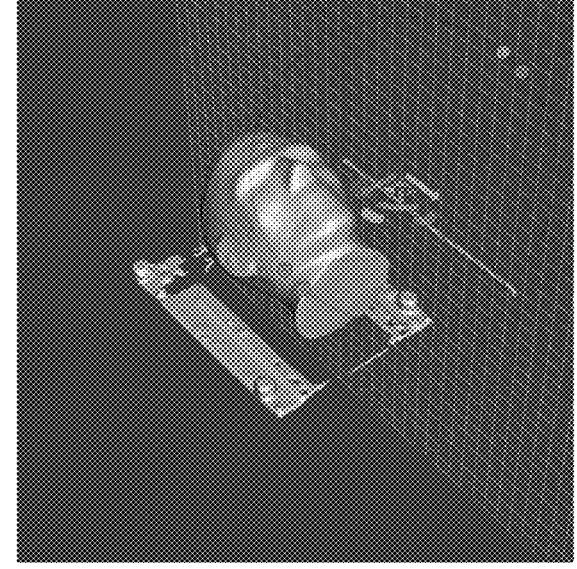

FIGS. 8A-8C illustrate the removal of extraneous background surface data from the acquired surface data. FIG. 8A shows the surface data segmented from the CT volumetric image data is shown prior to background removal. FIGS. 8B and 8C show the use of a cropping tool in a user interface window, where the leftmost background data has been removed in FIG. 8C.

Figure 9A:
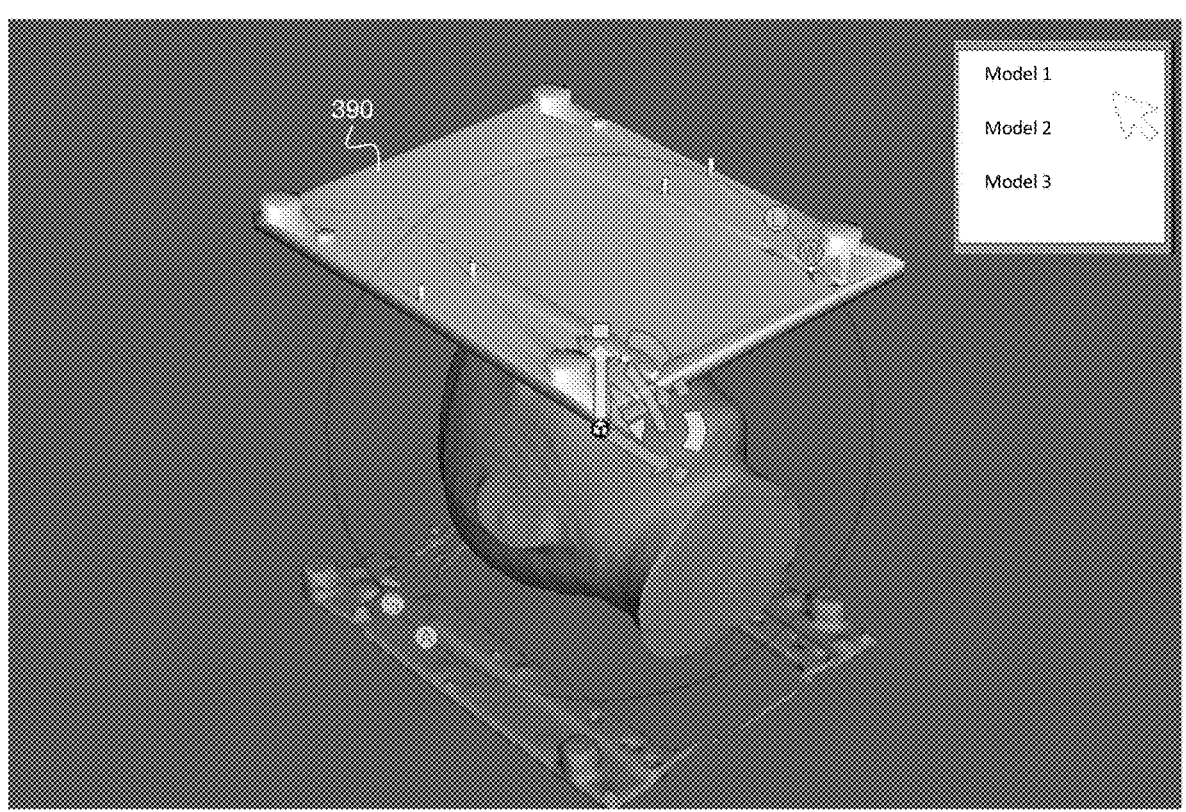
FIG. 9A illustrates an example method involving the selection of a baseplate model from a list of baseplate models for use during image segmentation.
Figure 9B:
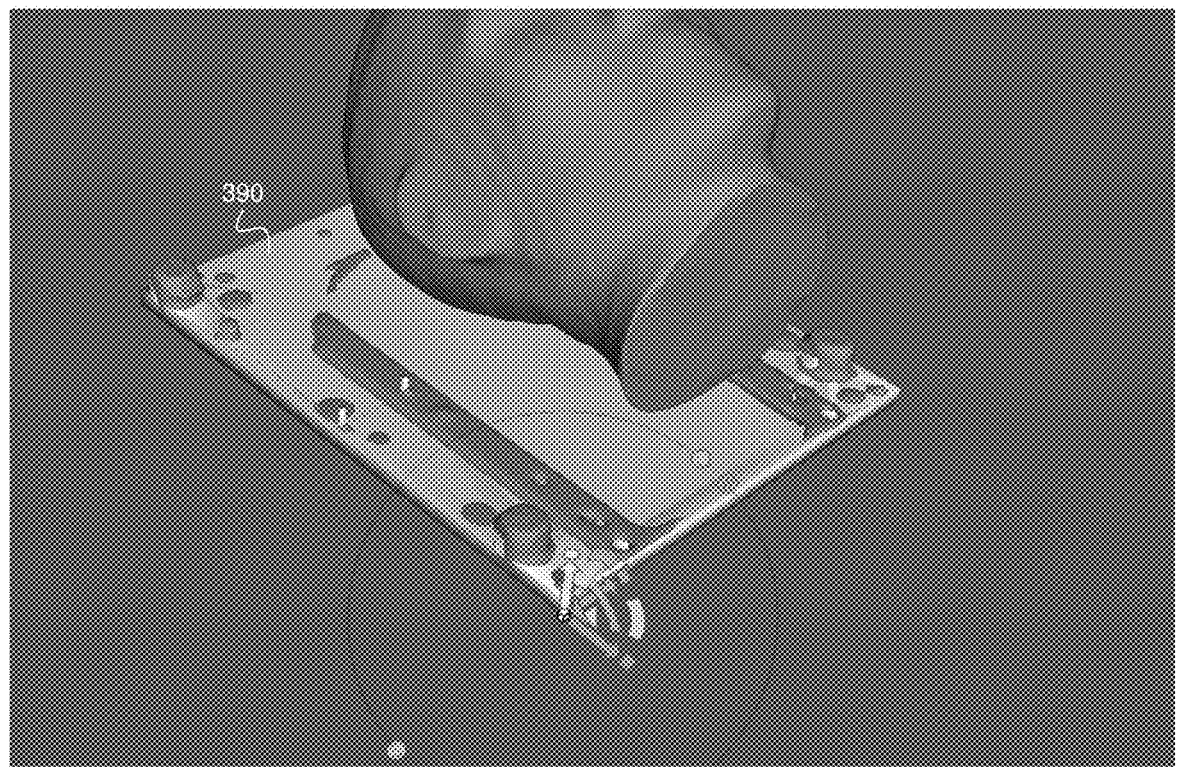
FIG. 9B illustrates the use of one or more spatial features of the selected baseplate to identity and localize of the baseplate within the surface image data.

In FIGS. 9A and 9B, a digital model of the baseplate 390 is selected in the user interface. The surface image data is processed and the digital model of the baseplate is employed to locate the position and orientation of the baseplate within the frame of reference of the surface image data. FIG. 9B shows the digital model of the baseplate 390 overlaid on the surface image data, demonstrating the successful determination of the position and orientation of the baseplate due to concordance of baseplate surface features in the surface image data and baseplate features in the digital model of the baseplate.

As can be understood from FIGS. 9A and 9B, the baseplate position and orientation may be automatically determined by performing registration between the digital model of the baseplate and the surface image data, or the baseplate position and orientation may be manually determined by positioning the digital model of the baseplate relative to the surface image data in a user interface until a sufficiently close spatial registration is observed. In some example implementations, an initial manual (visual) registration may be followed by an automated registration step to accurately determine the position and orientation of the baseplate.

Figure 10A:
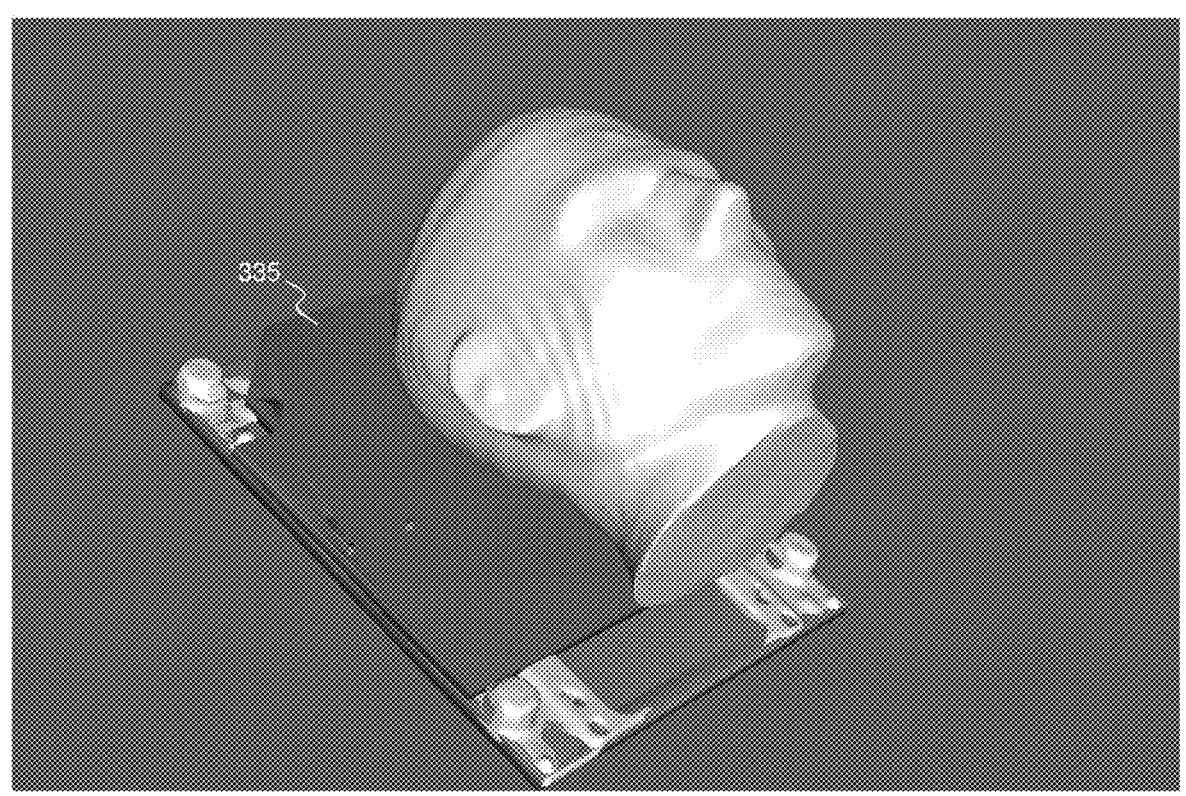
FIGS. 10A and 10B show the location of the localized baseplate relative to (i) the segmented surface data associated with the exposed surface of the body portion of the patient and (ii) a frame of the patient-specific immobilization structure that is spatially registered with the localized baseplate.
Figure 10B:
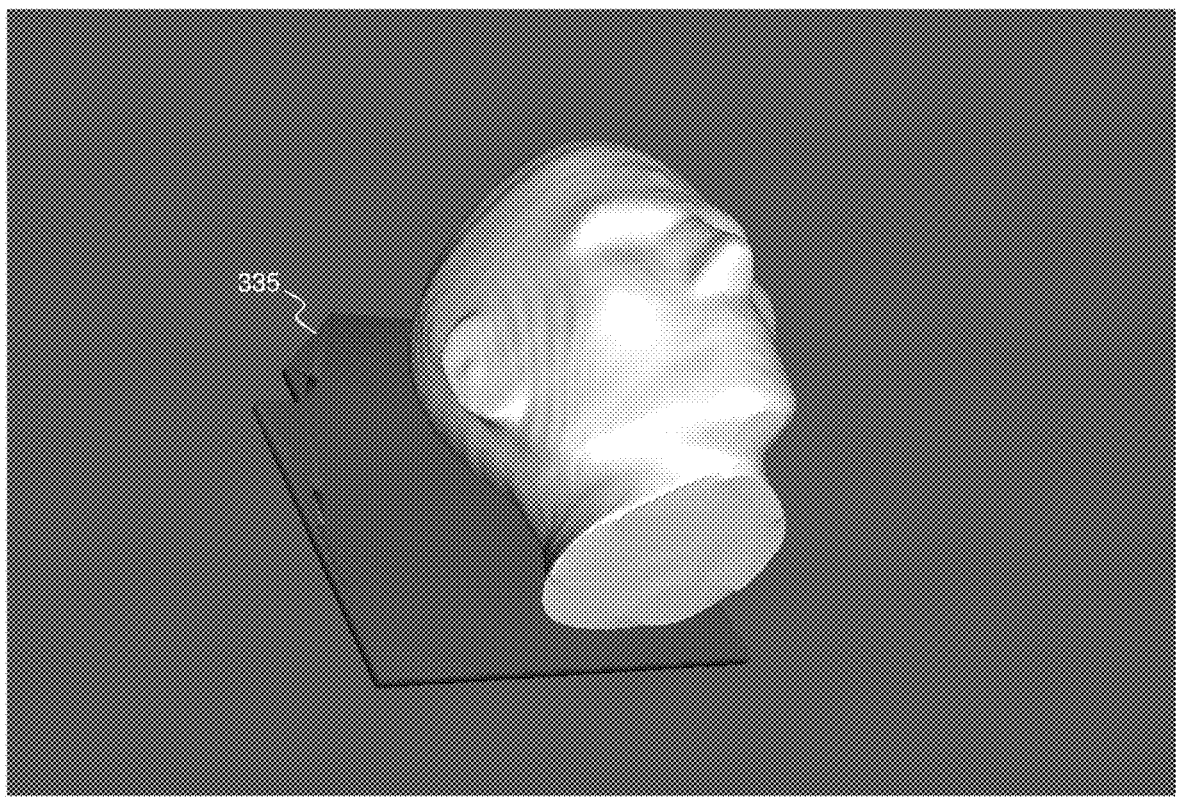

FIG. 10A shows the location of the localized baseplate relative to (i) the segmented surface data associated with the exposed surface of the body portion of the patient and (ii) the frame 335 of the patient-specific immobilization structure that is spatially registered with the localized baseplate. FIG. 10B shows only the segmented patient surface data and the frame 335 of the patient-specific immobilization structure (the determination of the baseplate position and location facilitates the segmentation of the patient surface data from the surface data associated with the baseplate).

Figure 11A:
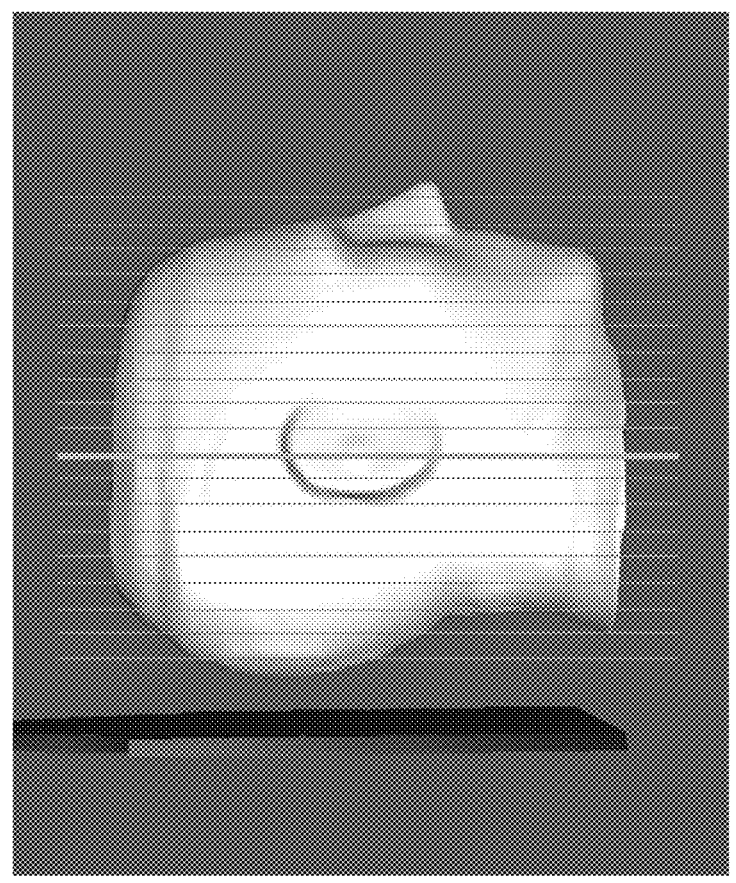
FIGS. 11A-11E illustrate an example method and user interface for generating a digital model of a patient-specific immobilization structure by performing extrusion of segmented surface data to the frame.
Figure 11B:
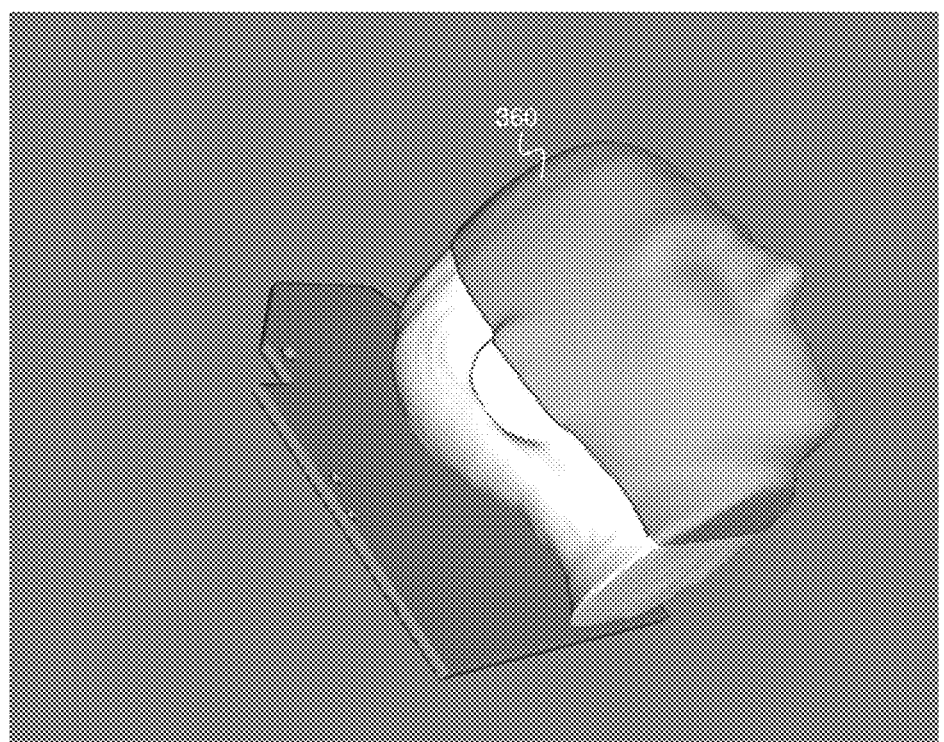
Figure 11C:
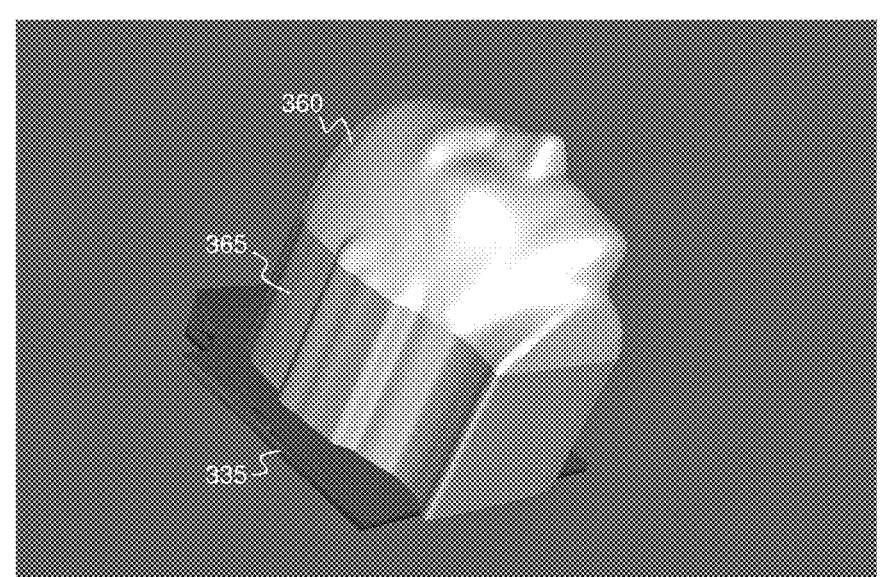

FIGS. 11A-11C demonstrate the generation of the patient-specific immobilization structure by the generation of a conformal shell region 360 that conforms to the exposed surface of the head and the generation of an extrusion region 365 extending from the conformal shell region 360 to the frame 335. As shown in FIG. 11A, in one example implementation, the conformal shell region 360 may have a perimeter region defined by a plane that is parallel to the frame 335 and bisects the body portion at its widest lateral extent (e.g. a plane defining the widest coronal cross section of the head of the patient.

Moreover, as described above, the extrusion may alternatively be performed based on a non-planar contour defined by the region of maximal extent (widest spatial extent in a direction perpendicular to the direction along which extrusion is performed.

Figure 11D:
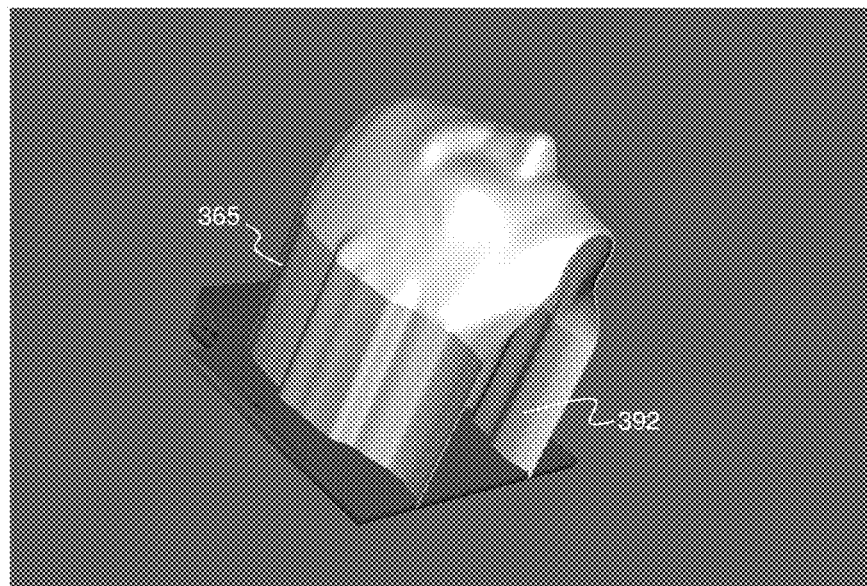
Figure 11E:
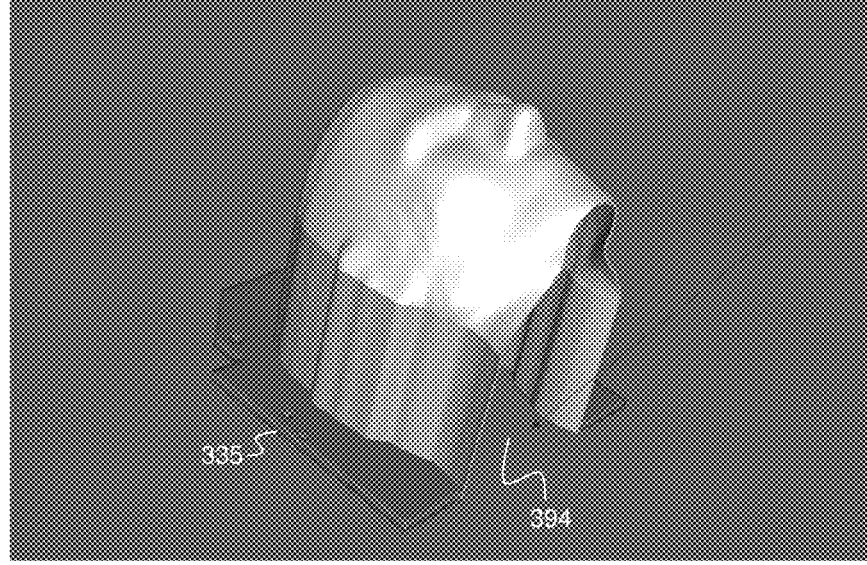

FIGS. 11D and 11E show the final steps in the generation of the digital model of the patient-specific immobilization structure by removal of a portion 392 of the extrusion region to accommodate the neck and a removal of back region 394 of the frame 335 to accommodate placement of the patient-specific immobilization structure over the body portion, merging the conformal shell region 360, the modified extrusion region 365, and the modified frame 335 to form the digital model.

As noted above, a significant potential benefit of the present method of generating a digital model of the patient-specific immobilization structure prior to its manufacture is the ability to perform modifications to the digital model of the patient-specific immobilization structure. Such modifications may be facilitated by a user interface that provides an operator with one or more selectable options for modifying the digital model of the patient-specific immobilization structure. Various example implementations of performing modification to the digital model of the patient-specific immobilization structure are illustrated in the example shown in FIGS. 12A-12D, 13A-13C, 14A-14E, 15A-15E and 16A-16B.

Figure 12A:
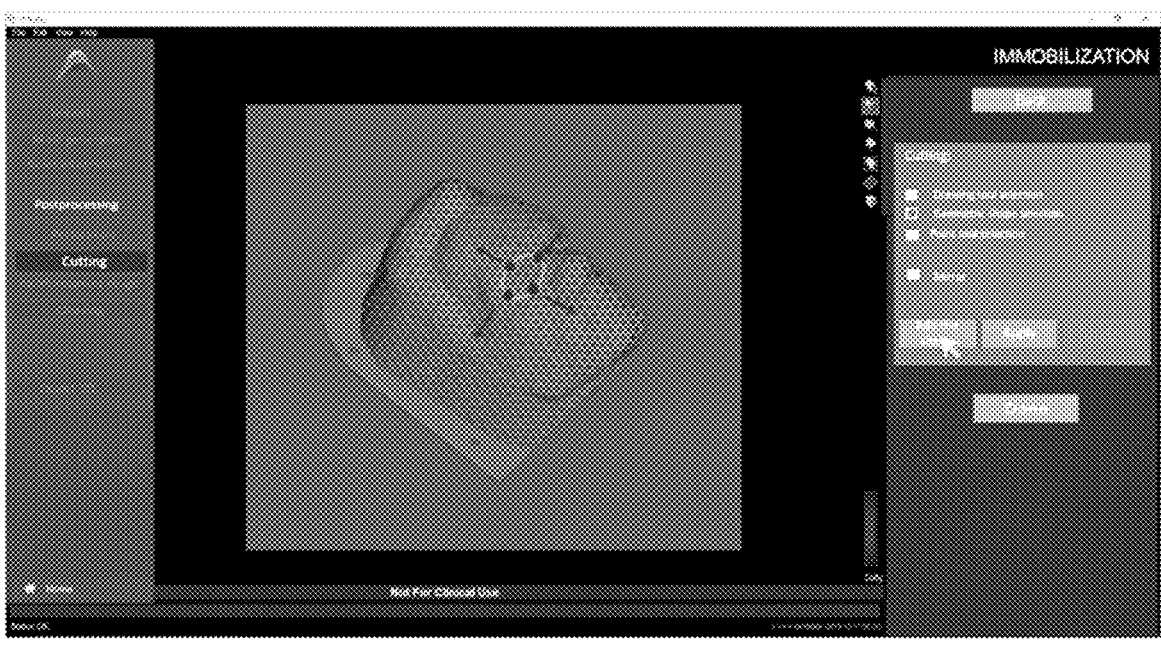
FIGS. 12A-12D illustrate an example method and user interface for modifying a digital model of a patient-customized immobilization structure to locally remove material in regions associated with facial features.
Figure 12B:
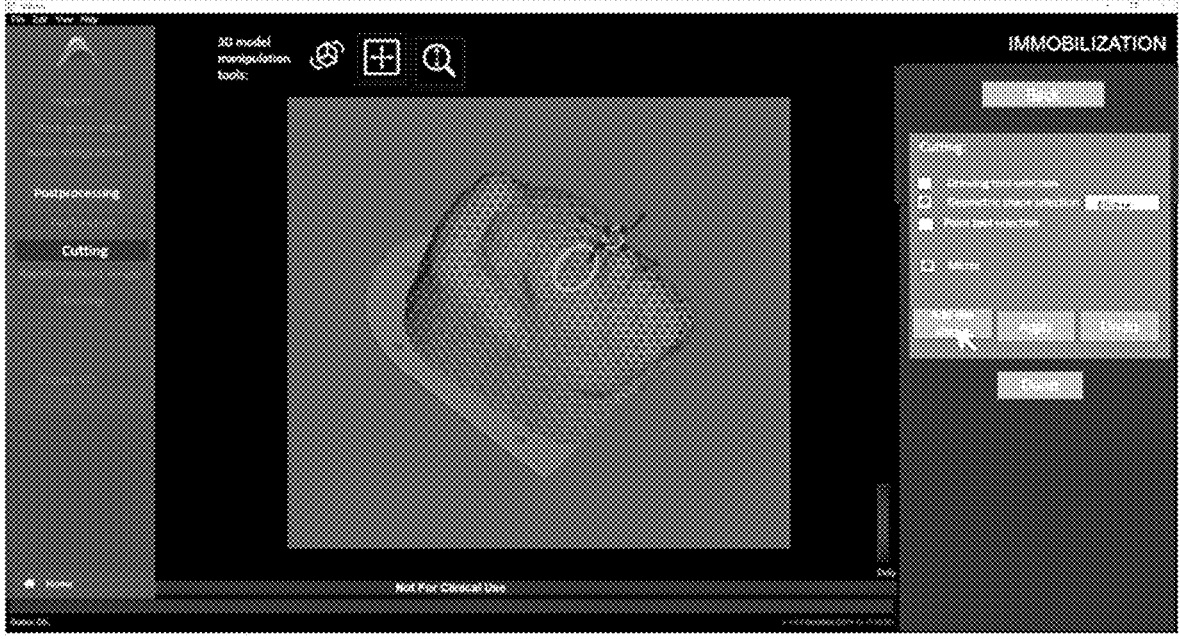
Figure 12C:
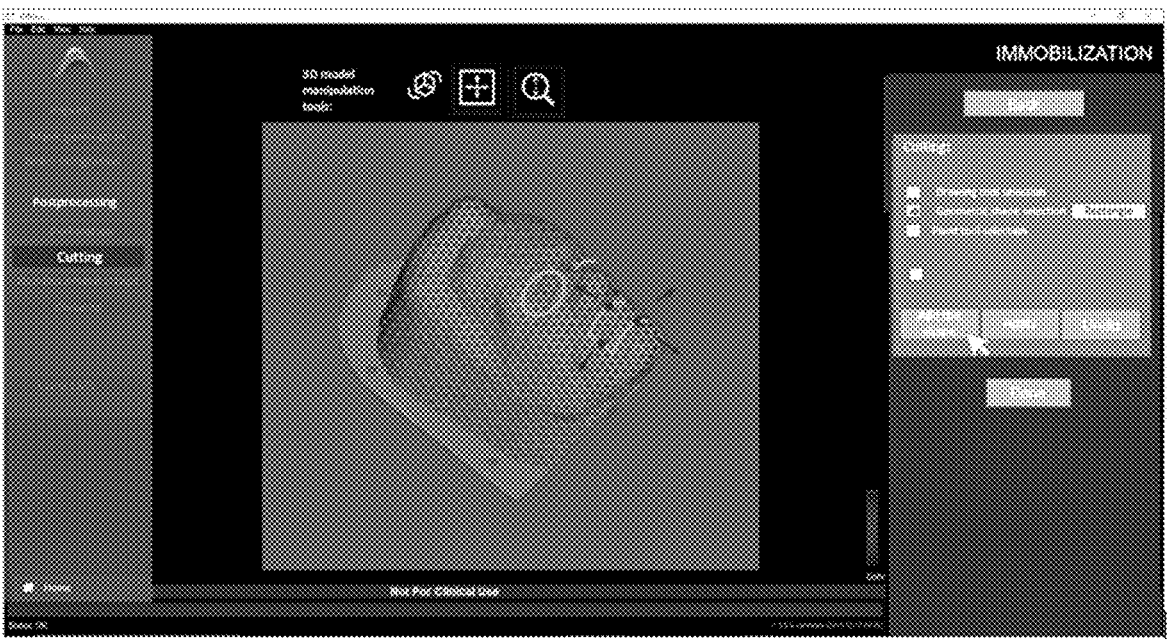
Figure 12D:
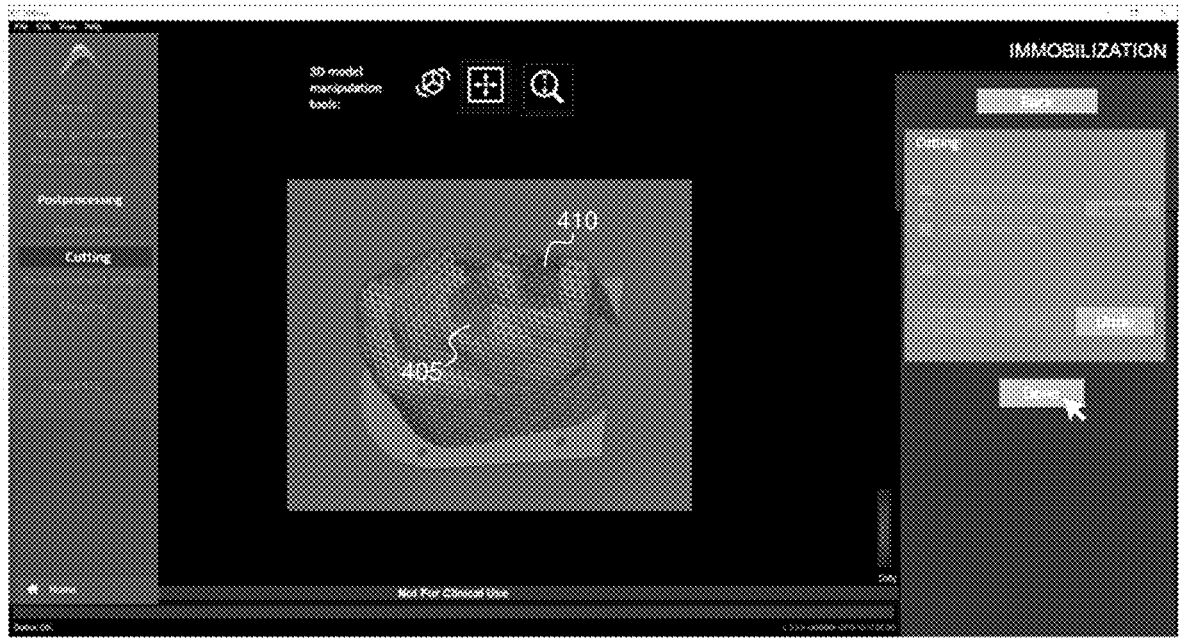

FIGS. 12A-12C show example user interface windows that permit the user to define a contour or boundary region within which to remove material from the digital model of the patient-specific immobilization structure. FIG. 12D shows the resulting modified digital model of the patient-specific immobilization structure that includes eye apertures 400 and 405, and a mouth aperture 410.

Figure 13A:
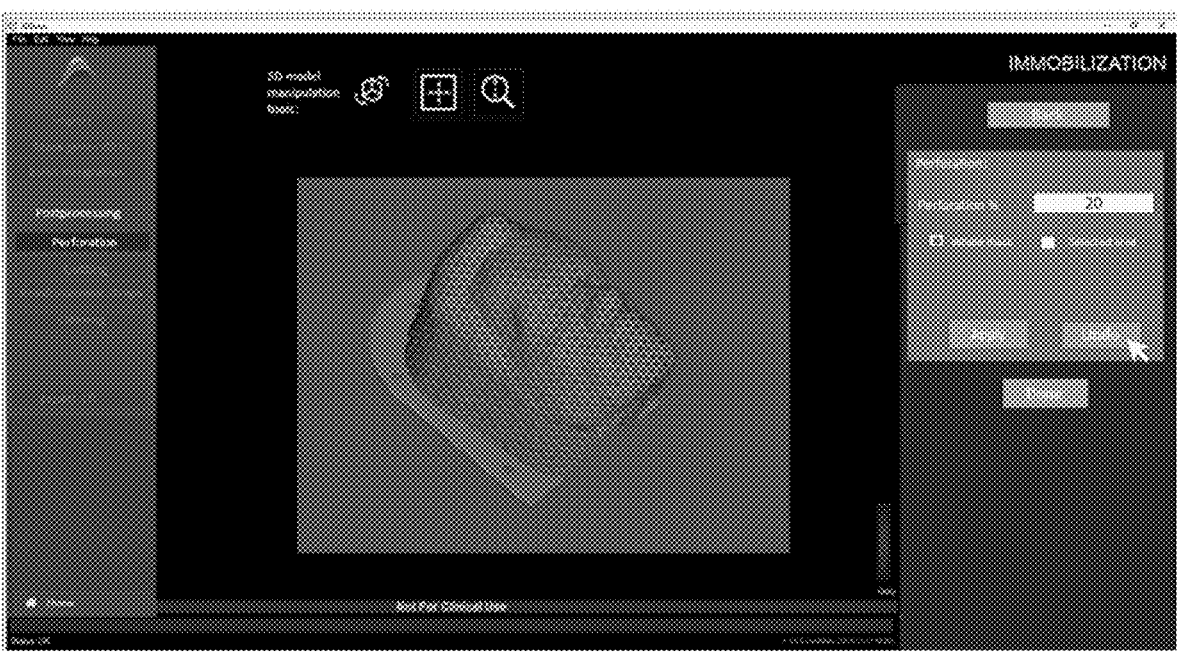
FIGS. 13A-13C illustrate an example method and user interface for modifying a digital model of a patient-customized immobilization structure to incorporate perforation features.
Figure 13B:
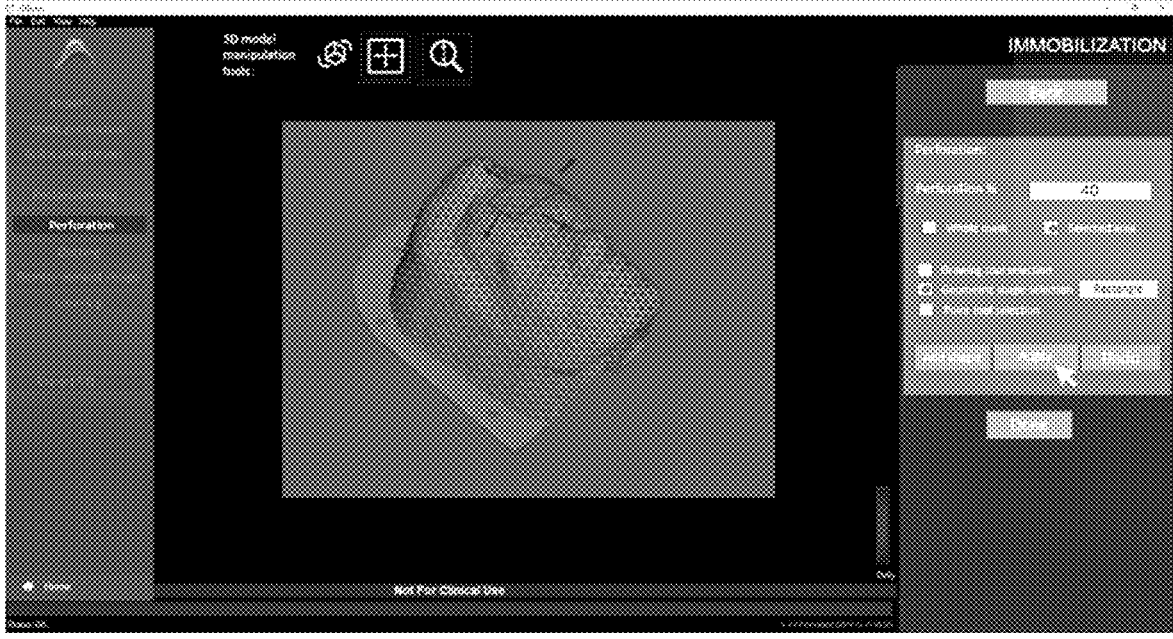
Figure 13C:
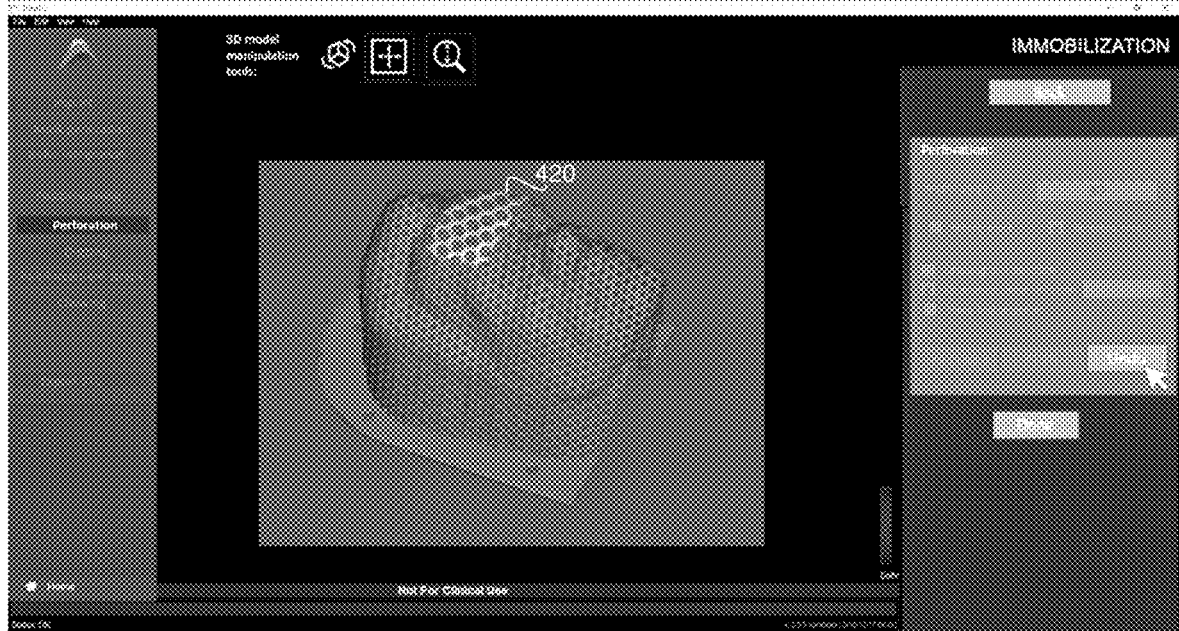

FIGS. 13A-13C show example user interface windows that permit the user to define a contour or boundary region within which to vary a porosity of the digital model of the patient-specific immobilization structure. FIG. 13C shows the resulting modified digital model of the patient-specific immobilization structure that includes a region 420 of increased porosity. It is noted that the remainder of the digital model of the patient-specific immobilization structure may be solid or may also be porous, with the latter case shown in FIGS. 13A-13C. In alternative example implementations, the local density of the material forming the digital model of the patient-specific immobilization structure or the local thickness of the material forming the digital model of the patient-specific immobilization structure may be digitally modified.

Figure 14A:
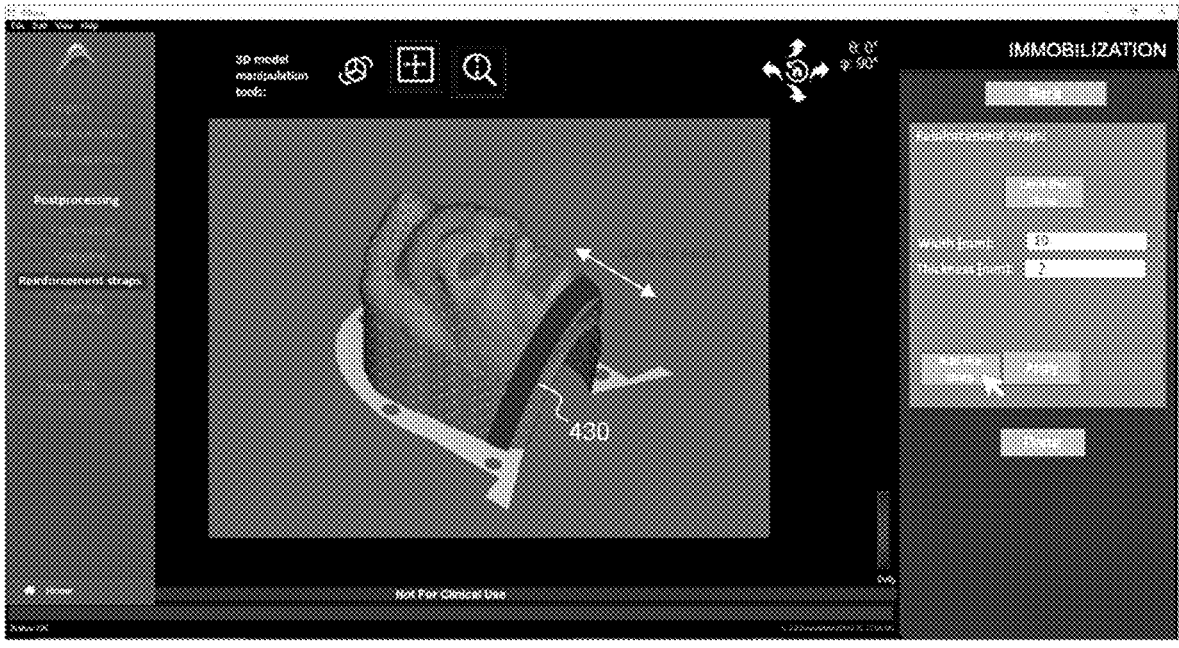
FIGS. 14A-14F illustrate an example method and user interface for modifying a digital model of a patient-customized immobilization structure to facilitate the incorporation of reinforcement straps.
Figure 14B:
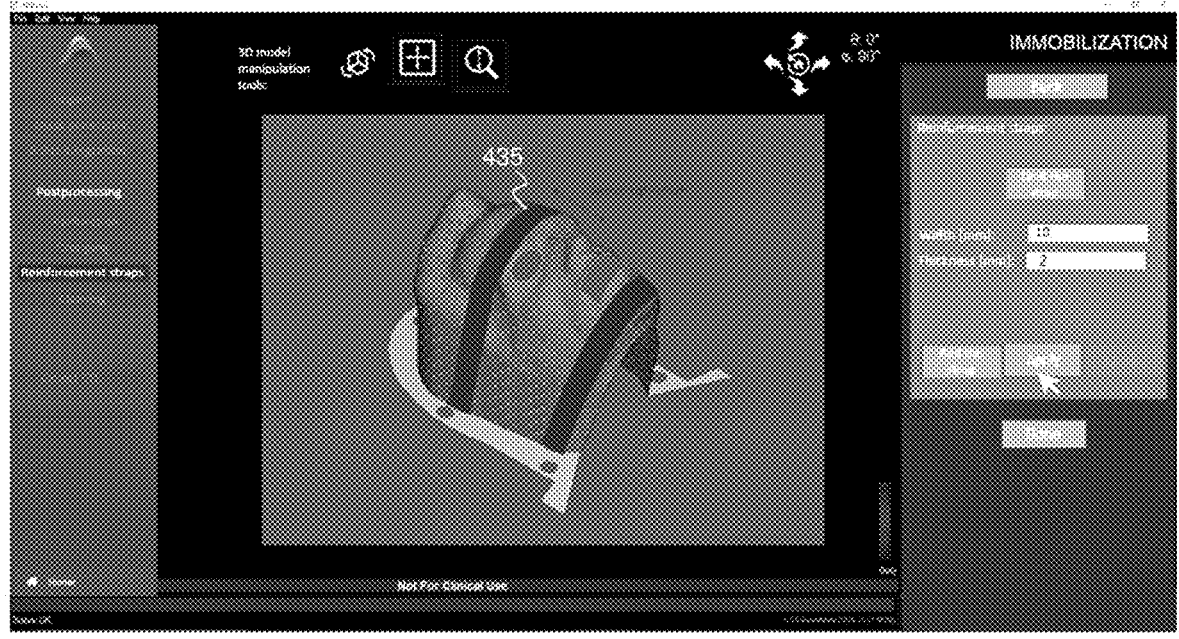
Figure 14C:
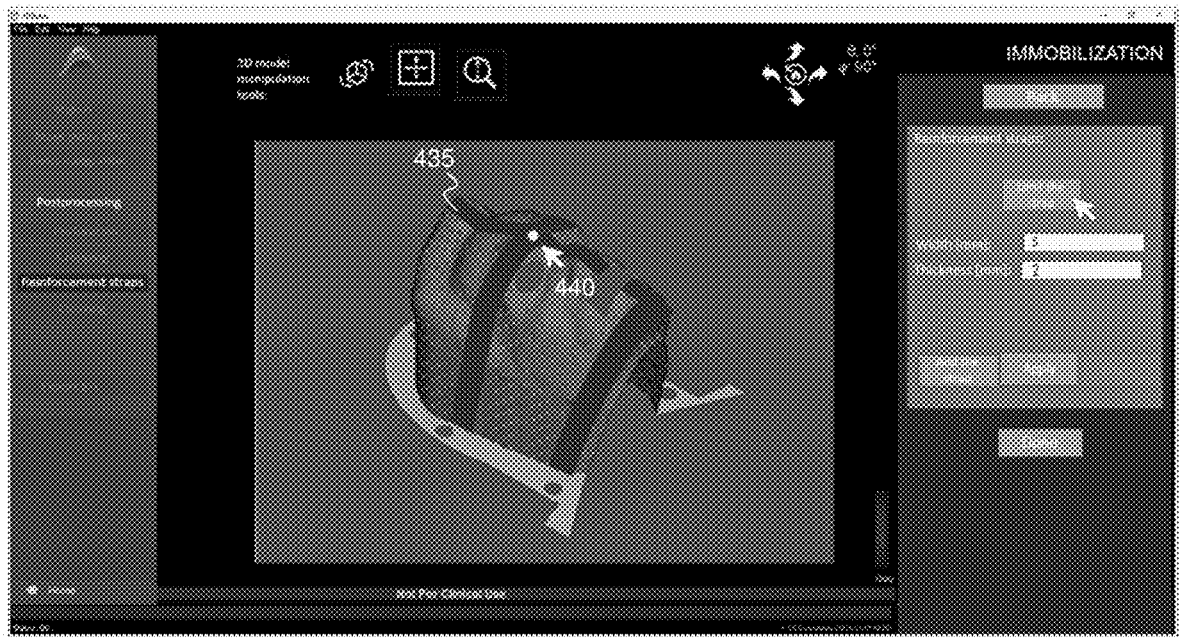
Figure 14D:
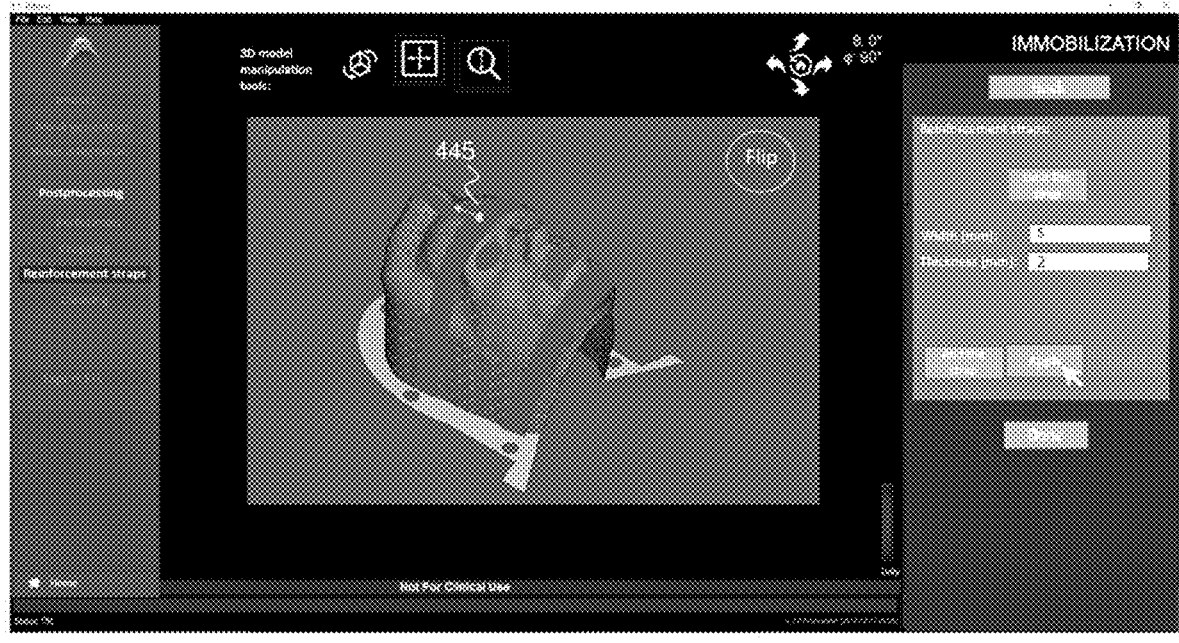
Figure 14E:
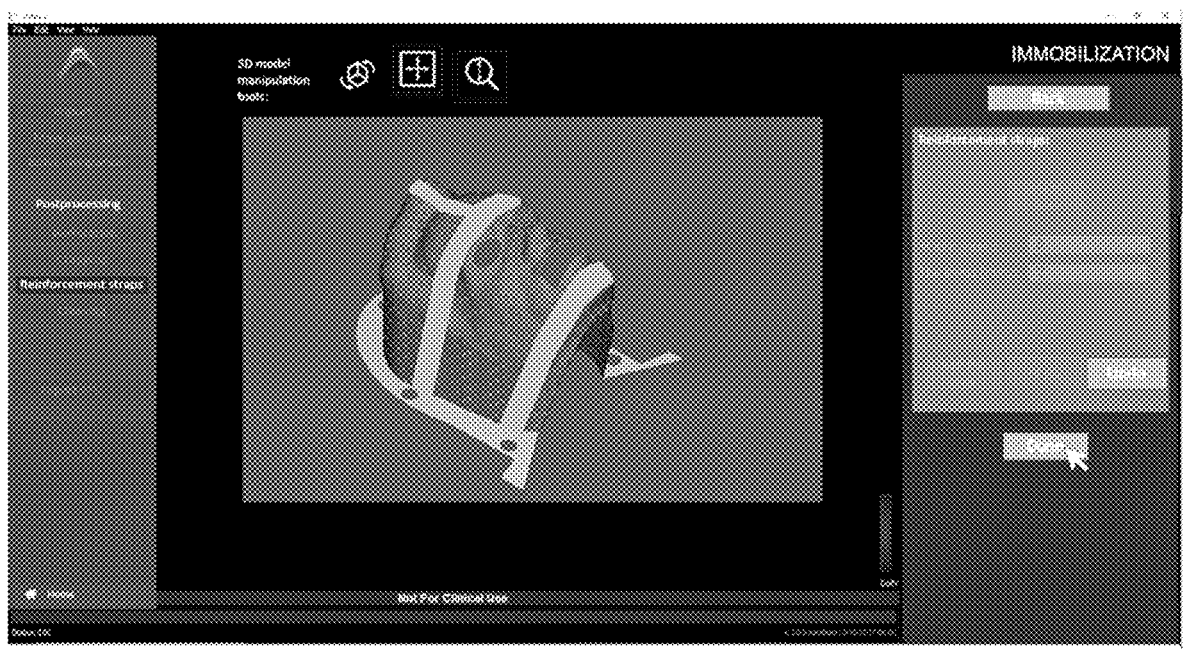

FIGS. 14A-14F show example user interface windows that permit the user to adapt the digital model of the patient-specific immobilization structure for the incorporation of one or more reinforcement straps. FIG. 14A shows an example implementation in which a reinforcement strap is digitally incorporated into the digital model of the patient-specific immobilization structure, with the position of the reinforcement strap relative to the digital model of the patient-specific immobilization structure being user-selectable. FIG. 14B shows an example implementation in which a second reinforcement strap 425 is digitally incorporated into the digital model of the patient-specific immobilization structure, while a third orthogonal reinforcement strap 430 is shown in FIG. 14C. FIG. 14C also includes a point 440 identified for limiting the longitudinal extent of the strap, with FIG. 14D showing the limited strap length 445. FIG. 14E shows the modified digital model of the patient-specific immobilization structure with the three reinforcement straps.

Figure 14F:
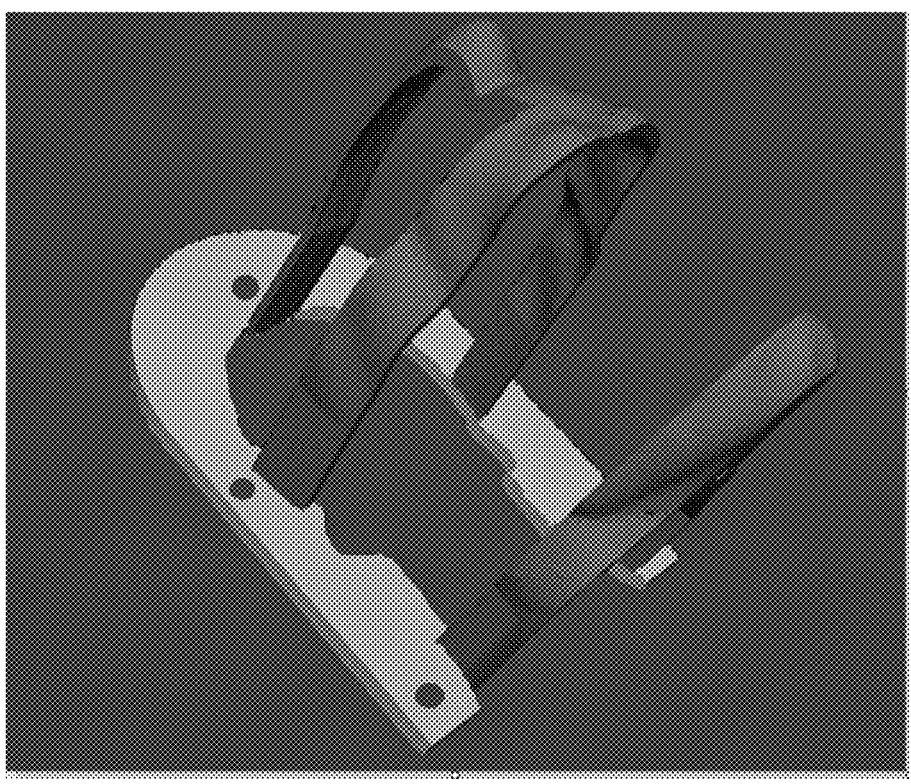

FIG. 14F illustrates an example patient-specific immobilization structure that only includes the frame and the reinforcement straps, with the rest of the material being subtracted, and is thus absent of the conformal shell portion and the extruded portion. In some example implementations, such a simplified patient-specific immobilization structure may be fabricated and employed during at least a portion of a medical procedure. Although such a simplified patient-specific immobilization structure is absent of an immobilization structure that resides conformally adjacent to the surface of the body portion during immobilization, the placement of the reinforcement straps is nonetheless determined based on the patient surface data and the identified position and orientation of the support structure, thereby providing at least partial immobilization of the body portion.

Figure 15A:
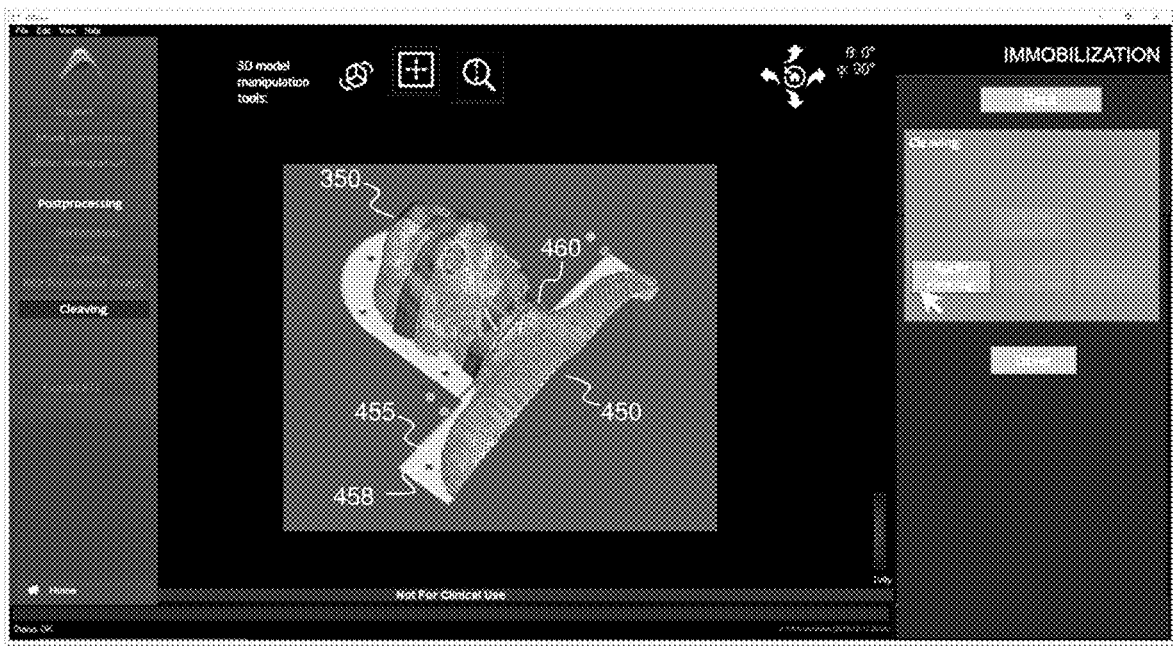
FIGS. 15A-15E illustrate an example method and user interface for modifying a digital model of a patient-customized immobilization structure for cleaving the digital model of a patient-customized immobilization structure into two or more distinct portions.
Figure 15B:
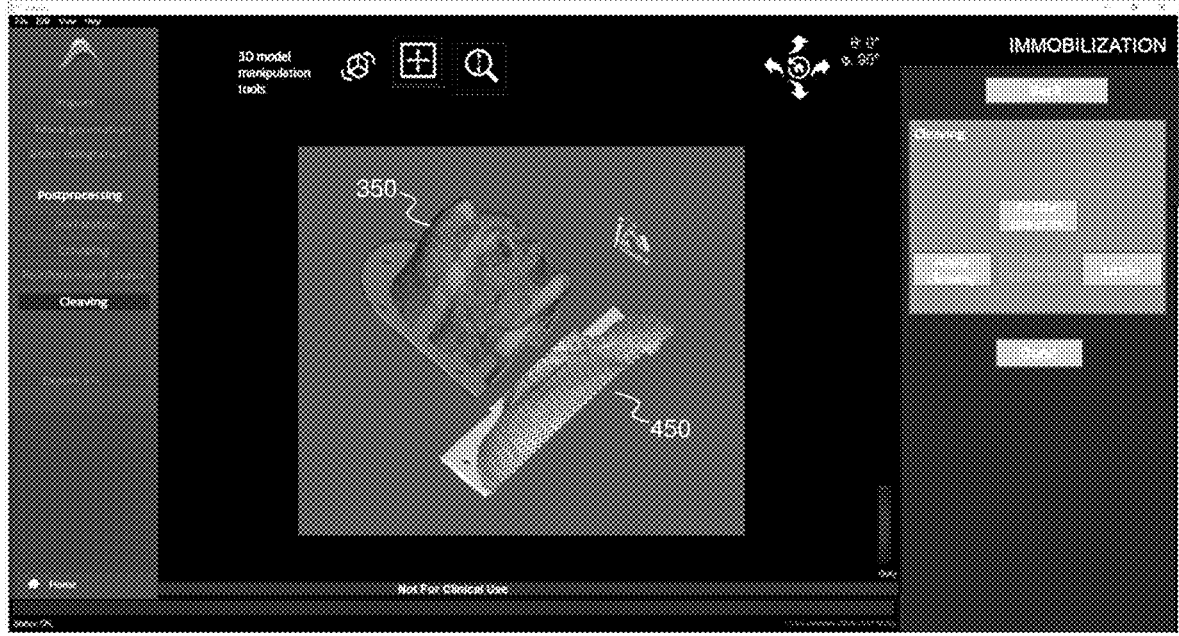
Figure 15C:
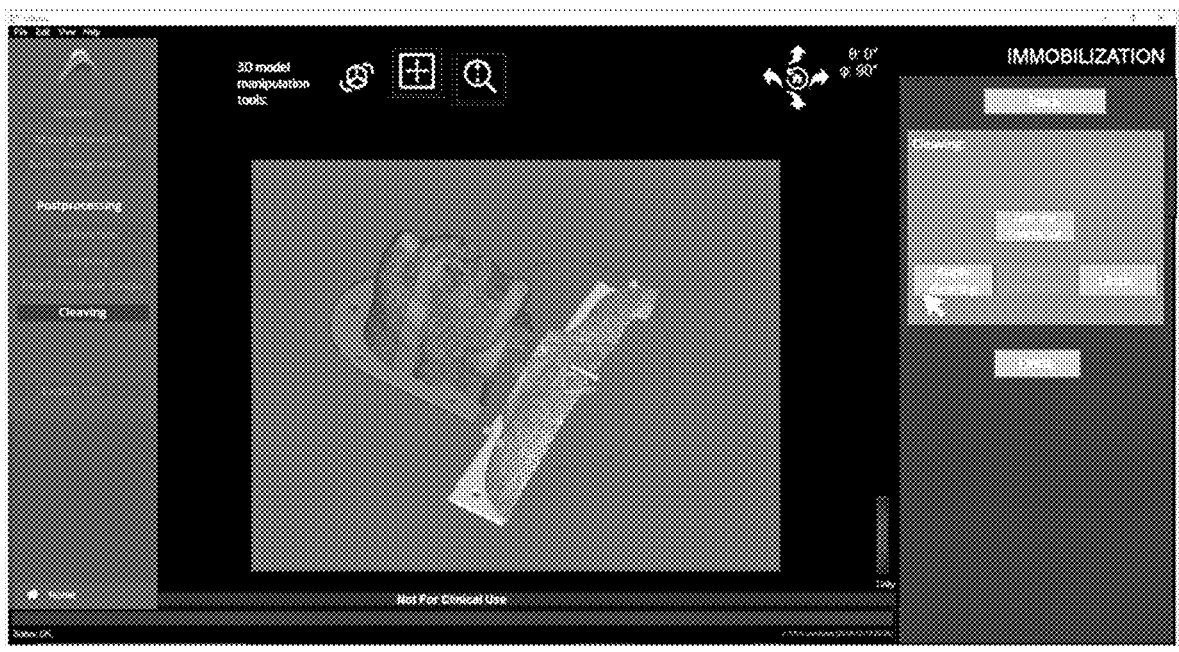
Figure 15D:
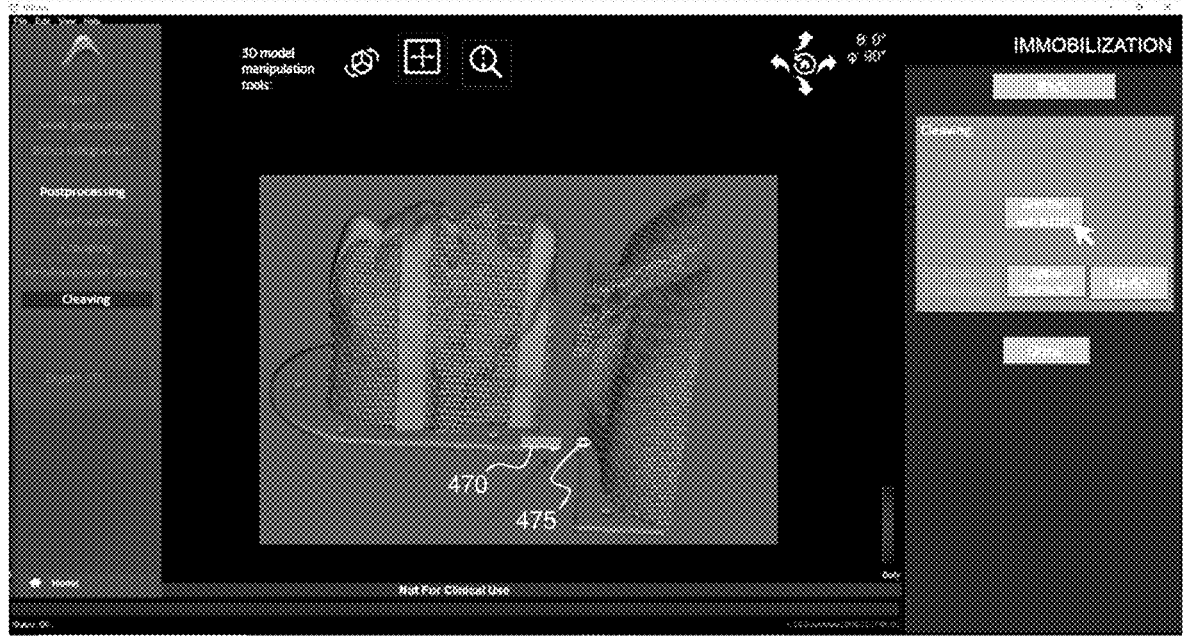
Figure 15E:
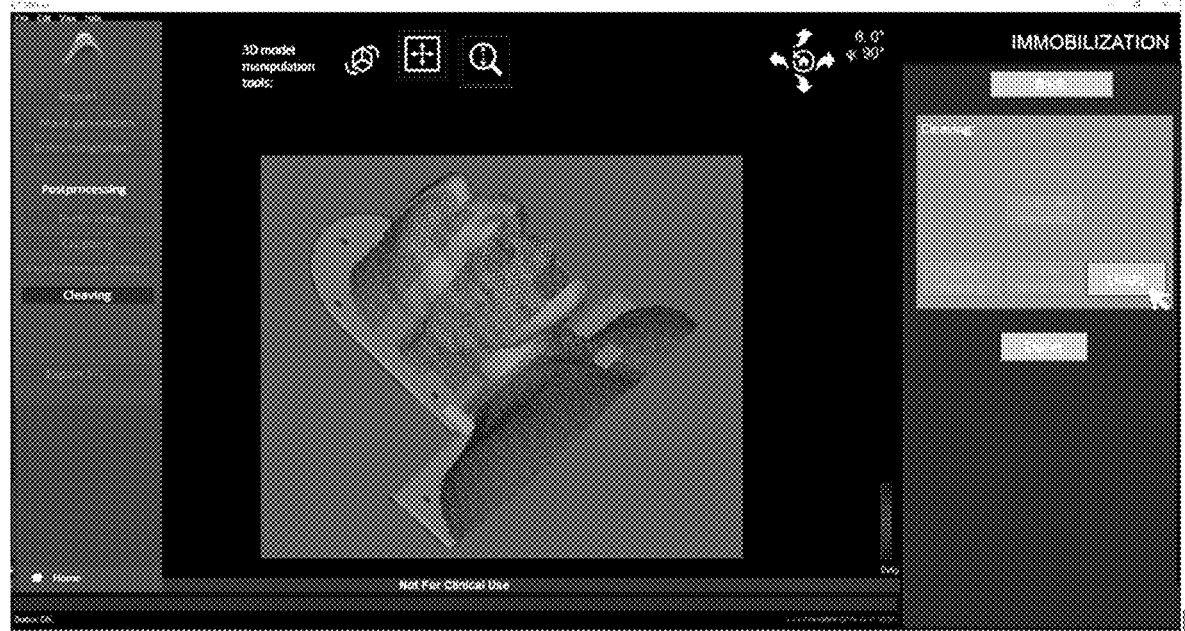

FIGS. 15A-15E show example user interface windows that permit the user to adapt the digital model of the patient-specific immobilization structure to cleave an initial digital model of the patient-specific immobilization structure into two or more portions. FIG. 15A shows an initial digital model of a patient-specific immobilization structure that includes a head portion 350 and an upper body portion 450. The upper body portion 450 includes a body frame 455 having attachment and alignment features that facilitate engagement with support structure, such as hole 458. The user interface permits the user to define a cleave plane location for cleaving the initial digital model of the patient-specific immobilization structure into two portions. The two portions will enable an operator of the fabricated two-part patient-specific immobilization structure to immobilize the patient with greater ease and less discomfort to the patient. FIGS. 15B and 15C show the resulting two-part modified digital model of the patient-specific immobilization structure. As shown in FIG. 15D, the user interface facilitates the incorporation of attachment features for attaching the first and second portions of the patient-specific immobilization structure. FIG. 15E shows a user interface window with the two parts of the patient-specific immobilization structure connected via the attachment features.

Figure 16A:
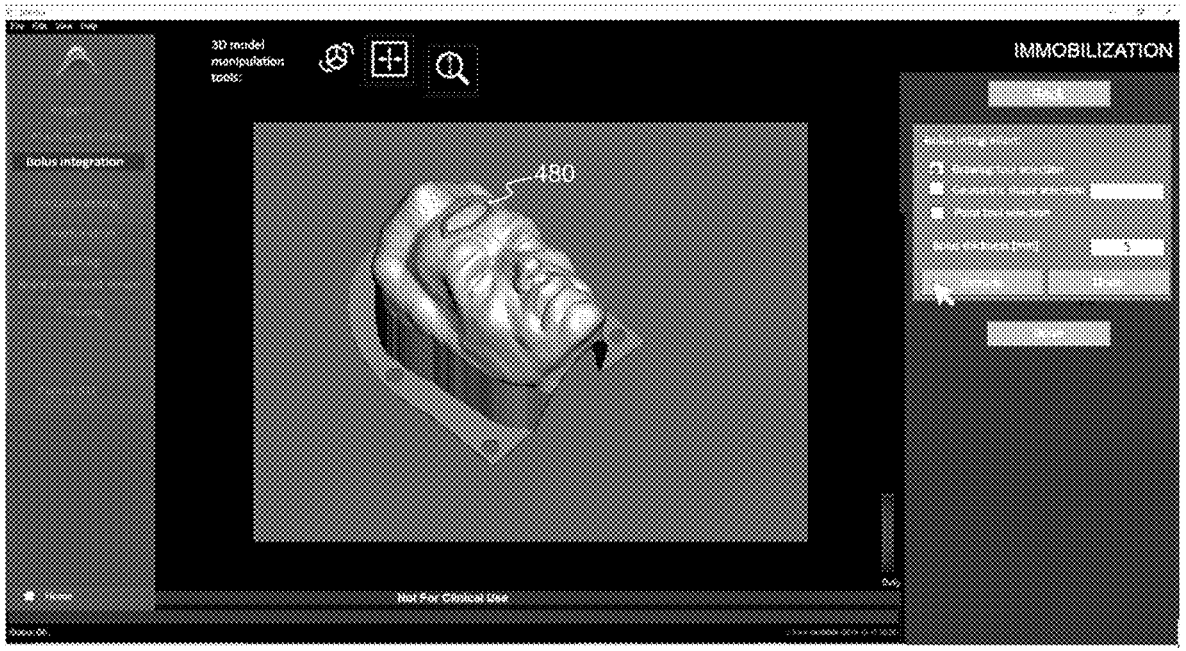
FIGS. 16A-16C illustrate an example method and user interface for modifying a digital model of a patient-customized immobilization structure for incorporation of a radiation bolus.
Figure 16B:
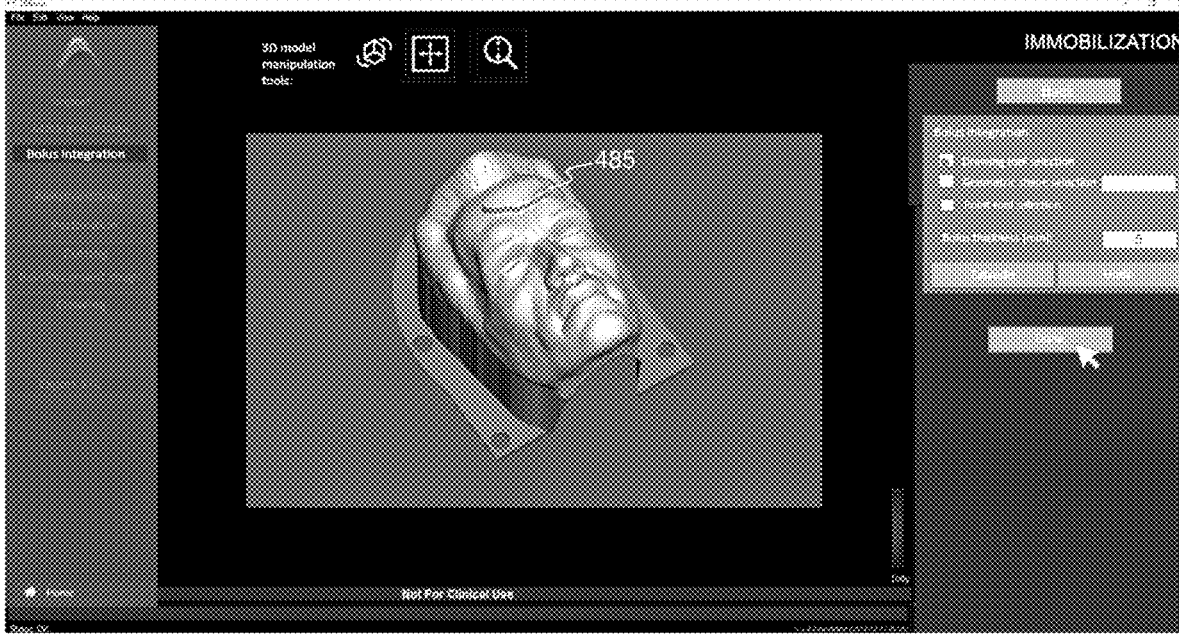
Figure 16C:
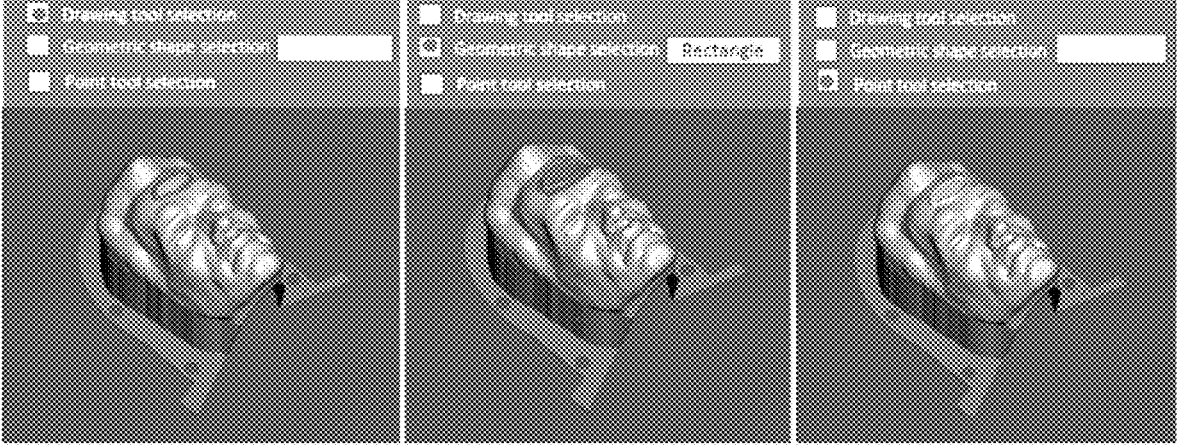

FIGS. 16A-16C show example user interface windows that permit the user to adapt the digital model of the patient-specific immobilization structure to incorporate a radiation bolus. FIG. 16A shows a user-defined bolus contour 480 defining a region on the digital model of the patient-specific immobilization structure for the incorporation of a bolus. A bolus region 485 is then generated by locally increasing the thickness of the patient-specific immo-bilization structure according to user-defined thickness. FIG. 16C illustrates various example selectable bolus-defining modalities of the user interface, including a drawing tool, a geometric shape selection, and a point tool selection.

Figure 17:
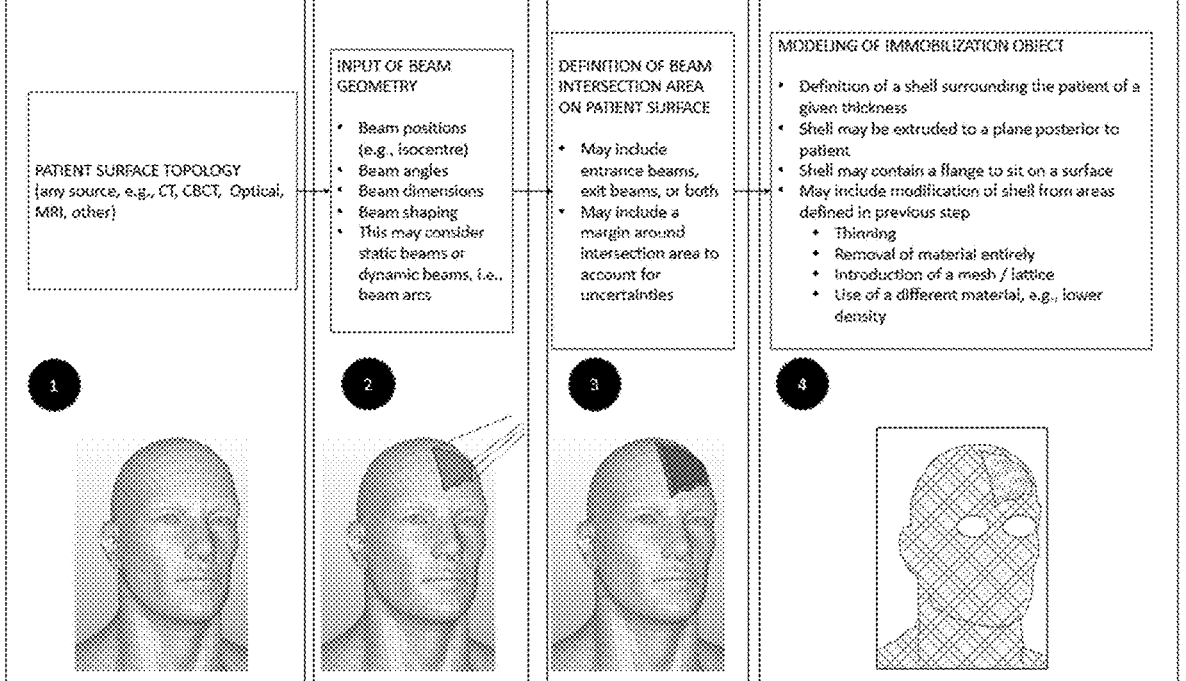
FIG. 17 illustrates an example method of employing beam parameters associated with a radiotherapy treatment plan to perform treatment-specific modifications to a patient-specific immobilization structure prior to its fabrication and use.

In some example embodiments, one or more beam param-eters associated with an initial radiotherapy treatment plan may be employed to modify the digital model of the patient-specific immobilization structure prior to its fabrication. An example of such an embodiment is schematically illustrated in FIG. 17. As shown in the figure, initial image data characterizing the patient surface topography is employed to generate an initial digital model of a patient-specific immo-bilization structure. The beam parameters are then deter-mined in common frame of reference with the digital model of the patient-specific immobilization structure. This can be achieved, for example, by employing a known position and orientation of the support structure relative to digital model of the patient-specific immobilization structure, and a known position of the support structure relative to the therapeutic system during the therapeutic procedure, as prescribed according to the treatment plan. Alternatively, if the image data employed to generate the patient-specific immobilization structure is the volumetric image data employed to generate the treatment plan, then the patient-specific immobilization structure is already or can be directly transformed into the frame of reference of the treatment planning system.

In cases in which the image data employed to generate the patient-specific immobilization structure is optical surface data and the treatment plan was generated based on separate volumetric image data, the beam parameters can be deter-mined in a common frame of reference with the patient-specific immobilization structure by performing image reg-istration between (i) the surface data employed to generate the digital model of the patient-specific immobilization structure and (ii) surface data segmented from volumetric image data previously employed to generate the treatment plan, with the image registration providing a coordinate transformation for representing the radiation beams in a common frame of reference with the digital model of the patient-specific immobilization structure.

In an alternative example workflow, a treatment plan may be generated, in a treatment planning system, based on the initial digital model of the patient-specific immobilization structure, and this treatment plan may be subsequently employed to modify the initial digital model of the patient-specific immobilization structure based one or more beam parameters associated with the treatment plan. This may be performed, for example, by importing the initial digital model of the patient-specific immobilization structure into a treatment planning system. For example, the initial digital model of the patient-specific immobilization structure may be processed to generate a digital model in a tomographic format, which may then be imported into the treatment planning system in a prescribed position and orientation, relative to a treatment system. This prescribed or known position and orientation may be determined based on a prescribed or known position in which the support structure is attachable relative to a patient table or other component of a treatment system, thereby positioning and orienting the tomographic slices characterizing patient-specific immobi-lization structure in the correct orientation in the treatment planning system.

An operator may subsequently employ a user interface of the treatment planning system to define the position of the isocentre within the volume of the patient-specific immobilization structure. This step of defining the isocentre could be performed, for example, based on a known location of the disease (known from prior imaging, e.g. imaging performed during the diagnosis phase). Alternatively, the isocentre could be defined based on a realistic arrangement of beams converging on that isocentre location. Such an approach may be possible because for many treatment sites, a "class solution" beam arrangement is used, i.e., a standard set of beams with regard to number and angles of incidence. Furthermore, while the importation of such a dataset into a treatment planning system would not provide the detail needed to accurately define a target volume (CTV, PTV), this target volume is often known in advance, and thus a good or sufficient approximation of the location of the target volume within the volume associated with the patient-specific immobilization structure be made, when defining beam dimensions, with reference to the previously deter-mined target location. For example, one may define a placeholder volume of interest inside the volume associated with the patient-specific immobilization structure (or based on surface data employed to generate the digital model of the patient-specific immobilization structure), optionally adding a margin. The collimation of the beams may be set according to this volume of interest, and this beam collimation may be adequate for use during the subsequent modification of the initial digital model of the patient-specific immobilization structure.

Having determined parameters associated with one or more treatment beams, the treatment beams may then be projected on the patient-specific immobilization structure, thereby facilitating modification of the initial digital model of the patient-specific immobilization structure, as described below. In some example implementations, the output from the treatment planning system (e.g., a DICOM RT plan object or other) may be employed and processed by separate immobilization design software for the digital modification of the initial model of the patient-specific immobilization structure.

As shown in frame 3 of FIG. 17, the beam projection onto the initial digital model of a patient-specific immobilization structure may be generated according to beam parameters associated with, but not limited to, one or more entrance beams, exit beams, or a combination thereof. Furthermore, the beam projection may denote or include a margin, such as a margin accounting for uncertainties or tolerances associ-ated with beam delivery and/or patient positioning.

As shown in frame 4 of FIG. 17, the beam projection may be employed to perform one or more treatment-specific modifications to the initial digital model of a patient-specific immobilization structure. Such a modified digital model of the patient-specific immobilization structure is therefore not only uniquely customized to the patient anatomical curva-ture, but also customized according to a treatment plan associated with the patient. Non-limiting examples of treat-ment-plan-specific modifications include locally varying the thickness of the digital model of the patient-specific immo-bilization structure within a projected beam region, remov-ing material from the digital model of the patient-specific immobilization structure to create an aperture within a projected beam region, locally varying a porosity and/or density of the digital model of the patient-specific immobi-lization structure within a projected beam region, and locally varying a material composition of the digital model of a patient-specific immobilization structure within a projected beam region.

Figure 18A:
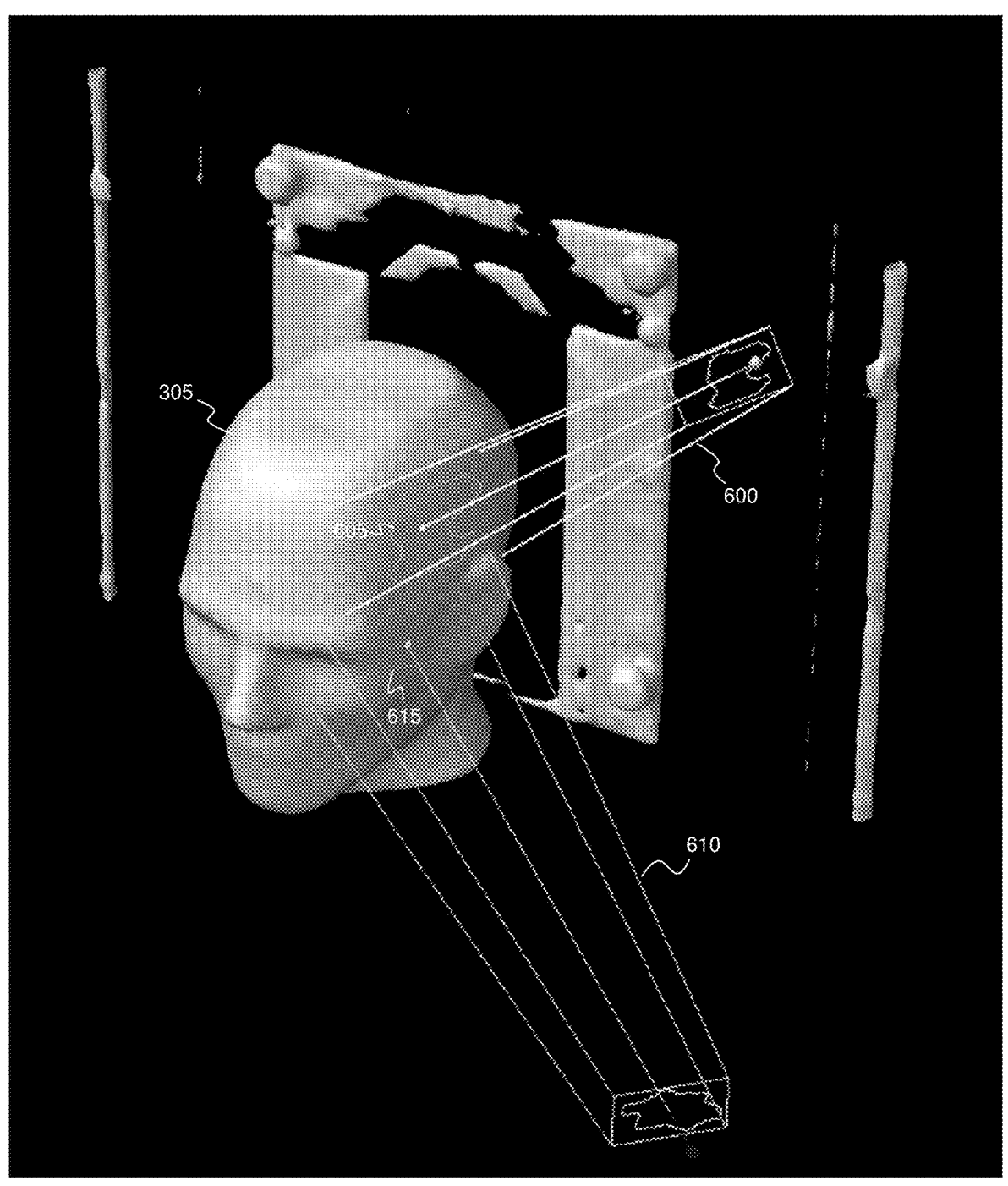
FIGS. 18A and 18B show the projection of treatment beams onto surface data characterizing an exposed surface of a body portion of the patient and a portion of a support structure on which a body portion of the patient rests.
Figure 18B:
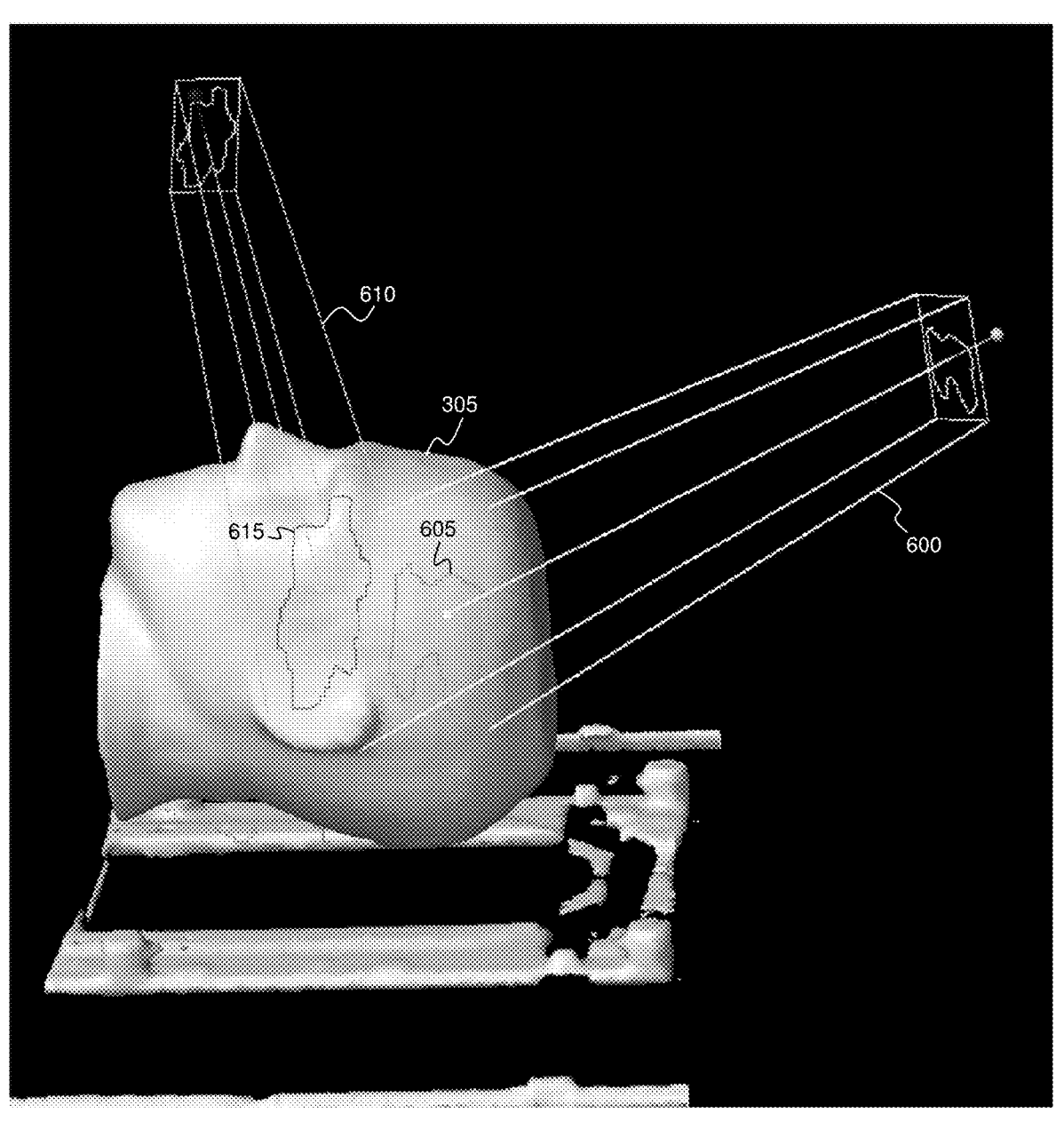

An example of the projection of beams relative to the segmented patient surface data that is employed to generate the patient-specific immobilization structure is shown in FIGS. 18A and 18B. The figures show to projected beams 600 and 610 and the resulting projected regions on the surface of the segmented patient surface 305.

Figure 19A:
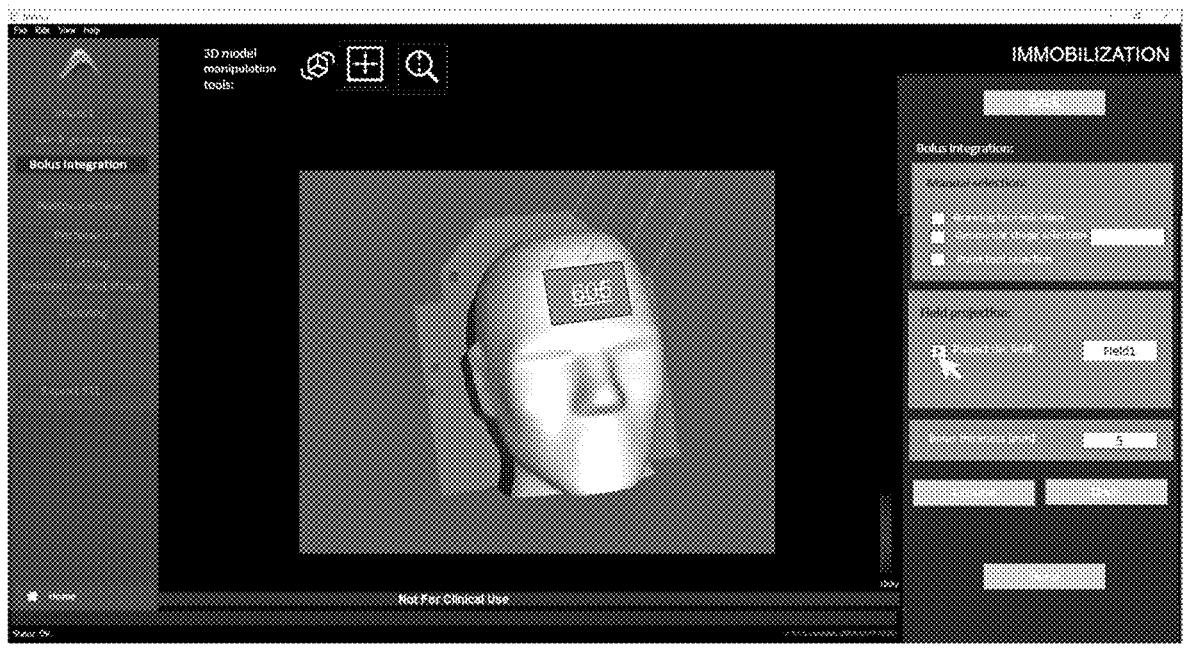
FIGS. 19A and 19B illustrate an example method and user interface for modifying a digital model of a patient-specific immobilization structure to integrate a radiation bolus that spatially overlaps with a projected location of a radiation beam associated with a treatment plan.
Figure 19B:
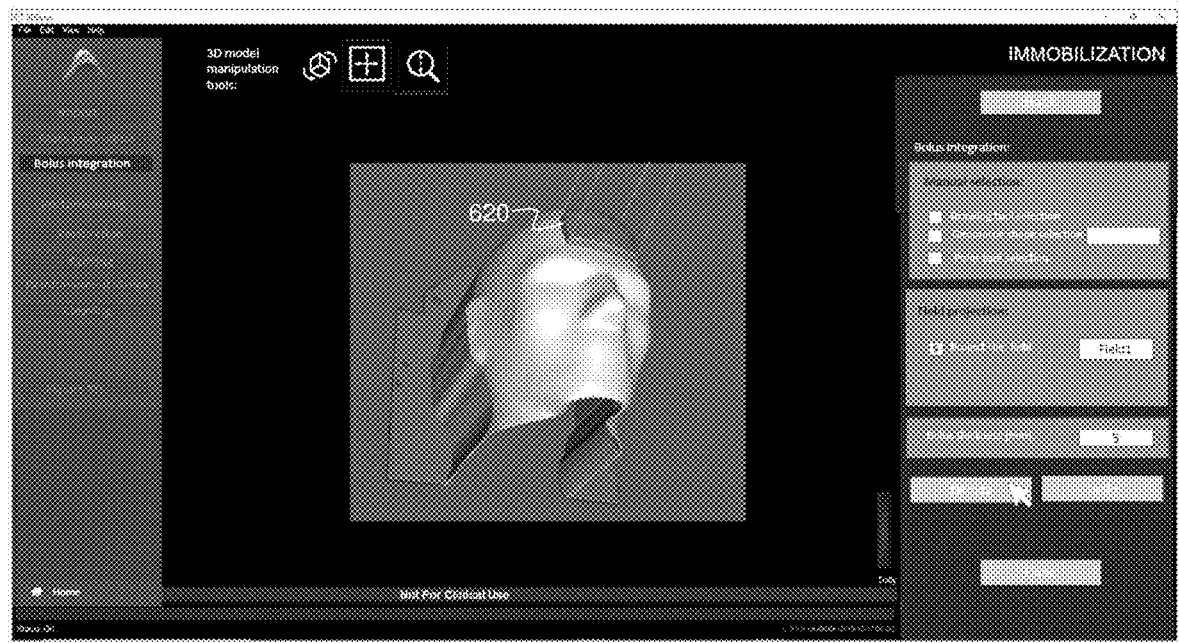
Figure 20A:
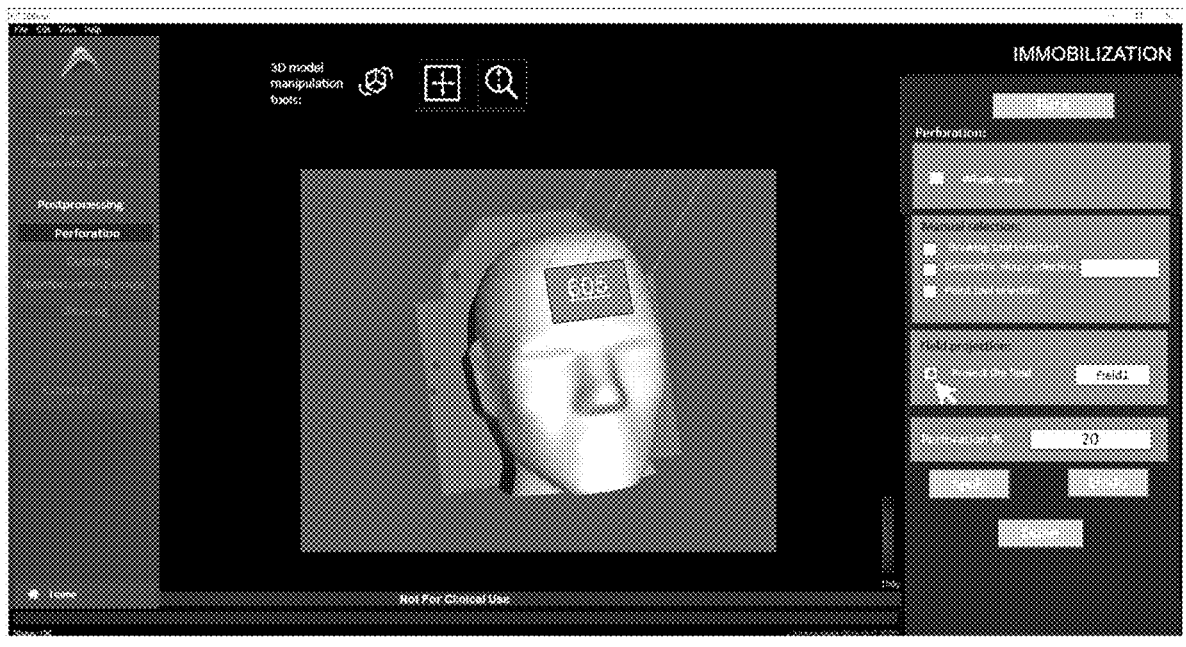
FIGS. 20A and 20B illustrate an example method and user interface for modifying a digital model of a patient-specific immobilization structure to include a perforated region that spatially overlaps with a projected location of a radiation beam associated with a treatment plan.
Figure 20B:
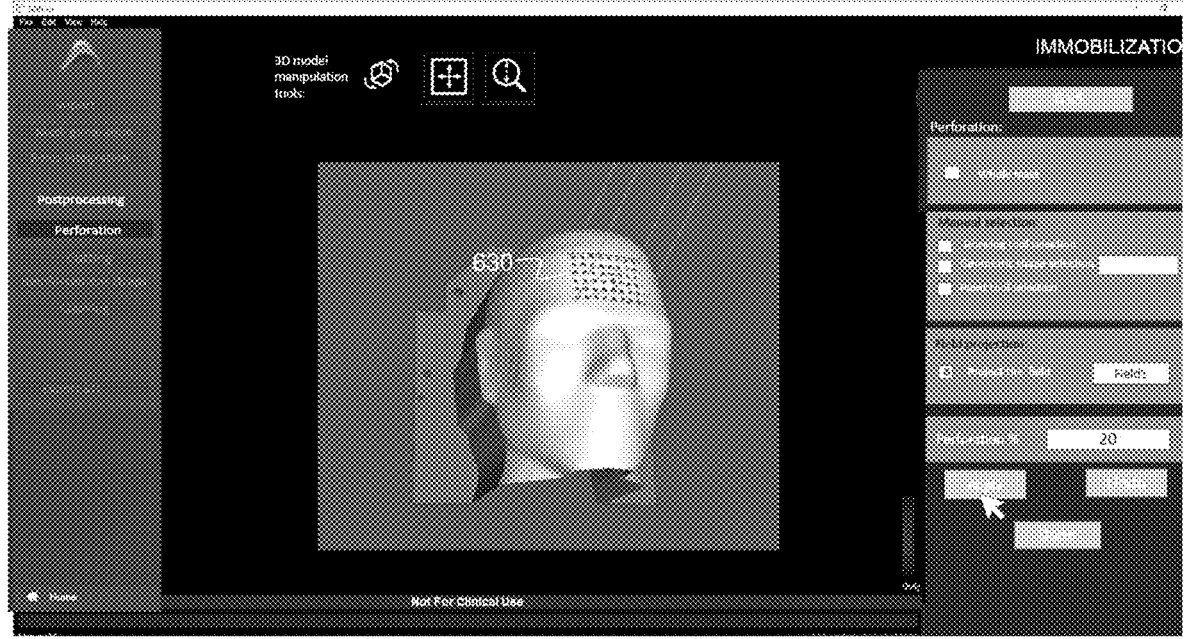
Figure 21A:
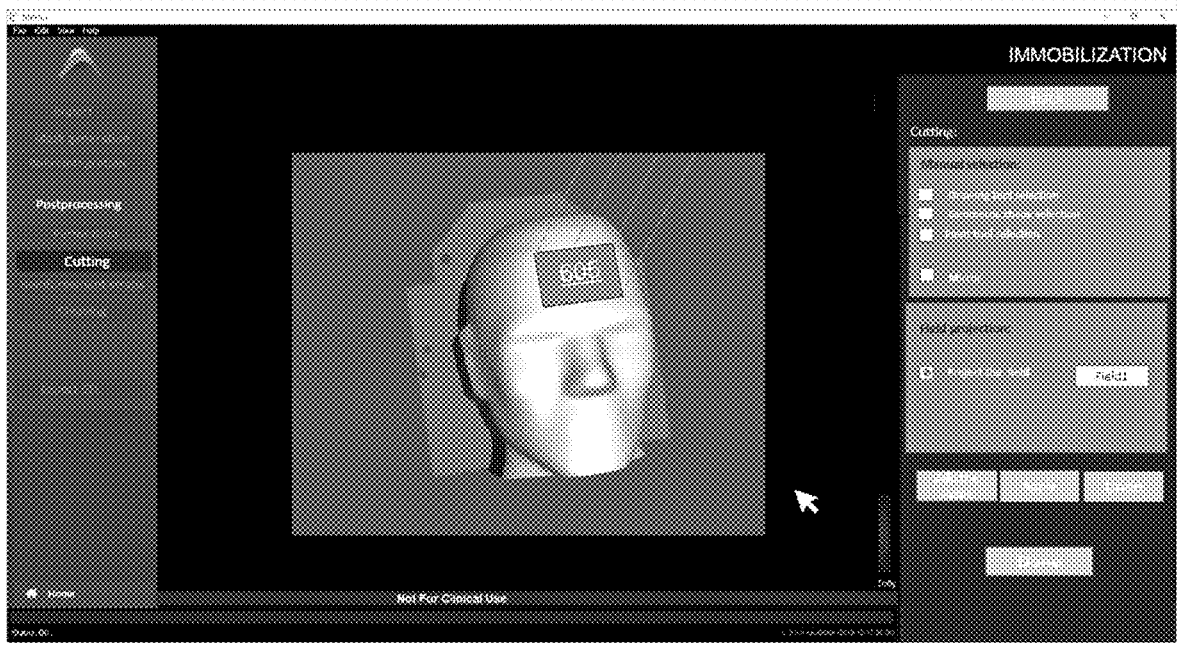
FIGS. 21A and 21B illustrate an example method and user interface for modifying a digital model of a patient-specific immobilization structure to provide an aperture, via removal of material of the immobilization support, spatially overlapping with a projected location of a radiation beam associated with a treatment plan.
Figure 21B:
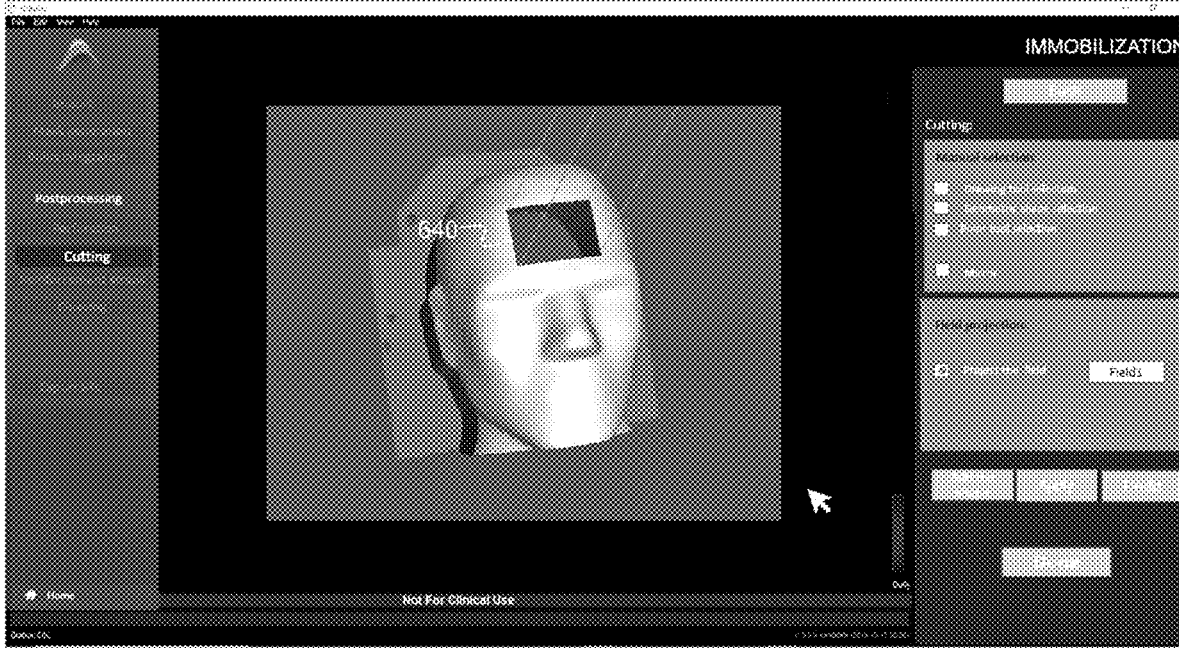
Figure 22:
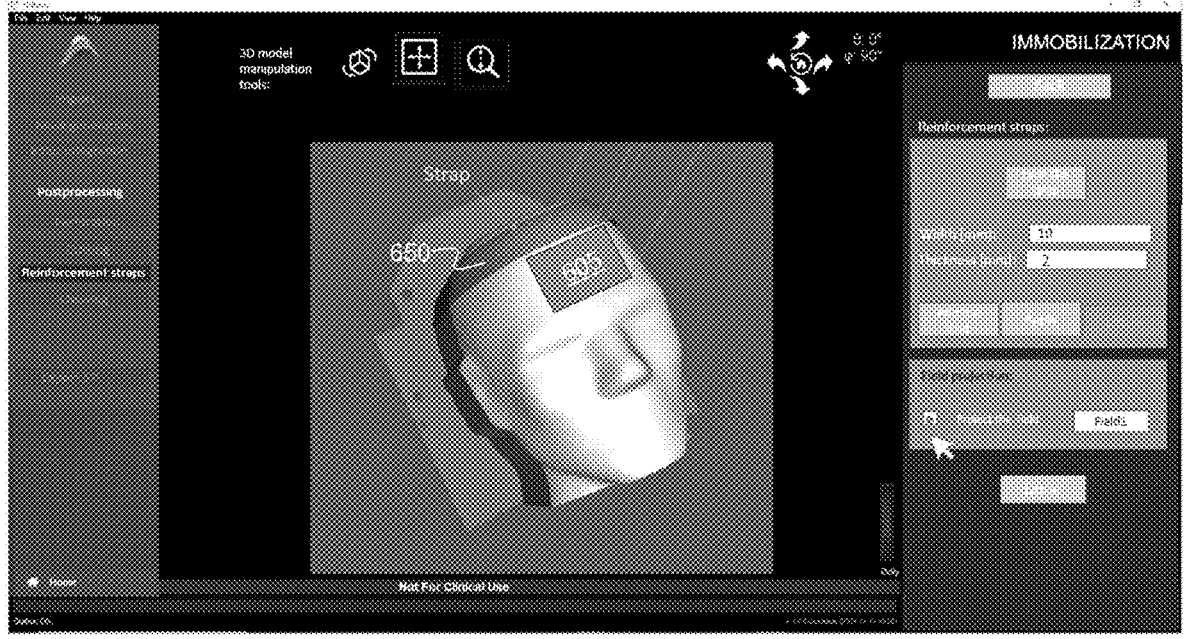
FIG. 22 illustrates an example method and user interface for modifying a digital model of a patient-specific immobilization structure to include a reinforcement strap that does not spatially overlap with a projected location of a radiation beam associated with a treatment plan.
Figure 23:
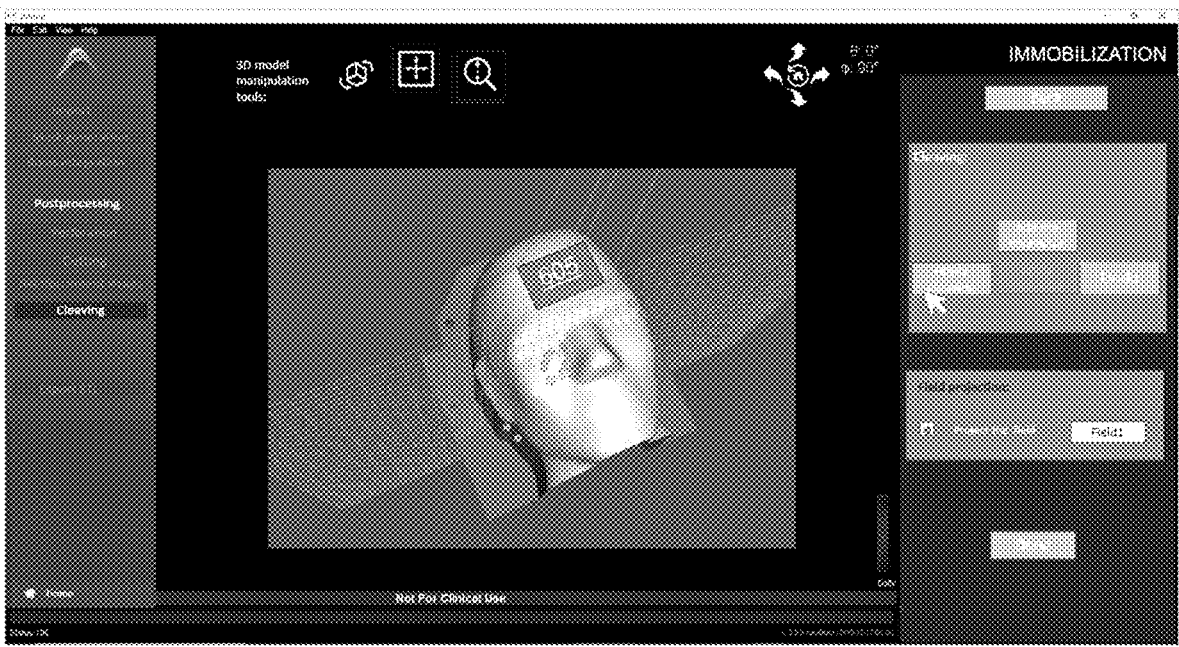
FIG. 23 illustrates an example method and user interface for cleaving a digital model of a patient-specific immobilization structure with a cleave plane that does not spatially overlap with a projected location of a radiation beam associated with a treatment plan.

Non-limiting examples of treatment-beam-specific modifications, as presented and optionally controlled in a user interface, are shown in FIGS. 19A-19B, 20A-20B, 21A-21B, and 22. FIGS. 19A, 20A and 21A show user interface views that identify the region of spatial overlap 605 between a projected beam and the initial digital model of the patient-specific immobilization structure. FIGS. 19B, 20B and 21B show user interface views in which the initial digital model of the patient-specific immobilization structure has been locally modified, within the beam projection region, to respectively incorporate a bolus 620, a region of increase perforation 630, and an aperture absent of material 640. FIG. 22 illustrates an example method and user interface for modifying a digital model of a patient-specific immobilization structure to include a reinforcement strap that does not spatially overlapping with a projected location of a radiation beam associated with a treatment plan. In FIG. 23, a user interface view is shown in which an initial digital model of a patient-specific immobilization structure is cleaved with a cleave plane that does not spatially overlap with a projected location of a radiation beam associated with a treatment plan.

FIG. 24 is a flow chart illustrating an example method of generating and modifying a digital model of a patient-specific immobilization structure according to beam parameters from an initial radiotherapy treatment plan.

The modification of an initial digital model of the patient-specific immobilization structure within a region associated with a projected beam defined according to treatment plan is illustrated in the example flow chart shown in FIG. 24. The flow chart illustrates an example modification of step 220 from the flow chart shown in FIG. 4. As shown at steps 250-260, an initial digital model of the patient-specific immobilization structure is generated, for example, as described previously, and a treatment plan is employed to determine one or more beam parameters in a common frame of reference with the initial digital model of the patient-specific immobilization structure. The initial digital model is then modified according to the one or more beam parameters, such as by locally modifying one or more properties of the initial digital model within a spatial region involving an overlap between a projected beam and the surface of the digital model. The modified digital model of the patient-specific immobilization structure may then be fabricated, as per step 225A of FIG. 24. The fabricated patient-specific immobilization structure may then be employed during the therapeutic procedure, optionally after first obtaining additional volumetric image data with body portion immobilized by the patient-specific immobilization structure and employing the additional volumetric image data to refine the treatment plan, as illustrated in the optional steps shown at 230A and 235A in FIG. 24.

In some example implementations, the fabricated patient-specific immobilization structure may be an initial patient-specific immobilization structure, and a second patient-specific immobilization structure may be subsequently fabricated for use in the therapeutic procedure. For example, the patient may be immobilized with the initially fabricated patient-specific immobilization structure and additional volumetric image data may be collected. This additional volumetric image data may be employed to refine the treatment plan, and the refined treatment plan may be employed to modify the initial digital model of the patient-specific immobilization structure, for example, as per the example beam-specific modifications described above. The modified digital model of the patient-specific immobilization structure may then be fabricated an employed to immobilize the patient during the therapeutic procedure. In some example implementations, the initially fabricated patient-specific immobilization structure may be a 'light' version having less material and/or confining features than the final patient-specific immobilization structure. For example, the initial patient-specific immobilization structure may include two or more 3D printed straps for immobilizing the patient in a prescribed position and orientation relative to the support structure, and this initial patient-specific immobilization structure is used to immobilize the patient during the collection of volumetric image data for use during subsequent treatment planning, and the treatment plan is employed to refine the final digital model of the patient-specific immobilization structure. In some example implementations, the initial ("light") version of the digital model of the patient-specific immobilization structure could be employed to form a basis for the generation of the final digital model of the patient-specific immobilization structure.

Although some of the preceding example implementations have referred to optical surface scanning, it will be understood that a wide variety of imaging modalities may be employed that are capable of directly or indirectly providing surface data characterizing a surface of an exposed body portion (and a portion of a support structure supporting the body portion). Non-limiting examples of suitable imaging modalities include structured light, LIDAR, stereographic surface imaging, and volumetric imaging modalities such as computed tomography, tomosynthesis imaging, and magnetic resonance imaging.

Furthermore, although many of the preceding example embodiments refer to procedures involving the head, it will be understood that the example embodiments described herein may be adapted to a wide range of diagnostic and therapeutic procedures involving the immobilization of body portion. For example, the present example embodiments may be adapted for breast immobilization. In such as case, the patient would be placed on a breast board, possibly with a lift to separate the breast tissue from the chest wall at the infra-mammary fold. This lift would position the breast in the desired treatment position prior to the capture of image data. In this embodiment, the immobilizer would serve to immobilize the treated breast in the desired treatment position, and for example, immobilize the contralateral breast so that it is positioned out of the treatment fields. In the case of bilateral breast treatment both breasts would be immobilized in the treatment position. The attachment of a breast immobilizer may be attached in a relocatable way to the breast board using mechanisms similar to those described above, e.g., straps attached to preset positions on the breast board, latches, snaps, tabs, or Velcro in conjunction with locating pins.

Figure 25:
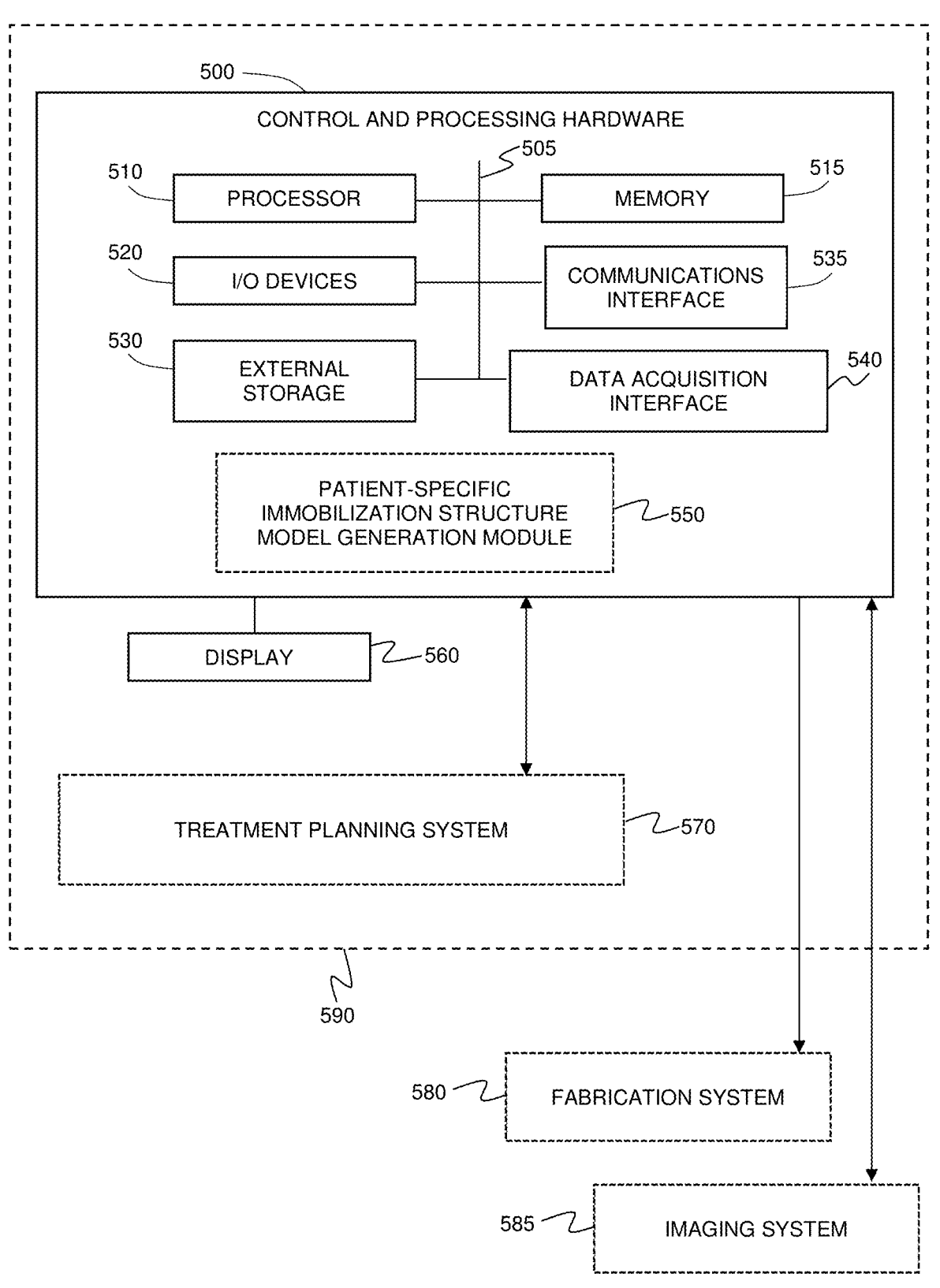
FIG. 25 illustrates an example system for generating a patient-customized immobilization structure using patient-specific surface data.

Referring now to FIG. 25, an example schematic of a system for generating a digital model of a patient-specific immobilization structure is shown. Control and processing hardware 500 may include a processor 510, a memory 515, a system bus 505, one or more input/output devices 520, and a plurality of optional additional devices such as communications interface 535, display 525, external storage 530, and data acquisition interface 540. In one example implementation, the display 560 may be employed to provide a user interface for displaying images of a digital model of a patient-specific immobilization structure and/or for facilitating input to control the operation of the system 500. As shown in FIG. 25, the display and/or the treatment planning system 570 may be directly integrated into a control and processing device, as shown at 590 (for example, as an embedded display), or may be provided as an external device (for example, an external monitor). The control and processing system 500 may be connected to a fabrication system 580 (such as, but not limited to, a 3D printer) for fabricating a patient-specific immobilization structure according to a digital patient-specific immobilization structure. The control and processing system 500 may also be connected to an imaging system 585 for acquiring the initial image data that is employed to generate the surface data characterizing the exposed surface of the body portion and a portion of the support structure.

The methods described herein, including the initial design of the digital patient-specific immobilization structure and the refinement (modification) of the patient-specific immobilization structure, can be implemented via processor 510 and/or memory 515. As shown in FIG. 25, executable instructions represented as patient-specific immobilization structure model generation module 550 are processed by control and processing hardware 500 to generate a digital model of patient-specific immobilization structure. Such executable instructions may be stored, for example, in the memory 515 and/or other internal storage. The control and processing hardware 500 may optionally be interfaced with a treatment planning system 570, for example, to facilitate the performing of dose calculations and the exporting of relevant RT DICOM elements, including RT structures associated with an initial digital model of a patient-specific immobilization structure, and/or to facilitate importation of an initial treatment plan for use in performing treatment-plan-customized modifications of the digital model of the patient-specific immobilization structure.

The methods described herein can be partially implemented via hardware logic in processor 510 and partially using the instructions stored in memory 515. Some embodiments may be implemented using processor 510 without additional instructions stored in memory 515. Some embodiments are implemented using the instructions stored in memory 515 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing hardware 500 may be provided as an external component that is interfaced to a processing device. Furthermore, although the bus 505 is depicted as a single connection between all of the components, it will be appreciated that the bus 505 may represent one or more circuits, devices or communication channels which link two or more of the components. For example, the bus 505 may include a motherboard. The control and processing hardware 500 may include many more or less components than those shown.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine-readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

It will be understood that the example patient-specific immobilization structure design workflow and system described above is intended to provide a non-limiting example embodiment. The workflow and/or system may be modified or adapted without departing from the intended scope of the present disclosure.

For example, while some example workflows and system implementations involve the use of a treatment planning system and a separate patient-specific immobilization structure design system, these two systems may be integrated into a common system for integrated design of the patient-specific immobilization structure and the processing of the dose calculation and treatment plan generation, as shown by 590 in FIG. 25.

Furthermore, although the preceding example embodiments pertained to the design of a patient-specific immobilization structure for cranial applications and procedures, the systems and methods described above may be adapted for the design of patient-specific immobilization structures associated with other treatment sites, such as head-and-neck, neck and shoulders, breast, spine, abdomen, pelvis or extremities.

A patient-specific immobilization structure model generated according to the present example embodiments can be manufactured according to many different example methods and is particularly well-suited to automated fabrication methods such as 3D printing. 3D printing is a specific form of additive manufacturing. One of the most common methods of 3D printing is fused deposition modeling (FDM). This process has recently has become widely accessible at low cost, such as MakerBot devices. 3D printing involves a fabrication process that uses a CAD model as input to create a 3D physical model by applying many successive layers of the chosen material at a high resolution, such as a resolution of 100 micrometers, although the system can use other resolutions and capabilities.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of fabricating an immobilization device for immobilizing a body portion of a patient, the method comprising:

providing a support structure suitable for supporting a body portion of the patient;

with the body portion supported by contact with the support structure, employing an imaging system to obtain image data suitable for characterizing an exposed surface of the body portion and at least a portion of the support structure;

processing the image data to determine a position and orientation of the support structure based on one or more known spatial features of the support structure;

processing the image data to segment surface data associated with the exposed surface of the body portion;

employing the surface data and the position and orientation of the support structure to generate a digital model of a patient-specific immobilization structure that is attachable to the support structure for immobilizing the body portion between the patient-specific immobilization structure and the support structure; and fabricating the patient-specific immobilization structure according to the digital model.

2. The method according to claim 1 wherein the patient-specific immobilization structure comprises an alignment feature configured to contact a corresponding feature of the support structure for aligning the patient-specific immobilization structure relative to the support structure prior to attachment.

3. The method according to claim 2 wherein the alignment feature of the patient-specific immobilization structure comprises a first surface that is configured to contact a corresponding second surface of the support structure when the patient-specific immobilization structure is aligned with the support structure for immobilizing the body portion between the patient-specific immobilization structure and the support structure.

4. The method according to claim 1 wherein at least one of the one or more known spatial features are fiducial features.

5. The method according to claim 1 wherein the surface data is segmented, at least in part, by employing the one or more known spatial features of the support structure to remove support structure image data associated with the support structure from the image data.

6. The method according to claim 1 wherein the digital model of the patient-specific immobilization structure comprises at least one attachment feature that facilitates attachment of the patient-specific immobilization structure with the support structure when the patient-specific immobilization structure is aligned with the support structure for immobilizing the body portion between the patient-specific immobilization structure and the support structure.

7. The method according to claim 6 wherein the at least one attachment feature of the patient-specific immobilization structure cooperates with a respective attachment feature of the support structure for attaching the patient-specific immobilization structure to the support structure.

8. The method according to claim 1 wherein the digital model of the patient-specific immobilization structure comprises:

a conformal shell region conforming to at least a portion of the surface data associated with the exposed surface of the body portion; and an extrusion region that extends from the conformal shell region to the support structure.

9. The method according to claim 8 wherein the support structure comprises a planar surface, and wherein a direction of extrusion is perpendicular to the planar surface.

10. The method according to claim 1 wherein the image data is initial image data, the method further comprising:

with the body portion contacting the support structure and immobilized via attachment of the patient-specific immobilization structure to the support structure, acquiring volumetric image data characterizing the body portion; and providing the volumetric image data to a treatment planning system for generating a treatment plan, such that the treatment plan is generated based on the volumetric image data obtained with the body portion immobilized by the patient-specific immobilization structure.

11. The method according to claim 10 further comprising employing the patient-specific immobilization structure to immobilize the body portion during a therapeutic procedure performed according to the treatment plan.

12. The method according to claim 1 further comprising:

employing the digital model of the patient-specific immobilization structure to generate a treatment plan with a treatment planning system.

13. The method according to claim 1 wherein the patient-specific immobilization structure is associated with a radiotherapy procedure, the radiotherapy procedure having an associated treatment plan, and wherein generating the digital model comprises:

employing the surface data and the position and orientation of the support structure to generate an initial digital model of the patient-specific immobilization structure that is attachable to the support structure for immobilizing the body portion between the patient-specific immobilization structure and the support structure;

employing the treatment plan to determine one or more beam parameters in a common frame of reference with the initial digital model;

locally modifying the initial digital model according to the one or more beam parameters, thereby obtaining a modified digital model of the patient-specific immobilization structure;

wherein the patient-specific immobilization structure is fabricated according to the modified digital model.

14. The method according to claim 13 wherein the treatment plan is an initial treatment plan, the method further comprising:

with the body portion immobilized relative to the support structure via attachment of the patient-specific immobilization structure to the support structure, acquiring volumetric image data characterizing the body portion and the one or more spatial features; and providing the volumetric image data to a treatment planning system for generating a refined treatment plan, such that the refined treatment plan is based on the volumetric image data obtained with the body portion immobilized by the patient-specific immobilization structure.

15. The method according to claim 14 further comprising employing the patient-specific immobilization structure, fabricated according to the modified digital model of the patient-specific immobilization structure, to immobilize the body portion during a therapeutic procedure performed according to the refined treatment plan.

16. The method according to claim 13 wherein the one or more beam parameters comprise one or more of a beam position, beam angle, beam dimension, and beam shape.

17. The method according to claim 13 wherein the one or more beam parameters are associated with one or more of an entrance beam and an exit beam.

18. The method according to claim 13 wherein locally modifying the initial digital model comprises:

locally thinning the initial digital model within an intersection region characterized by intersection with a planned radiation beam.

19. The method according to claim 13 wherein locally modifying the initial digital model comprises:

locally varying a density of the initial digital model within an intersection region characterized by intersection with a planned radiation beam.

20. The method according to claim 13 wherein locally modifying the initial digital model comprises:

locally varying a material type of the initial digital model within an intersection region characterized by intersection with a planned radiation beam.

21. The method according to claim 13 wherein locally modifying the initial digital model comprises:

modifying the initial digital model to include an aperture within an intersection region characterized by intersection with a planned radiation beam.

22. The method according to claim 13 wherein locally modifying the initial digital model comprises:

modifying the initial digital model to include a meshed region within an intersection region characterized by intersection with a planned radiation beam, such that porosity of the modified digital model within the intersection region is less than the porosity of the modified digital model within a neighbouring region adjacent to the intersection region.

23. The method according to claim 22 wherein the modified digital model is solid and absent of mesh structure within the neighbouring region.

24. The method according to claim 13 wherein locally modifying the initial digital model comprises:

locally increasing a thickness of the initial digital model to form a radiation bolus within an intersection region characterized by intersection with a planned radiation beam.

25. The method according to claim 13 wherein locally modifying the initial digital model comprises:

displaying, on a user interface, projected locations of radiation beams generated according to the one or more beam parameters; and locally modifying the initial digital model according to user input received via the user interface.

26. The method according to claim 1 wherein generating the digital model comprises:

employing the surface data and the position and orientation of the support structure to generate an initial digital model of the patient-specific immobilization structure that is attachable to the support structure for immobilizing the body portion between the patient-specific immobilization structure and the support structure;

receiving, via a user interface, user input for modifying the initial digital model of the patient-specific immobilization structure;

locally modifying the initial digital model according to user input, thereby obtaining a modified digital model of the patient-specific immobilization structure;

wherein the patient-specific immobilization structure is fabricated according to the modified digital model.

27. The method according to claim 1 wherein the support structure comprises a baseplate.

28. The method according to claim 27 wherein the one or more spatial features are integrated with or supported by the baseplate.

29. The method according to claim 27 wherein the digital model of the patient-specific immobilization structure comprises a flange that is configured to contact a surface of the baseplate when the patient-specific immobilization structure is spatially registered with the support structure for immobilizing the body portion between the patient-specific immobilization structure and the support structure.

30. The method according to claim 29 wherein the flange of the patient-specific immobilization structure comprises one or more first alignment and/or attachment features that are aligned with one or more respective second alignment and/or attachment features in the baseplate when the patient-specific immobilization structure is aligned with the support structure for immobilizing the body portion between the patient-specific immobilization structure and the support structure.

31. The method according to claim 30 wherein the one or more first alignment and/or attachment features are selected from the group consisting of holes, pins and tabs.

32. The method according to claim 27 wherein the body portion comprises at least a portion of a head and wherein the support structure comprises a headrest secured to or integrally formed with the baseplate.

33. The method according to claim 32 wherein the headrest is configured to support the head with the patient, and wherein generating the digital model comprises:

processing the surface data to determine a contour of widest coronal cross-section; and extruding the digital model from the contour of widest coronal cross-section, such that the patient-specific immobilization structure comprises an immobilization portion having a patient-specific surface profile suitable for immobilizing the head and an extruded portion that spatially registers the immobilization portion with the baseplate.

34. The method according to claim 33 wherein the digital model comprises a flange configured to contact the baseplate when the patient-specific immobilization structure is spatially registered to the support structure for immobilizing the body portion, the flange extending outwardly from the extruded portion in a plane residing parallel to the baseplate and posterior to the patient.

35. The method according to claim 34 wherein the flange comprises one or more first holes that are aligned with one or more respective second holes in the baseplate when the patient-specific immobilization structure is aligned with the support structure for immobilizing the body portion between the patient-specific immobilization structure and the support structure.

36. The method according to claim 27 wherein the baseplate includes at least one positioning feature suitable for removably securing the baseplate to a component of a diagnostic or therapeutic system.

37. The method according to claim 36 wherein the component is a patient couch.

38. The method according to claim 1 wherein the digital model comprises strap attachment features for securing at least one reinforcing strap, such that when the patient-specific immobilization structure is fabricated and at least one the reinforcing strap is secured to the patient-specific immobilization structure, a rigidity of the patient-specific immobilization structure is increased.

39. The method according to claim 1 wherein the imaging system is a surface imaging system, and wherein the image data is surface image data.

40. The method according to claim 1 wherein the patient-specific immobilization structure is fabricated with a three-dimensional printer.

41. A system for use in generating an immobilization device for immobilizing a body portion of a patient, the system comprising:

processing circuitry comprising at least one processor and associated memory, the memory comprising instructions executable by the at least one processor for performing operations comprising:

receiving image data suitable for characterizing an exposed surface of a body portion of the patient and at least a portion of a support structure employed to support the body portion during imaging;

processing the image data to determine a position and orientation of the support structure based on one or more known spatial features of the support structure;

processing the image data to segment surface data associated with the exposed surface of the body portion; and employing the surface data and the position and orientation of the support structure to generate a digital model of a patient-specific immobilization structure that is attachable to the support structure for immobilizing the body portion between the patient-specific immobilization structure and the support structure.

42. The system according to claim 41 further comprising a fabrication device connectable to the processing circuitry for fabricating the patient-specific immobilization structure according to the digital model.

43. A method of generating a digital model of an immobilization device for immobilizing a body portion of a patient, the method comprising:

receiving image data suitable for characterizing an exposed surface of a body portion of the patient and at least a portion of a support structure employed to support the body portion during imaging;

processing the image data to determine a position and orientation of the support structure based on one or more known spatial features of the support structure;

processing the image data to segment surface data associated with the exposed surface of the body portion; and employing the surface data and the position and orientation of the support structure to generate the digital model of a patient-specific immobilization structure that is attachable to the support structure for immobilizing the body portion between the patient-specific immobilization structure and the support structure.

44. A method of generating a digital model of an immobilization device for immobilizing a body portion of a patient, the method comprising:

obtaining image data suitable for characterizing an exposed surface of the body portion and at least a portion of a support structure employed to support the body portion during imaging;

processing the image data to determine a position and orientation of the support structure based on one or more known spatial features of the support structure;

processing the image data to segment surface data associated with the exposed surface of the body portion; and employing the surface data and the position and orientation of the support structure to generate a digital model of a patient-specific immobilization structure that is attachable to the support structure for immobilizing the body portion between the patient-specific immobilization structure and the support structure.

45. A system for generating a digital model of an immobilization device for immobilizing a body portion of a patient, the system comprising:

control and processing circuitry comprising at least one processor and associated memory, said memory comprising instructions executable by said at least one processor for performing operations comprising:

obtaining image data suitable for characterizing an exposed surface of the body portion and at least a portion of a support structure employed to support the body portion during imaging;

processing the image data to determine a position and orientation of the support structure based on one or more known spatial features of the support structure;

processing the image data to segment surface data associated with the exposed surface of the body portion; and employing the surface data and the position and orientation of the support structure to generate a digital model of a patient-specific immobilization structure that is attachable to the support structure for immobilizing the body portion between the patient-specific immobilization structure and the support structure.

46. A system for fabricating an immobilization device for immobilizing a body portion of a patient, the system comprising:

an imaging system;

a fabrication system; and control and processing circuitry operatively coupled to said imaging system and said fabrication system, said control and processing circuitry comprising at least one processor and associated memory, said memory comprising instructions executable by said at least one processor for performing operations comprising:

controlling said imaging system to obtain image data suitable for characterizing an exposed surface of the body portion and at least a portion of a support structure employed to support the body portion during imaging;

processing the image data to determine a position and orientation of the support structure based on one or more known spatial features of the support structure;

processing the image data to segment surface data associated with the exposed surface of the body portion;

employing the surface data and the position and orientation of the support structure to generate a digital model of a patient-specific immobilization structure that is attachable to the support structure for immobilizing the body portion between the patient-specific immobilization structure and the support structure; and controlling said fabrication system to fabricate the patient-specific immobilization structure according to the digital model.

* * * * *